US011162088B2

(12) United States Patent
Schatte et al.

(10) Patent No.: US 11,162,088 B2
(45) Date of Patent: Nov. 2, 2021

(54) PRODUCTION OF THIOESTERS USING SORTASE

(71) Applicant: Hoffmann-La Roche Inc., Little Falls, NJ (US)

(72) Inventors: Martin Schatte, Karlsbad (DE); Mara Boenitz-Dulat, Tutzing (DE); Frank Bergmann, Iffeldorf (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/933,741

(22) Filed: Mar. 23, 2018

(65) Prior Publication Data

US 2018/0334661 A1   Nov. 22, 2018

Related U.S. Application Data

(63) Continuation of application No. PCT/EP2016/072512, filed on Sep. 22, 2016.

(30) Foreign Application Priority Data

Sep. 25, 2015 (EP) .................................... 15186953

(51) Int. Cl.
  *C12N 9/52* (2006.01)
  *A61K 47/65* (2017.01)
  *C12P 21/02* (2006.01)
  *C12P 11/00* (2006.01)

(52) U.S. Cl.
  CPC ................ *C12N 9/52* (2013.01); *A61K 47/65* (2017.08); *C12P 11/00* (2013.01); *C12P 21/02* (2013.01); *C12Y 304/2207* (2013.01)

(58) Field of Classification Search
  CPC .. A61K 47/48; A61K 31/5365; A61K 39/395; C12N 15/113; C07K 7/06; C07K 16/30
  See application file for complete search history.

(56) References Cited

U.S. PATENT DOCUMENTS

| 8,247,198 B2 | 8/2012 | Gorke et al. | |
|---|---|---|---|
| 10,864,277 B2 | 12/2020 | Grawunder et al. | |
| 2009/0117628 A1 | 7/2009 | Gorke et al. | |
| 2014/0030697 A1* | 1/2014 | Ploegh .................... | C12N 7/00 435/5 |
| 2014/0057317 A1 | 2/2014 | Liu et al. | |
| 2015/0152134 A1 | 4/2015 | Pentelute et al. | |
| 2016/0082046 A1 | 3/2016 | Lodish et al. | |
| 2016/0193355 A1* | 7/2016 | Qin .................... | A61K 47/6803 424/181.1 |

FOREIGN PATENT DOCUMENTS

| WO | 02/059148 | 8/2002 |
|---|---|---|
| WO | 2007/140371 A2 | 12/2007 |
| WO | 2010/087994 A2 | 8/2010 |
| WO | 2010/099536 A2 | 9/2010 |
| WO | 2010/099536 A3 | 9/2010 |
| WO | 2012/145522 | 10/2012 |
| WO | 2013/003555 A1 | 1/2013 |
| WO | 2013/016653 A1 | 1/2013 |
| WO | 2013/153203 | 10/2013 |
| WO | 2013/177231 | 11/2013 |
| WO | 2014/001324 A1 | 1/2014 |
| WO | 2014/001325 A1 | 1/2014 |
| WO | 2014/055936 | 4/2014 |
| WO | 2014/131906 A1 | 9/2014 |
| WO | 2014/145441 | 9/2014 |
| WO | 2014/177042 | 11/2014 |
| WO | 2014/183066 A2 | 11/2014 |

OTHER PUBLICATIONS

ISR and Written Opinion of PCT/EP2016/072512 (dated Nov. 17, 2016).
Ling et al., "Protein Thioester Synthesis Enabled by Sortase" J. Am. Chem. Soc. 134:10749-10752 ( 2012).
Race et al., "Crystal Structure of *Streptococcus pyogenes* Sortase A Implications for Sortase Mechanis" Journal of Biological Chemistry 284:6924-6933 ( 2009).
Schmohl et al., "Sortase-mediated ligations for the site-specific modification of proteins" Current Opinion in Chemical Biology 22:122-128 ( 2014).
Abbot et al., "Processing of Leather Using Deep Eutectic Solvents" CA Sustainable Chem Eng. 3(6):1241-1247 ( 2015).
Antos et al., "Site-Specific N- and C-Terminal Labeling of a Single Polypeptide Using Sortases of Different Specificity" Journal of the American Chemical Society 131:10800-10801 ( 2009).
Antos, John M., et al. "Supporting Information" Title: Site-specific N- and C-terminal labeling of a single polypeptide using sortases of different specificity, Whitehead Institute for Biomedical Research, 9 Cambridge Center, Cambridge, MA 02142, pp. S1-S20 (2009).
Biswas et al., "Sorting of LPXTG Peptides by Archetypal Sortase A: Role of Invariant Substrate Residues in Modulating the Enzyme Dynamics and Conformational Signature of a Productive Substrate" Biochemistry 53(15):2515-2524 ( 2014).
Branden et al. Introduction to Protein Structure "Prediction, Engineering, and Design of Protein Structures" New York:Garland Publishing Inc.,:247 ( 1991).
Clancy et al., "Sortase transpeptidases: Insights into mechanism, substrate specificity, and inhibition" Biopolymers 94(4):385-396 ( 2010).
Dai et al. Natural Deep Eutectic Solvents and Their Application in Natural Product Research and Development, Dissertation "3"Universiteit Leiden, ( 2013).

(Continued)

*Primary Examiner* — Maryam Monshipouri
(74) *Attorney, Agent, or Firm* — Nicole Fortune

(57) ABSTRACT

Herein is reported a method for the enzymatic production of a thioester comprising incubating i) a first polypeptide comprising the amino acid sequence LPXTG (SEQ ID NO: 01, wherein X can be any amino acid residue), ii) a second polypeptide that has at its N-terminus a cysteine amino acid residue or is a cysteinyl compound, and iii) a third polypeptide with sortase A activity.

16 Claims, 13 Drawing Sheets

Specification includes a Sequence Listing.

(56) References Cited

OTHER PUBLICATIONS

Frankel et al., "*Staphylococcus aureus* Sortase Transpeptidase SrtA: Insight into the Kinetic Mechanism and Evidence for a Reverse Protonation Catalytic Mechanism" Biochemistry 44(33):11188-11200 ( 2005).
Gaspar et al., "Baccillus anthracis Sortase A (SrtA) Anchors LPXTG Motif-Containing Surface Proteins to the Cell Wall Envelope" J of Bacteriology:4646-4655 ( 2005).
Heck et al., "Continuous Monitoring of Enzymatic Reactions on Surfaces by Real-Time Flow Cytometry: Sortase a Catalyzed Protein Immobilization as a Case Study" Bioconjugate Chemistry 25(8):1492-1500 ( 2014).
Hess et al., "M13 Bacteriophage Display Framework that Allows Sortase-Mediated Modification of Surface-Accessible Phage Proteins" Bioconjugate Chemistry 23:1478-1487 ( 2012).
International Search Report for PCT/EP2015/079692 dated Mar. 16, 2016.
International Search Report of PCT/EP2015/079615 dated Mar. 14, 2016.
ISR for PCT/EP2017/052318 (May 4, 2017).
ISR of PCT/EP2016/072510 (Date of mailing Nov. 15, 2016).
Levary et al., "Protein-Protein Fusion Catalyzed by Sortase A" PLoS ONE 6(4 Suppl e18342):1-6 ( 2011).
Li et al., "A novel reporter system monitoring Sortase A catalyzed protein ligation efficiency" Chinese Journal of Biotechnology 30(2):284-293 ( 2014).
Li et al., "Irreversible Site-Specific Hydrazinolysis of Proteins by Use of Sortase" Angewandte Chemie International Edition in English 53:2198-2202 ( 2014).
Madej et al., "Engineering of an Anti-Epidermal Growth Factor Receptor Antibody to Single Chain format and Labeling by Sortase A-Mediated Protein Ligation" Biotechnology and Bioengineering 109(6):1461-1470 ( 2012).
Marraffini et al., "Anchoring of Surface Proteins to the Cell Wall of *Staphylococcus aureus*" Journal of Biological Chemistry 279(36):37763-37770 (Sep. 3, 2004).
Marraffini et al., "Sortases and the Art of Anchoring Proteins to the Envelopes of Gram-Positive Bacteria" Microbiology and Molecular Biology Reviews 70:192-221 ( 2006).
Marvin et al., "Recombinant approaches to IgG-like bispecific antibodies" Acta Pharmacologica Sinica 26(6):649-658 (Jun. 2005).
Matsumoto et al., "Site-Specific Tetrameric Streptavidin-Protein Conjugation Using Sortase A" Journal of Biotechnology 152:37-42 ( 2011).
Matsumoto et al., "Sortase A-Catalyzed Site-Specific Coimmobilization on Microparticles via Streptavidin" Langmuir 28(7):3553-3557 ( 2012).
Maugeri et al., "Chymotrypsin-Catalyzed Peptide Synthesis in Deep Eutectic Solvents" European Journal of Organic Chemistry:4223-4228 ( 2013).
Meissner, P. et al. et al., "Transient gene expression: recombinant protein production with suspension-adapted HEK293-EBNA cells" Biotechnol Bioeng 75:197-203 ( 2001).
NCBI Database, 002984641.1, (sortase SrtA [*Streptococcus pyogenes*]), pp. PN 171203 May 2013.
NCBI Database, 031862293.1, (sortase A [*Staphylococcus aureus*]), pp. PN 171203 Sep. 2014.
Oteng-Pabi et al., "Continuous enzyme-coupled assay for microbial transglutaminase activity" Analytical Biochemistry 441(2):169-173 ( 2013).
Popp et al., "Making and Breaking Peptide Bonds: Protein Engineering Using Sortase" Angew. Chem. Int. Ed. 50:5024-5032 ( 2011).
Popp et al., "Sortase-catalyzed transformations that improve the properties of cytokines" PNAS 108:3169-3174 ( 2011).
Sadowski et al., "The sequence-structure relationship and protein function prediction" Current Opinion in Structural Biology 19:357-362 ( 2009).

Seffernick, J. et al., "Melamine Deaminase and Atrazine Chlorohydrolase: 98 Percent Identical but Functionally Different" Journal of Bacteriology 183(8):2405-2410 ( 2001).
Smith et al., "Deep Eutectic Solvents (DESs) and Their Applications" Chemical Reviews 114:11060-11082 ( 2014).
Strijbis, K. et al., "Protein Ligation in Living Cells Using Sortase" Traffic 13:780-789 ( 2012).
Ta et al., "Enzymatic Single-Chain Antibody Tagging a Universal Approach to Targeted Molecular Imaging and Cell Homing in Cardiovascular Disease" Circulation Research 109:365-373 ( 2011).
Tan et al., "Applications of Transpeptidase Sortase A for Protein Modifications" Progress in Chemistry 26(10):1741-1751 ( 2014).
Tang et al., "Identification of Dehalobacter reductive dehalogenases that catalyse dechlorination of chloroform, 1,1,1-trichloroethane and 1,1-dichloroethane" Philosophical Transactions of The Royal Society B 368:1-10 ( 2013).
Ton-That et al., "Anchoring of surface proteins to the cell wall of *Staphylococcus aureus*. Sortase catalyzed in vitro transpeptidation reaction using LPXTG peptide and NH(2)-Gly(3) substrates" The Journal of biological chemistry 275(13):9876-81 ( 2000).
Ton-That et al., "Anchoring of Surface Proteins to the Cell Wall of *Staphylococcus aureus*" Journal of Biological Chemistry 277(9):7447-7452 ( 2002).
Ton-That et al., "Purification and Characterization of Sortase, the Transpeptidase that Cleaves Surface Proteins of *Staphylococcus aureus* at the LPXTG Motif" PNAS 96(22):12424-12429 (Oct. 26, 1999).
Tsukiji et al., "Sortase-Mediated Ligation: A Gift from Gram-Positive Bacteria to Protein Engineering" ChemBioChem 10:787-798 ( 2009).
Walsh, Christopher Antibiotics: actions, origins, resistance Washington, D.C.:ASM Press, ( 2003).
Witkiowski, A. et al, "Conversion of a â-Ketoacyl Synthase to a Malonyl Deearboxylase by Replacement of the Active-Site Cysteine with Glutamine" Biochemistry 38:11643-11650 ( 1999).
Written Opinion for PCT/EP2017/052318.
Yamamura et al., "Enhancement of Sortase A-Mediated Protein Ligation by Inducing a beta-Hairpin Structure around the Ligation Site" Chem. Commun. 47:4742-4744 ( 2011).
Zhao et al., "Protease activation in glycerol-based deep eutectic solvents" J Mol Catal B Enzym. 72:163-167 ( 2011).
Clancy et al., "Sortase Transpeptidases: Insights into mechanism, substrate specificity and inhibition" Peptide Science 94(4):385-396 ( 2010).
Durand et al., "Deep eutectic solvents: Synthesis, application, and focus on lipase-catalyzed reactions" Eur. J. Lipid Sci. Technol. 115:379-385 ( 2013).
Garandeau et al., "The Sortase SrtA of Listeria monocytogenes is Involved in Processing of Internalin and in Virulence" Infection and Immunity:1382-1390 (Mar. 2002).
Garcia et al., "Deep Eutectic Solvents: Physicochemical Properties and Gas Separation Applications" Energy & Fuels 29:2616-2644 ( 2015).
Guimaraes et al., "Site-specific C-terminal and internal loop labeling of proteins using sortase-mediated reactions" Nature Protocols 8:1787-1799 ( 2013).
Hongyuan et al., "Sortase-Mediated Protein Ligation: A New Method for Protein Engineering" J. Am. Chem. Soc. 126:2670-2671 ( 2004).
Huang et al., "Deep eutectic solvents can be viable enzyme activators and stabilizers" Journal of Chem. Technol Biotechnol 89:1875-1981 ( 2014).
ISR for PCT/EP2016/072502 (Date of mailing Nov. 8, 2016).
Jiang et al., "Research Progress on Sortase and its Application in Biotechnology" Current Biotechnology 1(3):184-188 ( 2011).
Kyoui et al., "Genetic distance in the whole-genome perspective on Listeria monocytogenes strains F2-382 and NIHS-28 that show similar subtyping results" BMC Microbiology 14:309 ( 2014).
Lindberg et al., "Deep eutectic solvents (DESs) are viable cosolvents for enzyme-catalyzed epoxide hydrolysis" Journal of Biotechnology 147:169-171 ( 2010).
Nguyen et al., "Establishment of an experimental system allowing immobilization of proteins on the surface of Bacillus subtilis cells" Journal of Biotechnology 122:473-482 ( 2006).

(56) References Cited

OTHER PUBLICATIONS

Other Database, Database EBI accession No. UNIPROT:AOAOE1R5I2, (SubName: Full=Putative cysteine protease ywpE {ECO:0000313|EMBL:CCO63533.1}; EC=3.4.22.— {ECO:0000313|EMBL:CCO63533.1};) May 27, 2015.
Other Database, UNIPROT:A0A0B8RCN4,Database accession No. UNIPROT:A0A0B8RCN4 SubName: Full=Cysteine protease {ECO:0000313:EMBL:GAM94542.1}; SubName: Full=Sortase {ECO:00003131EMBL:AGR15336.1}; SubName: Full=Sortase A {ECO:0000313:EMBL:AKK25356.1} Sep. 16, 2015.
Other Database, UNIPROT:A9LY59,retrieved from EBI accession No. UNIPROT:A9LY59, SubName: Full=Sortase A {ECO:0000313:EMBL:ABX11549.1}; Flags: Fragment; Feb. 5, 2008.
Sutherland and Durand, Recent Results Cancer Res 95:24-49 ( 1984).
Tang et al., "Recent developments in deep eutectic solvents in chemical sciences" Monatsh Chem. 144:1427-1454 ( 2013).
Zhang et al., "Deep eutectic solvents: syntheses, properties and applications" Chem Soc Rev 41:7108-7146 ( 2012).
Zhao et al., "Choline-based deep eutectic solvents for enzymatic preparation of biodiesel from soybean oil" Journal of Molecular Catalysis B: Enzymatic 85-86:243-247 ( 2013).
Bierne et al., "Inactivation of the srtA gene in Listeria monocytogenes inhibits anchoring of surface proteins and affects virulence" Molecular Microbiology 43(4):869-881 ( 2002).
Bolken et al., "Inactivation of the srtA gene in *Streptococcus gordonii* inhibits cell wall anchoring of surface proteins and decreases in vitro and in vivo adhesion" Infection and Immunity 69(1):75-80 ( 2001).
Chan et al., "Covalent attachment of proteins to solid supports and surfaces via sortase-mediated ligation" PlosOne(11):e1164 ( 2007).
Dawson et al., "Synthesis of Native Proteins by Chemical Ligation" Annu. Rev. Biochem 69:923-60 ( 2000).
Dhar et al., "Anchor Structure of cell wall surface proteins in listeria monocytogenes" Biochemistry 39(13):3725-3733 ( 2000).

Fischetti et al., "Conservation of a hexapeptide sequence in the anchor region of surface proteins from Gram-positive cocci" Molecular Microbiology 4(9):1603-1605 ( 1990).
Glaser et al., "Comparative genomics of *Listeria* species" Science 294:849-852 ( 2001).
Ilangovan et al., "Structure of sortase, the transpeptidase that anchors proteins to the cell wall of *Staphylococcus aureus*" Proceedings of the National Academy of Sciences 98(11):6056-6061 ( 2001).
Kruger et al., "Analysis of the substrate specificity of the staphylococcus aureus sortase transpeptidase SrtA" Biochemistry 43(6):1541-1551 ( 2004).
Mao et al., "Sortase-Mediated protein ligation: A new method for protein engineering" Journal of American Chemical Society 126:2670-2671 ( 2004).
Mazmanian et al., "Sortase-catalysed anchoring of surface proteins to the cell wall of *Staphylococcus aureus*" Molecular Microbiology 40(5):1049-1057 ( 2001).
Mazmanian et al., "*Staphylococcus aureus* Sortase, an enzyme that anchors surface proteins to the cell wall" Science 285:760-763 ( 1999).
Pallen et al., "An embarrassment of sortases—a richness of substrates?" TRENDS in Microbiology 9(3):97-102 ( 2001).
Parthasarathy et al., Bioconjugate Chem 18:469-476 ( 2007).
Samantaray et al., "Peptide-sugar ligation catalyzed by transpeptidase sortase: A facile approach to neoglycoconjugate synthesis" Journal Am. Chem. Soc. 130:2132-2133 ( 2008).
Yan et al., "Synthesis of Peptides and Proteins without Cysteine Residues by Native Chemical Ligation Combined with Desulfurization" Journal Am. Chem. Soc. 123:526-533 ( 2001).
Swee et al., "Sortase-mediated modification of alphaDEC205 affords optimization of antigen presentation and immunization against a set of viral epitopes" PNAS 110(4):1428-1433 ( 2013).
Tanaka et al., "Site-Specific Protein Modification on Living Cells Catalyzed by Sortase" ChemBioChem 9:802-807 ( 2008).
Witte et al., "Preparation of unnatural N-to-N and C-to-C protein fusions" PNAS 109(30):11993-11998 ( 2012).

\* cited by examiner

SEQUENCE LISTING

```
<160> NUMBER OF SEQ ID NOS: 154

<210> SEQ ID NO 1
<211> LENGTH: 5
<212> TYPE: PRT
<213> ORGANISM: Staphylococcus aureus
<220> FEATURE:
<221> NAME/KEY: MISC_FEATURE
<222> LOCATION: (3)..(3)
<223> OTHER INFORMATION: X can be any amino acid residue

<400> SEQUENCE: 1

Leu Pro Xaa Thr Gly
1               5

<210> SEQ ID NO 2
<211> LENGTH: 4
<212> TYPE: PRT
<213> ORGANISM: Artificial Sequence
<220> FEATURE:
<223> OTHER INFORMATION: cystein sortase motif 1

<400> SEQUENCE: 2

Cys Gly Gly Gly
1

<210> SEQ ID NO 3
<211> LENGTH: 4
<212> TYPE: PRT
<213> ORGANISM: Artificial Sequence
<220> FEATURE:
<223> OTHER INFORMATION: cystein sortase motif 2

<400> SEQUENCE: 3

Cys Ala Ala Ala
1

<210> SEQ ID NO 4
<211> LENGTH: 5
<212> TYPE: PRT
<213> ORGANISM: Artificial Sequence
<220> FEATURE:
<223> OTHER INFORMATION: sortase motif

<400> SEQUENCE: 4

Leu Pro Glu Thr Gly
1               5

<210> SEQ ID NO 5
<211> LENGTH: 147
<212> TYPE: PRT
<213> ORGANISM: Artificial Sequence
<220> FEATURE:
<223> OTHER INFORMATION: Staphylococcus aureus Sortase A shortened
      version

<400> SEQUENCE: 5

Gln Ala Lys Pro Gln Ile Pro Lys Asp Lys Ser Lys Val Ala Gly Tyr
1               5                   10                  15

Ile Glu Ile Pro Asp Ala Asp Ile Lys Glu Pro Val Tyr Pro Gly Pro
            20                  25                  30
```

```
Ala Thr Pro Glu Gln Leu Asn Arg Gly Val Ser Phe Ala Glu Glu Asn
            35                  40                  45

Glu Ser Leu Asp Asp Gln Asn Ile Ser Ile Ala Gly His Thr Phe Ile
 50                  55                  60

Asp Arg Pro Asn Tyr Gln Phe Thr Asn Leu Lys Ala Ala Lys Lys Gly
 65                  70                  75                  80

Ser Met Val Tyr Phe Lys Val Gly Asn Glu Thr Arg Lys Tyr Lys Met
                 85                  90                  95

Thr Ser Ile Arg Asp Val Lys Pro Thr Asp Val Gly Val Leu Asp Glu
             100                 105                 110

Gln Lys Gly Lys Asp Lys Gln Leu Thr Leu Ile Thr Cys Asp Asp Tyr
             115                 120                 125

Asn Glu Lys Thr Gly Val Trp Glu Lys Arg Lys Ile Phe Val Ala Thr
 130                 135                 140

Glu Val Lys
 145
```

```
<210> SEQ ID NO 6
<211> LENGTH: 150
<212> TYPE: PRT
<213> ORGANISM: Artificial Sequence
<220> FEATURE:
<223> OTHER INFORMATION: Listeria monocytogenes Sortase A shortened
      version

<400> SEQUENCE: 6
```

```
Ala Asn Tyr Asp Lys Asp Ala Val Val Gly Ser Ile Ala Val Pro Ser
 1               5                  10                  15

Val Asp Val Asn Leu Leu Val Phe Lys Gly Thr Asn Thr Ala Asn Leu
                 20                  25                  30

Leu Ala Gly Ala Thr Thr Met Arg Ser Asp Gln Val Met Gly Lys Gly
             35                  40                  45

Asn Tyr Pro Leu Ala Gly His His Met Arg Asp Glu Ser Met Leu Phe
 50                  55                  60

Gly Pro Ile Met Lys Val Lys Lys Gly Asp Lys Ile Tyr Leu Thr Asp
 65                  70                  75                  80

Leu Glu Asn Leu Tyr Glu Tyr Thr Val Thr Glu Thr Lys Thr Ile Asp
                 85                  90                  95

Glu Thr Glu Val Ser Val Ile Asp Asp Thr Lys Asp Ala Arg Ile Thr
             100                 105                 110

Leu Ile Thr Cys Asp Lys Pro Thr Glu Thr Thr Lys Arg Phe Val Ala
             115                 120                 125

Val Gly Glu Leu Glu Lys Thr Glu Lys Leu Thr Lys Glu Leu Glu Asn
 130                 135                 140

Lys Tyr Phe Pro Ser Lys
 145                 150
```

```
<210> SEQ ID NO 7
<211> LENGTH: 5
<212> TYPE: PRT
<213> ORGANISM: Artificial Sequence
<220> FEATURE:
<223> OTHER INFORMATION: Arg-tag

<400> SEQUENCE: 7

Arg Arg Arg Arg Arg
 1               5
```

```
<210> SEQ ID NO 8
<211> LENGTH: 6
<212> TYPE: PRT
<213> ORGANISM: Artificial Sequence
<220> FEATURE:
<223> OTHER INFORMATION: Arg-tag 2

<400> SEQUENCE: 8

Arg Arg Arg Arg Arg Arg
1               5

<210> SEQ ID NO 9
<211> LENGTH: 6
<212> TYPE: PRT
<213> ORGANISM: Artificial Sequence
<220> FEATURE:
<223> OTHER INFORMATION: His-tag

<400> SEQUENCE: 9

His His His His His His
1               5

<210> SEQ ID NO 10
<211> LENGTH: 19
<212> TYPE: PRT
<213> ORGANISM: Artificial Sequence
<220> FEATURE:
<223> OTHER INFORMATION: amino acid tag

<400> SEQUENCE: 10

Lys Asp His Leu Ile His Asn Val His Lys Glu Phe His Ala His Ala
1               5                   10                  15

His Asn Lys

<210> SEQ ID NO 11
<211> LENGTH: 8
<212> TYPE: PRT
<213> ORGANISM: Artificial Sequence
<220> FEATURE:
<223> OTHER INFORMATION: amino acid tag

<400> SEQUENCE: 11

Asp Tyr Lys Asp Asp Asp Asp Lys
1               5

<210> SEQ ID NO 12
<211> LENGTH: 22
<212> TYPE: PRT
<213> ORGANISM: Artificial Sequence
<220> FEATURE:
<223> OTHER INFORMATION: amino acid tag

<400> SEQUENCE: 12

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 13
<211> LENGTH: 9
<212> TYPE: PRT
<213> ORGANISM: Artificial Sequence
<220> FEATURE:
<223> OTHER INFORMATION: amino acid tag#

<400> SEQUENCE: 13
```

```
Ala Trp Arg His Pro Gln Phe Gly Gly
1               5
```

<210> SEQ ID NO 14
<211> LENGTH: 8
<212> TYPE: PRT
<213> ORGANISM: Artificial Sequence
<220> FEATURE:
<223> OTHER INFORMATION: amino acid tag

<400> SEQUENCE: 14

```
Trp Ser His Pro Gln Phe Glu Lys
1               5
```

<210> SEQ ID NO 15
<211> LENGTH: 10
<212> TYPE: PRT
<213> ORGANISM: Artificial Sequence
<220> FEATURE:
<223> OTHER INFORMATION: amino acid tag

<400> SEQUENCE: 15

```
Met Asp Val Glu Ala Trp Leu Gly Ala Arg
1               5                   10
```

<210> SEQ ID NO 16
<211> LENGTH: 16
<212> TYPE: PRT
<213> ORGANISM: Artificial Sequence
<220> FEATURE:
<223> OTHER INFORMATION: amino acid tag

<400> SEQUENCE: 16

```
Met Asp Val Glu Ala Trp Leu Gly Ala Arg Val Pro Leu Val Glu Thr
1               5                   10                  15
```

<210> SEQ ID NO 17
<211> LENGTH: 38
<212> TYPE: PRT
<213> ORGANISM: Artificial Sequence
<220> FEATURE:
<223> OTHER INFORMATION: amino acid tag

<400> SEQUENCE: 17

```
Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35
```

<210> SEQ ID NO 18
<211> LENGTH: 10
<212> TYPE: PRT
<213> ORGANISM: Artificial Sequence
<220> FEATURE:
<223> OTHER INFORMATION: amino acid tag

<400> SEQUENCE: 18

```
Glu Gln Lys Leu Ile Ser Glu Glu Asp Leu
1               5                   10
```

<210> SEQ ID NO 19
<211> LENGTH: 15
<212> TYPE: PRT

```
<213> ORGANISM: Artificial Sequence
<220> FEATURE:
<223> OTHER INFORMATION: amino acid tag

<400> SEQUENCE: 19

Lys Glu Thr Ala Ala Ala Lys Phe Glu Arg Gln His Met Asp Ser
1               5                   10                  15

<210> SEQ ID NO 20
<211> LENGTH: 26
<212> TYPE: PRT
<213> ORGANISM: Artificial Sequence
<220> FEATURE:
<223> OTHER INFORMATION: amino acid tag

<400> SEQUENCE: 20

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 21
<211> LENGTH: 47
<212> TYPE: PRT
<213> ORGANISM: Artificial Sequence
<220> FEATURE:
<223> OTHER INFORMATION: amino acid tag

<400> SEQUENCE: 21

Pro Ala Thr Thr Thr Gly Ser Ser Pro Gly Pro Thr Gln Ser His Tyr
1               5                   10                  15

Gly Gln Cys Gly Gly Ile Gly Tyr Ser Gly Pro Thr Val Cys Ala Ser
            20                  25                  30

Gly Thr Thr Cys Gln Val Leu Asn Pro Tyr Tyr Ser Gln Cys Leu
        35                  40                  45

<210> SEQ ID NO 22
<211> LENGTH: 32
<212> TYPE: PRT
<213> ORGANISM: Butyrivibrio fibrisolvens

<400> SEQUENCE: 22

Met Asp Trp Asn Ala Asn Ile Ala Pro Gly Asn Ser Val Glu Phe Gly
1               5                   10                  15

Ile Gln Gly Ala Gly Ser Val Gly Asn Val Ile Asp Ile Thr Val Glu
            20                  25                  30

<210> SEQ ID NO 23
<211> LENGTH: 51
<212> TYPE: PRT
<213> ORGANISM: Artificial Sequence
<220> FEATURE:
<223> OTHER INFORMATION: chitin-binding-domain

<400> SEQUENCE: 23

Thr Asn Pro Gly Val Ser Ala Trp Gln Val Asn Thr Ala Tyr Thr Ala
1               5                   10                  15

Gly Gln Leu Val Thr Tyr Asn Gly Lys Thr Tyr Lys Cys Leu Gln Pro
            20                  25                  30

His Thr Ser Leu Ala Gly Trp Glu Pro Ser Asn Val Pro Ala Leu Trp
        35                  40                  45

Gln Leu Gln
    50
```

<210> SEQ ID NO 24
<211> LENGTH: 209
<212> TYPE: PRT
<213> ORGANISM: Chondrus crispus

<400> SEQUENCE: 24

Met Pro Glu Ile Lys Leu Thr Tyr Phe Asp Met Arg Gly Arg Ala Glu
1               5                   10                  15

Ala Ser Arg Leu Ala Leu Val Val Gly Glu Ile Pro Phe Glu Asp Glu
            20                  25                  30

Arg Val Val Phe Asp His Trp Lys Glu Ala Lys Pro Lys Thr Pro Tyr
        35                  40                  45

Ala Ala Leu Pro Met Leu Thr Val Asp Gly Met Gln Val Ala Gln Ser
    50                  55                  60

Asp Ala Ile Leu Arg Tyr Cys Gly Lys Leu Ala Gly Leu Tyr Pro Ser
65                  70                  75                  80

Asp Pro Leu Glu Ala Ala Lys Val Asp Glu Val Gly Gly Val Ile Asp
                85                  90                  95

Asp Val Thr His Ala Met Tyr Arg Tyr Arg Gly Asp Asp Lys Asp Lys
            100                 105                 110

Leu Arg Glu Glu Arg Asp Lys Phe Ser Lys Val Asp Val Pro Arg Tyr
        115                 120                 125

Val Gly Ala Leu Glu Lys Arg Leu Glu Ala Phe Gly Asp Gly Pro Trp
    130                 135                 140

Ala Val Gly Gly Asn Met Thr Ile Ala Asp Leu His Ile Cys His Leu
145                 150                 155                 160

Val Thr Asn Ile Arg Cys Gly Met Leu Asp Phe Val Asp Lys Asp Leu
                165                 170                 175

Leu Glu Gly Tyr Val Arg Ile Val Lys Ser Tyr Ser Ala Val Met Glu
            180                 185                 190

His Pro Lys Val Thr Glu Trp Tyr Glu Lys Pro Val Lys Met Phe
        195                 200                 205

Ser

<210> SEQ ID NO 25
<211> LENGTH: 396
<212> TYPE: PRT
<213> ORGANISM: Escherichia coli

<400> SEQUENCE: 25

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

-continued

```
Asp Lys Leu Tyr Pro Phe Thr Trp Asp Ala Val Arg Tyr Asn Gly Lys
            115                 120                 125

Leu Ile Ala Tyr Pro Ile Ala Val Glu Ala Leu Ser Leu Ile Tyr Asn
        130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
    370                 375                 380

Glu Ala Leu Lys Asp Ala Gln Thr Arg Ile Thr Lys
385                 390                 395

<210> SEQ ID NO 26
<211> LENGTH: 206
<212> TYPE: PRT
<213> ORGANISM: Staphylococcus aureus

<400> SEQUENCE: 26

Met Lys Lys Trp Thr Asn Arg Leu Met Thr Ile Ala Gly Val Val Leu
1               5                   10                  15

Ile Leu Val Ala Ala Tyr Leu Phe Ala Lys Pro His Ile Asp Asn Tyr
            20                  25                  30

Leu His Asp Lys Asp Lys Asp Glu Lys Ile Glu Gln Tyr Asp Lys Asn
        35                  40                  45

Val Lys Glu Gln Ala Ser Lys Asp Lys Gln Ala Lys Pro Gln
    50                  55                  60

Ile Pro Lys Asp Lys Ser Lys Val Ala Gly Tyr Ile Glu Ile Pro Asp
65                  70                  75                  80

Ala Asp Ile Lys Glu Pro Val Tyr Pro Gly Pro Ala Thr Pro Glu Gln
                85                  90                  95
```

Leu Asn Arg Gly Val Ser Phe Ala Glu Glu Asn Glu Ser Leu Asp Asp
              100                 105                 110

Gln Asn Ile Ser Ile Ala Gly His Thr Phe Ile Asp Arg Pro Asn Tyr
            115                 120                 125

Gln Phe Thr Asn Leu Lys Ala Ala Lys Lys Gly Ser Met Val Tyr Phe
        130                 135                 140

Lys Val Gly Asn Glu Thr Arg Lys Tyr Lys Met Thr Ser Ile Arg Asp
145                 150                 155                 160

Val Lys Pro Thr Asp Val Gly Val Leu Asp Glu Gln Lys Gly Lys Asp
                165                 170                 175

Lys Gln Leu Thr Leu Ile Thr Cys Asp Asp Tyr Asn Glu Lys Thr Gly
            180                 185                 190

Val Trp Glu Lys Arg Lys Ile Phe Val Ala Thr Glu Val Lys
        195                 200                 205

<210> SEQ ID NO 27
<211> LENGTH: 222
<212> TYPE: PRT
<213> ORGANISM: Listeria monocytogenes

<400> SEQUENCE: 27

Met Leu Lys Lys Thr Ile Ala Ala Ala Leu Ala Ala Gly Leu Leu
1               5                   10                  15

Leu Ile Phe Ser Pro Phe Ile Lys Asn Gly Ile Val Lys Tyr Met Ser
            20                  25                  30

Gly His Glu Thr Ile Glu Gln Tyr Lys Ala Ser Asp Ile Lys Lys Asn
        35                  40                  45

Asn Glu Lys Asp Ala Thr Phe Asp Phe Glu Ser Val Gln Leu Pro Ser
    50                  55                  60

Met Thr Ser Val Ile Lys Gly Ala Ala Asn Tyr Asp Lys Asp Ala Val
65                  70                  75                  80

Val Gly Ser Ile Ala Val Pro Ser Val Asp Val Asn Leu Leu Val Phe
                85                  90                  95

Lys Gly Thr Asn Thr Ala Asn Leu Leu Ala Gly Ala Thr Thr Met Arg
            100                 105                 110

Ser Asp Gln Val Met Gly Lys Gly Asn Tyr Pro Leu Ala Gly His His
        115                 120                 125

Met Arg Asp Glu Ser Met Leu Phe Gly Pro Ile Met Lys Val Lys Lys
    130                 135                 140

Gly Asp Lys Ile Tyr Leu Thr Asp Leu Glu Asn Leu Tyr Glu Tyr Thr
145                 150                 155                 160

Val Thr Glu Thr Lys Thr Ile Asp Glu Thr Glu Val Ser Val Ile Asp
                165                 170                 175

Asn Thr Lys Asp Ala Arg Ile Thr Leu Ile Thr Cys Asp Lys Pro Thr
            180                 185                 190

Glu Thr Thr Lys Arg Phe Val Ala Val Gly Leu Glu Lys Thr Glu
        195                 200                 205

Lys Leu Thr Lys Glu Leu Glu Asn Lys Tyr Phe Pro Ser Lys
    210                 215                 220

<210> SEQ ID NO 28
<211> LENGTH: 2
<212> TYPE: PRT
<213> ORGANISM: Artificial Sequence
<220> FEATURE:
<223> OTHER INFORMATION: oligogylcine

```
<400> SEQUENCE: 28

Gly Gly
1

<210> SEQ ID NO 29
<211> LENGTH: 3
<212> TYPE: PRT
<213> ORGANISM: Artificial Sequence
<220> FEATURE:
<223> OTHER INFORMATION: oligoglycine

<400> SEQUENCE: 29

Gly Gly Gly
1

<210> SEQ ID NO 30
<211> LENGTH: 4
<212> TYPE: PRT
<213> ORGANISM: Artificial Sequence
<220> FEATURE:
<223> OTHER INFORMATION: oligoglycine

<400> SEQUENCE: 30

Gly Gly Gly Gly
1

<210> SEQ ID NO 31
<211> LENGTH: 5
<212> TYPE: PRT
<213> ORGANISM: Artificial Sequence
<220> FEATURE:
<223> OTHER INFORMATION: oligoglycine

<400> SEQUENCE: 31

Gly Gly Gly Gly Gly
1               5

<210> SEQ ID NO 32
<211> LENGTH: 12
<212> TYPE: PRT
<213> ORGANISM: Artificial Sequence
<220> FEATURE:
<223> OTHER INFORMATION: hexa-histidine tag with linker

<400> SEQUENCE: 32

Met Arg Gly Ser His His His His His His Gly Ser
1               5                   10

<210> SEQ ID NO 33
<211> LENGTH: 11
<212> TYPE: PRT
<213> ORGANISM: Artificial Sequence
<220> FEATURE:
<223> OTHER INFORMATION: LCR640-ULPETGGGRRC
<220> FEATURE:
<221> NAME/KEY: MISC_FEATURE
<222> LOCATION: (1)..(1)
<223> OTHER INFORMATION: beta-analnine conjugated to LCR640-U

<400> SEQUENCE: 33

Xaa Leu Pro Glu Thr Gly Gly Gly Arg Arg Cys
1               5                   10

<210> SEQ ID NO 34
<211> LENGTH: 5
<212> TYPE: PRT
```

```
<213> ORGANISM: Artificial Sequence
<220> FEATURE:
<223> OTHER INFORMATION: sortase recognition motif
<220> FEATURE:
<221> NAME/KEY: MISC_FEATURE
<222> LOCATION: (3)..(3)
<223> OTHER INFORMATION: X=any amino acid residue except P

<400> SEQUENCE: 34

Leu Pro Xaa Thr Gly
1               5

<210> SEQ ID NO 35
<211> LENGTH: 4
<212> TYPE: PRT
<213> ORGANISM: Artificial Sequence
<220> FEATURE:
<223> OTHER INFORMATION: sortase recognition motif
<220> FEATURE:
<221> NAME/KEY: MISC_FEATURE
<222> LOCATION: (3)..(3)
<223> OTHER INFORMATION: X=any amino acid residue except P

<400> SEQUENCE: 35

Leu Pro Xaa Thr
1

<210> SEQ ID NO 36
<211> LENGTH: 5
<212> TYPE: PRT
<213> ORGANISM: Artificial Sequence
<220> FEATURE:
<223> OTHER INFORMATION: sortase recognition motif

<400> SEQUENCE: 36

Leu Pro Thr Thr Gly
1               5

<210> SEQ ID NO 37
<211> LENGTH: 5
<212> TYPE: PRT
<213> ORGANISM: Artificial Sequence
<220> FEATURE:
<223> OTHER INFORMATION: sortase recognition motif

<400> SEQUENCE: 37

Leu Pro Asp Thr Gly
1               5

<210> SEQ ID NO 38
<211> LENGTH: 5
<212> TYPE: PRT
<213> ORGANISM: Artificial Sequence
<220> FEATURE:
<223> OTHER INFORMATION: sortase recognition motif

<400> SEQUENCE: 38

Leu Pro Lys Thr Gly
1               5

<210> SEQ ID NO 39
<211> LENGTH: 5
<212> TYPE: PRT
<213> ORGANISM: Artificial Sequence
<220> FEATURE:
<223> OTHER INFORMATION: sortase recognition motif

<400> SEQUENCE: 39
```

Leu Pro Asn Thr Gly
1               5

<210> SEQ ID NO 40
<211> LENGTH: 5
<212> TYPE: PRT
<213> ORGANISM: Artificial Sequence
<220> FEATURE:
<223> OTHER INFORMATION: sortase recognition motif

<400> SEQUENCE: 40

Pro Leu Ala Ala Gly
1               5

<210> SEQ ID NO 41
<211> LENGTH: 5
<212> TYPE: PRT
<213> ORGANISM: Artificial Sequence
<220> FEATURE:
<223> OTHER INFORMATION: sortase recognition motif

<400> SEQUENCE: 41

Leu Pro Lys Ala Gly
1               5

<210> SEQ ID NO 42
<211> LENGTH: 5
<212> TYPE: PRT
<213> ORGANISM: Artificial Sequence
<220> FEATURE:
<223> OTHER INFORMATION: sortase recognition motif

<400> SEQUENCE: 42

Leu Pro Gln Thr Gly
1               5

<210> SEQ ID NO 43
<211> LENGTH: 5
<212> TYPE: PRT
<213> ORGANISM: Artificial Sequence
<220> FEATURE:
<223> OTHER INFORMATION: sortase recognition motif

<400> SEQUENCE: 43

Leu Pro Met Thr Gly
1               5

<210> SEQ ID NO 44
<211> LENGTH: 5
<212> TYPE: PRT
<213> ORGANISM: Artificial Sequence
<220> FEATURE:
<223> OTHER INFORMATION: sortase recognition motif

<400> SEQUENCE: 44

Leu Pro Ile Thr Gly
1               5

<210> SEQ ID NO 45
<211> LENGTH: 5
<212> TYPE: PRT
<213> ORGANISM: Artificial Sequence
<220> FEATURE:
<223> OTHER INFORMATION: sortase recognition motif

<400> SEQUENCE: 45

Leu Pro Asp Thr Ala

```
<210> SEQ ID NO 46
<211> LENGTH: 5
<212> TYPE: PRT
<213> ORGANISM: Artificial Sequence
<220> FEATURE:
<223> OTHER INFORMATION: sortase recognition motif

<400> SEQUENCE: 46

Ser Pro Lys Thr Gly
1               5

<210> SEQ ID NO 47
<211> LENGTH: 5
<212> TYPE: PRT
<213> ORGANISM: Artificial Sequence
<220> FEATURE:
<223> OTHER INFORMATION: sortase recognition motif

<400> SEQUENCE: 47

Leu Ala Glu Thr Gly
1               5

<210> SEQ ID NO 48
<211> LENGTH: 5
<212> TYPE: PRT
<213> ORGANISM: Artificial Sequence
<220> FEATURE:
<223> OTHER INFORMATION: sortase recognition motif

<400> SEQUENCE: 48

Leu Ala Ala Thr Gly
1               5

<210> SEQ ID NO 49
<211> LENGTH: 5
<212> TYPE: PRT
<213> ORGANISM: Artificial Sequence
<220> FEATURE:
<223> OTHER INFORMATION: sortase recognition motif

<400> SEQUENCE: 49

Leu Ala His Thr Gly
1               5

<210> SEQ ID NO 50
<211> LENGTH: 5
<212> TYPE: PRT
<213> ORGANISM: Artificial Sequence
<220> FEATURE:
<223> OTHER INFORMATION: sortase recognition motif

<400> SEQUENCE: 50

Leu Ala Ser Thr Gly
1               5

<210> SEQ ID NO 51
<211> LENGTH: 5
<212> TYPE: PRT
<213> ORGANISM: Artificial Sequence
<220> FEATURE:
<223> OTHER INFORMATION: sortase recognition motif

<400> SEQUENCE: 51

Leu Pro Leu Thr Gly
1               5
```

```
<210> SEQ ID NO 52
<211> LENGTH: 5
<212> TYPE: PRT
<213> ORGANISM: Artificial Sequence
<220> FEATURE:
<223> OTHER INFORMATION: sortase recognition motif

<400> SEQUENCE: 52

Leu Ser Arg Thr Gly
1               5

<210> SEQ ID NO 53
<211> LENGTH: 5
<212> TYPE: PRT
<213> ORGANISM: Artificial Sequence
<220> FEATURE:
<223> OTHER INFORMATION: sortase recognition motif

<400> SEQUENCE: 53

Val Pro Asp Thr Gly
1               5

<210> SEQ ID NO 54
<211> LENGTH: 5
<212> TYPE: PRT
<213> ORGANISM: Artificial Sequence
<220> FEATURE:
<223> OTHER INFORMATION: sortase recognition motif

<400> SEQUENCE: 54

Ile Pro Gln Thr Gly
1               5

<210> SEQ ID NO 55
<211> LENGTH: 5
<212> TYPE: PRT
<213> ORGANISM: Artificial Sequence
<220> FEATURE:
<223> OTHER INFORMATION: sortase recognition motif

<400> SEQUENCE: 55

Tyr Pro Arg Thr Gly
1               5

<210> SEQ ID NO 56
<211> LENGTH: 5
<212> TYPE: PRT
<213> ORGANISM: Artificial Sequence
<220> FEATURE:
<223> OTHER INFORMATION: sortase recognition motif

<400> SEQUENCE: 56

Leu Ala Leu Thr Gly
1               5

<210> SEQ ID NO 57
<211> LENGTH: 5
<212> TYPE: PRT
<213> ORGANISM: Artificial Sequence
<220> FEATURE:
<223> OTHER INFORMATION: sortase recognition motif

<400> SEQUENCE: 57

Leu Gly Asn Thr Gly
1               5
```

-continued

```
<210> SEQ ID NO 58
<211> LENGTH: 5
<212> TYPE: PRT
<213> ORGANISM: Artificial Sequence
<220> FEATURE:
<223> OTHER INFORMATION: sortase recognition motif

<400> SEQUENCE: 58

Leu Pro Gln Thr Ser
1               5

<210> SEQ ID NO 59
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: MISC_FEATURE
<222> LOCATION: (3)..(3)
<223> OTHER INFORMATION: X=any amino acid residue except P

<400> SEQUENCE: 59

Thr Leu Xaa Thr Cys
1               5

<210> SEQ ID NO 60
<211> LENGTH: 5
<212> TYPE: PRT
<213> ORGANISM: Artificial Sequence
<220> FEATURE:
<223> OTHER INFORMATION: sortase recognition motif

<400> SEQUENCE: 60

Asn Pro Gln Thr Asn
1               5

<210> SEQ ID NO 61
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: MISC_FEATURE
<222> LOCATION: (1)..(1)
<223> OTHER INFORMATION: X=L or M
<220> FEATURE:
<221> NAME/KEY: MISC_FEATURE
<222> LOCATION: (3)..(3)
<223> OTHER INFORMATION: X=any amino acid residue except P
<220> FEATURE:
<221> NAME/KEY: MISC_FEATURE
<222> LOCATION: (4)..(4)
<223> OTHER INFORMATION: X=A or L or S or T or V

<400> SEQUENCE: 61

Xaa Pro Xaa Xaa Gly
1               5

<210> SEQ ID NO 62
<211> LENGTH: 5
<212> TYPE: PRT
<213> ORGANISM: Artificial Sequence
<220> FEATURE:
<223> OTHER INFORMATION: sortase recognition motif

<400> SEQUENCE: 62

Ile Pro Lys Thr Gly
```

```
1               5
```

<210> SEQ ID NO 63
<211> LENGTH: 5
<212> TYPE: PRT
<213> ORGANISM: Artificial Sequence
<220> FEATURE:
<223> OTHER INFORMATION: sortase recognition motif

<400> SEQUENCE: 63

```
Ile Pro Ala Leu Gly
1               5
```

<210> SEQ ID NO 64
<211> LENGTH: 5
<212> TYPE: PRT
<213> ORGANISM: Artificial Sequence
<220> FEATURE:
<223> OTHER INFORMATION: sortase recognition motif

<400> SEQUENCE: 64

```
Leu Ala Ala Ser Ser
1               5
```

<210> SEQ ID NO 65
<211> LENGTH: 5
<212> TYPE: PRT
<213> ORGANISM: Artificial Sequence
<220> FEATURE:
<223> OTHER INFORMATION: sortase recognition motif

<400> SEQUENCE: 65

```
Leu Ala Pro Thr Gly
1               5
```

<210> SEQ ID NO 66
<211> LENGTH: 5
<212> TYPE: PRT
<213> ORGANISM: Artificial Sequence
<220> FEATURE:
<223> OTHER INFORMATION: sortase recognition motif

<400> SEQUENCE: 66

```
Leu Pro Ile Ser Ser
1               5
```

<210> SEQ ID NO 67
<211> LENGTH: 5
<212> TYPE: PRT
<213> ORGANISM: Artificial Sequence
<220> FEATURE:
<223> OTHER INFORMATION: sortase recognition motif

<400> SEQUENCE: 67

```
Leu Pro Lys Thr Ser
1               5
```

<210> SEQ ID NO 68
<211> LENGTH: 6
<212> TYPE: PRT
<213> ORGANISM: Artificial Sequence
<220> FEATURE:
<223> OTHER INFORMATION: sortase recognition motif

<400> SEQUENCE: 68

```
Tyr Ala Leu Pro Glu Thr
1               5
```

<210> SEQ ID NO 69
<211> LENGTH: 8
<212> TYPE: PRT
<213> ORGANISM: Artificial Sequence
<220> FEATURE:
<223> OTHER INFORMATION: sortase recognition motif

<400> SEQUENCE: 69

Tyr Ala Leu Pro Met Thr Gly Lys
1               5

<210> SEQ ID NO 70
<211> LENGTH: 4
<212> TYPE: PRT
<213> ORGANISM: Artificial Sequence
<220> FEATURE:
<223> OTHER INFORMATION: sortase recognition motif
<220> FEATURE:
<221> NAME/KEY: MISC_FEATURE
<222> LOCATION: (3)..(3)
<223> OTHER INFORMATION: X=any amino acid residue except P

<400> SEQUENCE: 70

Leu Pro Xaa Ala
1

<210> SEQ ID NO 71
<211> LENGTH: 4
<212> TYPE: PRT
<213> ORGANISM: Artificial Sequence
<220> FEATURE:
<223> OTHER INFORMATION: sortase recognition motif
<220> FEATURE:
<221> NAME/KEY: MISC_FEATURE
<222> LOCATION: (3)..(3)
<223> OTHER INFORMATION: X=any amino acid residue except P

<400> SEQUENCE: 71

Ser Pro Xaa Thr
1

<210> SEQ ID NO 72
<211> LENGTH: 4
<212> TYPE: PRT
<213> ORGANISM: Artificial Sequence
<220> FEATURE:
<223> OTHER INFORMATION: sortase recognition motif
<220> FEATURE:
<221> NAME/KEY: MISC_FEATURE
<222> LOCATION: (3)..(3)
<223> OTHER INFORMATION: X=any amino acid residue except P

<400> SEQUENCE: 72

Leu Ala Xaa Thr
1

<210> SEQ ID NO 73
<211> LENGTH: 4
<212> TYPE: PRT
<213> ORGANISM: Artificial Sequence
<220> FEATURE:
<223> OTHER INFORMATION: sortase recognition motif
<220> FEATURE:
<221> NAME/KEY: MISC_FEATURE
<222> LOCATION: (3)..(3)
<223> OTHER INFORMATION: X=any amino acid residue except P

<400> SEQUENCE: 73

Leu Ser Xaa Thr
1

<210> SEQ ID NO 74
<211> LENGTH: 4
<212> TYPE: PRT
<213> ORGANISM: Artificial Sequence
<220> FEATURE:
<223> OTHER INFORMATION: sortase recognition motif
<220> FEATURE:
<221> NAME/KEY: MISC_FEATURE
<222> LOCATION: (3)..(3)
<223> OTHER INFORMATION: X=any amino acid residue except P

<400> SEQUENCE: 74

Asn Pro Xaa Thr
1

<210> SEQ ID NO 75
<211> LENGTH: 4
<212> TYPE: PRT
<213> ORGANISM: Artificial Sequence
<220> FEATURE:
<223> OTHER INFORMATION: sortase recognition motif
<220> FEATURE:
<221> NAME/KEY: MISC_FEATURE
<222> LOCATION: (3)..(3)
<223> OTHER INFORMATION: X=any amino acid residue except P

<400> SEQUENCE: 75

Val Pro Xaa Thr
1

<210> SEQ ID NO 76
<211> LENGTH: 4
<212> TYPE: PRT
<213> ORGANISM: Artificial Sequence
<220> FEATURE:
<223> OTHER INFORMATION: sortase recognition motif
<220> FEATURE:
<221> NAME/KEY: MISC_FEATURE
<222> LOCATION: (3)..(3)
<223> OTHER INFORMATION: X=any amino acid residue except P

<400> SEQUENCE: 76

Ile Pro Xaa Thr
1

<210> SEQ ID NO 77
<211> LENGTH: 4
<212> TYPE: PRT
<213> ORGANISM: Artificial Sequence
<220> FEATURE:
<223> OTHER INFORMATION: sortase recognition motif
<220> FEATURE:
<221> NAME/KEY: MISC_FEATURE
<222> LOCATION: (3)..(3)
<223> OTHER INFORMATION: X=any amino acid residue except P

<400> SEQUENCE: 77

Leu Gly Xaa Thr
1

<210> SEQ ID NO 78
<211> LENGTH: 4
<212> TYPE: PRT
<213> ORGANISM: Artificial Sequence
<220> FEATURE:
<223> OTHER INFORMATION: sortase recognition motif
<220> FEATURE:

-continued

<221> NAME/KEY: MISC_FEATURE
<222> LOCATION: (3)..(3)
<223> OTHER INFORMATION: X=any amino acid residue except P

<400> SEQUENCE: 78

Tyr Pro Xaa Arg
1

<210> SEQ ID NO 79
<211> LENGTH: 4
<212> TYPE: PRT
<213> ORGANISM: Artificial Sequence
<220> FEATURE:
<223> OTHER INFORMATION: sortase recognition motif

<400> SEQUENCE: 79

Leu Pro Ser Thr
1

<210> SEQ ID NO 80
<211> LENGTH: 4
<212> TYPE: PRT
<213> ORGANISM: Artificial Sequence
<220> FEATURE:
<223> OTHER INFORMATION: sortase recognition motif

<400> SEQUENCE: 80

Leu Pro Lys Thr
1

<210> SEQ ID NO 81
<211> LENGTH: 4
<212> TYPE: PRT
<213> ORGANISM: Artificial Sequence
<220> FEATURE:
<223> OTHER INFORMATION: sortase recognition motif

<400> SEQUENCE: 81

Leu Pro Ile Thr
1

<210> SEQ ID NO 82
<211> LENGTH: 4
<212> TYPE: PRT
<213> ORGANISM: Artificial Sequence
<220> FEATURE:
<223> OTHER INFORMATION: sortase recognition motif

<400> SEQUENCE: 82

Leu Pro Asp Thr
1

<210> SEQ ID NO 83
<211> LENGTH: 4
<212> TYPE: PRT
<213> ORGANISM: Artificial Sequence
<220> FEATURE:
<223> OTHER INFORMATION: sortase recognition motif

<400> SEQUENCE: 83

Ser Pro Lys Thr
1

<210> SEQ ID NO 84
<211> LENGTH: 4
<212> TYPE: PRT
<213> ORGANISM: Artificial Sequence

```
<220> FEATURE:
<223> OTHER INFORMATION: sortase recognition motif

<400> SEQUENCE: 84

Leu Ala Glu Thr
1

<210> SEQ ID NO 85
<211> LENGTH: 4
<212> TYPE: PRT
<213> ORGANISM: Artificial Sequence
<220> FEATURE:
<223> OTHER INFORMATION: sortase recognition motif

<400> SEQUENCE: 85

Leu Ala Ala Thr
1

<210> SEQ ID NO 86
<211> LENGTH: 4
<212> TYPE: PRT
<213> ORGANISM: Artificial Sequence
<220> FEATURE:
<223> OTHER INFORMATION: sortase recognition motif

<400> SEQUENCE: 86

Leu Ala Ser Thr
1

<210> SEQ ID NO 87
<211> LENGTH: 4
<212> TYPE: PRT
<213> ORGANISM: Artificial Sequence
<220> FEATURE:
<223> OTHER INFORMATION: sortase recognition motif

<400> SEQUENCE: 87

Leu Pro Leu Thr
1

<210> SEQ ID NO 88
<211> LENGTH: 4
<212> TYPE: PRT
<213> ORGANISM: Artificial Sequence
<220> FEATURE:
<223> OTHER INFORMATION: sortase recognition motif

<400> SEQUENCE: 88

Leu Ser Arg Thr
1

<210> SEQ ID NO 89
<211> LENGTH: 4
<212> TYPE: PRT
<213> ORGANISM: Artificial Sequence
<220> FEATURE:
<223> OTHER INFORMATION: sortase recognition motif

<400> SEQUENCE: 89

Leu Pro Glu Thr
1

<210> SEQ ID NO 90
<211> LENGTH: 4
<212> TYPE: PRT
<213> ORGANISM: Artificial Sequence
<220> FEATURE:
```

```
<223> OTHER INFORMATION: sortase recognition motif

<400> SEQUENCE: 90

Val Pro Asp Thr
1

<210> SEQ ID NO 91
<211> LENGTH: 4
<212> TYPE: PRT
<213> ORGANISM: Artificial Sequence
<220> FEATURE:
<223> OTHER INFORMATION: sortase recognition motif

<400> SEQUENCE: 91

Ile Pro Gln Thr
1

<210> SEQ ID NO 92
<211> LENGTH: 4
<212> TYPE: PRT
<213> ORGANISM: Artificial Sequence
<220> FEATURE:
<223> OTHER INFORMATION: sortase recognition motif

<400> SEQUENCE: 92

Tyr Pro Arg Arg
1

<210> SEQ ID NO 93
<211> LENGTH: 4
<212> TYPE: PRT
<213> ORGANISM: Artificial Sequence
<220> FEATURE:
<223> OTHER INFORMATION: sortase recognition motif

<400> SEQUENCE: 93

Leu Pro Met Thr
1

<210> SEQ ID NO 94
<211> LENGTH: 4
<212> TYPE: PRT
<213> ORGANISM: Artificial Sequence
<220> FEATURE:
<223> OTHER INFORMATION: sortase recognition motif

<400> SEQUENCE: 94

Leu Ala Phe Thr
1

<210> SEQ ID NO 95
<211> LENGTH: 4
<212> TYPE: PRT
<213> ORGANISM: Artificial Sequence
<220> FEATURE:
<223> OTHER INFORMATION: sortase recognition motif

<400> SEQUENCE: 95

Leu Pro Gln Thr
1

<210> SEQ ID NO 96
<211> LENGTH: 4
<212> TYPE: PRT
<213> ORGANISM: Artificial Sequence
<220> FEATURE:
<223> OTHER INFORMATION: sortase recognition motif
```

```
<220> FEATURE:
<221> NAME/KEY: MISC_FEATURE
<222> LOCATION: (1)..(1)
<223> OTHER INFORMATION: X= L or I or V or M
<220> FEATURE:
<221> NAME/KEY: MISC_FEATURE
<222> LOCATION: (3)..(3)
<223> OTHER INFORMATION: X=any amino acid residue except P
<220> FEATURE:
<221> NAME/KEY: MISC_FEATURE
<222> LOCATION: (4)..(4)
<223> OTHER INFORMATION: X=T or S or A

<400> SEQUENCE: 96

Xaa Pro Xaa Xaa
1

<210> SEQ ID NO 97
<211> LENGTH: 5
<212> TYPE: PRT
<213> ORGANISM: Artificial Sequence
<220> FEATURE:
<223> OTHER INFORMATION: sortase recognition motif

<400> SEQUENCE: 97

Tyr Pro Pro Arg Gly
1               5

<210> SEQ ID NO 98
<211> LENGTH: 5
<212> TYPE: PRT
<213> ORGANISM: Artificial Sequence
<220> FEATURE:
<223> OTHER INFORMATION: sortase recognition motif

<400> SEQUENCE: 98

Leu Ala Phe Thr Gly
1               5

<210> SEQ ID NO 99
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: MISC_FEATURE
<222> LOCATION: (3)..(3)
<223> OTHER INFORMATION: X=any amino acid residue except P

<400> SEQUENCE: 99

Leu Pro Xaa Ala Gly
1               5

<210> SEQ ID NO 100
<211> LENGTH: 5
<212> TYPE: PRT
<213> ORGANISM: Artificial Sequence
<220> FEATURE:
<223> OTHER INFORMATION: sortase recognition motif

<400> SEQUENCE: 100

Leu Pro Asn Ala Gly
1               5

<210> SEQ ID NO 101
<211> LENGTH: 5
<212> TYPE: PRT
<213> ORGANISM: Artificial Sequence
```

```
<220> FEATURE:
<223> OTHER INFORMATION: sortase recognition motif
<220> FEATURE:
<221> NAME/KEY: MISC_FEATURE
<222> LOCATION: (3)..(3)
<223> OTHER INFORMATION: X=any amino acid residue except P

<400> SEQUENCE: 101

Leu Pro Xaa Thr Ala
1               5

<210> SEQ ID NO 102
<211> LENGTH: 5
<212> TYPE: PRT
<213> ORGANISM: Artificial Sequence
<220> FEATURE:
<223> OTHER INFORMATION: sortase recognition motif

<400> SEQUENCE: 102

Leu Pro Asn Thr Ala
1               5

<210> SEQ ID NO 103
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: MISC_FEATURE
<222> LOCATION: (3)..(3)
<223> OTHER INFORMATION: X=any amino acid residue except P

<400> SEQUENCE: 103

Leu Gly Xaa Thr Gly
1               5

<210> SEQ ID NO 104
<211> LENGTH: 5
<212> TYPE: PRT
<213> ORGANISM: Artificial Sequence
<220> FEATURE:
<223> OTHER INFORMATION: sortase recognition motif

<400> SEQUENCE: 104

Leu Gly Ala Thr Gly
1               5

<210> SEQ ID NO 105
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: MISC_FEATURE
<222> LOCATION: (3)..(3)
<223> OTHER INFORMATION: X=any amino acid residue except P

<400> SEQUENCE: 105

Ile Pro Xaa Thr Gly
1               5

<210> SEQ ID NO 106
<211> LENGTH: 5
<212> TYPE: PRT
<213> ORGANISM: Artificial Sequence
<220> FEATURE:
<223> OTHER INFORMATION: sortase recognition motif
```

```
<400> SEQUENCE: 106

Ile Pro Asn Thr Gly
1               5

<210> SEQ ID NO 107
<211> LENGTH: 5
<212> TYPE: PRT
<213> ORGANISM: Artificial Sequence
<220> FEATURE:
<223> OTHER INFORMATION: sortase recognition motif

<400> SEQUENCE: 107

Ile Pro Glu Thr Gly
1               5

<210> SEQ ID NO 108
<211> LENGTH: 5
<212> TYPE: PRT
<213> ORGANISM: Artificial Sequence
<220> FEATURE:
<223> OTHER INFORMATION: sortase recognition motif

<400> SEQUENCE: 108

Leu Pro Glu Thr Ala
1               5

<210> SEQ ID NO 109
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: MISC_FEATURE
<222> LOCATION: (3)..(3)
<223> OTHER INFORMATION: X=D, E, A, N, Q, K, R
<220> FEATURE:
<221> NAME/KEY: MISC_FEATURE
<222> LOCATION: (5)..(5)
<223> OTHER INFORMATION: X=A,G

<400> SEQUENCE: 109

Leu Pro Xaa Thr Xaa
1               5

<210> SEQ ID NO 110
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: MISC_FEATURE
<222> LOCATION: (3)..(3)
<223> OTHER INFORMATION: X=D, E, A, N, Q, K, R

<400> SEQUENCE: 110

Leu Pro Xaa Thr Ala
1               5

<210> SEQ ID NO 111
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: MISC_FEATURE
```

```
<222> LOCATION: (3)..(3)
<223> OTHER INFORMATION: X=D, E, A, N, Q, K, R

<400> SEQUENCE: 111

Leu Pro Xaa Thr Gly
1               5

<210> SEQ ID NO 112
<211> LENGTH: 85
<212> TYPE: PRT
<213> ORGANISM: Streptomyces coelicolor

<400> SEQUENCE: 112

Val Ala Gly His Val Asp Asn Ala Glu Gly Pro Ala Val Phe Tyr Arg
1               5                   10                  15

Leu Gly Ala Leu Glu Lys Gly Ser Ala Ile Glu Ile Asp Arg Arg Asp
            20                  25                  30

Gly Gly Val Ala Val Phe Thr Val Asp Ala Val Glu Val Tyr Ala Ala
        35                  40                  45

Asp Ala Phe Pro Asp Glu Lys Val Tyr Gly Ala Asp Arg Pro Glu
    50                  55                  60

Leu Arg Val Ile Thr Cys Gly Pro Tyr Ser Arg Ser Thr Gly Tyr
65                  70                  75                  80

Gln Gly Asn Val Val
                85

<210> SEQ ID NO 113
<211> LENGTH: 85
<212> TYPE: PRT
<213> ORGANISM: Streptomyces coelicolor

<400> SEQUENCE: 113

Val Val Gly His Val Asp Asn Gln Gln Gly Pro Ala Val Phe Tyr Gly
1               5                   10                  15

Leu Gly Ala Leu Lys Lys Gly Asn Lys Val Glu Val His Arg Gln Asp
            20                  25                  30

Gly Lys Thr Ala Val Phe Glu Ile Tyr Gly Ile Glu Val Phe Glu Lys
        35                  40                  45

Asn Asn Phe Pro Gly Asp Arg Val Tyr Gly Ser Lys Gly Ser Pro Glu
    50                  55                  60

Leu Arg Val Ile Thr Cys Gly Gly Gly Phe Thr Lys Gln Asn Gly Tyr
65                  70                  75                  80

Asp Gly Asn Val Val
                85

<210> SEQ ID NO 114
<211> LENGTH: 86
<212> TYPE: PRT
<213> ORGANISM: Streptomyces coelicolor

<400> SEQUENCE: 114

Ile Ala Gly His Val Asp Thr Lys Thr Ser Ala Ala Val Phe Ala Arg
1               5                   10                  15

Leu Asp Gln Leu Asp Lys Gly Asp Lys Phe Gln Val Arg Arg Ala Asp
            20                  25                  30

Gly Arg Ser Ala Thr Phe Val Val Asp Gly Leu Glu Thr Phe Ala Lys
        35                  40                  45

Asp Glu Phe Pro Ser Asp Arg Val Tyr Gly Asp Ala Asp Arg Pro Glu
    50                  55                  60
```

Val Arg Leu Ile Thr Cys Ala Gly Asp Tyr Asp His Lys Val Lys Asp
65                  70                  75                  80

Tyr Thr Asp Asn Leu Val
                85

<210> SEQ ID NO 115
<211> LENGTH: 88
<212> TYPE: PRT
<213> ORGANISM: Streptomyces coelicolor

<400> SEQUENCE: 115

Met Val Gly His Val Asp Thr Glu Thr Arg Pro Ala Val Phe Tyr Gln
1               5                   10                  15

Leu Ser Thr Leu Glu Pro Gly Gln Thr Ile Arg Val Ala Arg Asp Asp
                20                  25                  30

Asp Glu Val Ala Glu Phe Thr Val Asp Asp Val Gln Val Leu Thr Arg
            35                  40                  45

Asp Gly Phe Asp Ala Gln Gln Ala Tyr Gly Pro Arg Asp Thr Gly Arg
        50                  55                  60

Ser Glu Leu Arg Leu Ile Thr Cys Gly Gly Thr Phe Asp Gln Thr Thr
65                  70                  75                  80

Asp Ser Tyr Thr Ala Asn Val Val
                85

<210> SEQ ID NO 116
<211> LENGTH: 78
<212> TYPE: PRT
<213> ORGANISM: Bacillus halodurans

<400> SEQUENCE: 116

Leu Ser Gly His Arg Asp Thr Val Phe Arg Asp Met Gly Lys Leu Glu
1               5                   10                  15

Ile Gly Asp Asp Leu Thr Val His Met Pro Tyr Gly Ser Tyr Thr Tyr
                20                  25                  30

Arg Ile Val Asp Thr Glu Ile Val Asp Ala Asn Asp Thr Ser Val Ile
            35                  40                  45

Arg Ser Thr Ala Pro Asp Glu Val Leu Thr Leu Ser Thr Cys Tyr Pro
        50                  55                  60

Phe Asn Phe Ile Gly Ser Ala Pro Glu Arg Tyr Ile Ile Tyr
65                  70                  75

<210> SEQ ID NO 117
<211> LENGTH: 78
<212> TYPE: PRT
<213> ORGANISM: Bacillus subtilis

<400> SEQUENCE: 117

Leu Ser Gly His Arg Asp Thr Val Phe Arg Arg Thr Gly Glu Leu Glu
1               5                   10                  15

Lys Gly Asp Gln Leu Arg Leu Leu Ser Tyr Gly Glu Phe Thr Tyr
                20                  25                  30

Glu Ile Val Lys Thr Lys Ile Val Asp Lys Asp Asp Thr Ser Ile Ile
            35                  40                  45

Thr Leu Gln His Glu Lys Glu Glu Leu Ile Leu Thr Thr Cys Tyr Pro
        50                  55                  60

Phe Ser Tyr Val Gly Asn Ala Pro Lys Arg Tyr Ile Ile Tyr
65                  70                  75

<210> SEQ ID NO 118
<211> LENGTH: 77
<212> TYPE: PRT
<213> ORGANISM: Bacillus halodurans

<400> SEQUENCE: 118

Leu Ser Gly His Arg Asp Thr Val Phe Arg Glu Leu Gly Glu Val Gly
1               5                   10                  15

Val Gly Asp Leu Leu Ile Val Glu Thr Ala Thr Gly Thr His Thr Tyr
            20                  25                  30

Arg Val Arg Lys Val Arg Ile Val Asp Glu Asp Arg Thr Val Ile
        35                  40                  45

Val Pro Lys Pro Arg Ala Thr Leu Thr Val Ser Thr Cys Tyr Pro Phe
    50                  55                  60

Asp Phe Ile Gly Ser Ala Pro Glu Arg Tyr Ile Leu Glu
65                  70                  75

<210> SEQ ID NO 119
<211> LENGTH: 77
<212> TYPE: PRT
<213> ORGANISM: Bacillus anthracis

<400> SEQUENCE: 119

Leu Ser Gly His Arg Asp Thr Val Phe Thr Asp Leu Gly Gln Leu Lys
1               5                   10                  15

Glu Lys Asp Thr Leu Val Leu Glu Tyr Asp Asn Lys Thr Tyr Thr Tyr
20 25 30

Glu Ile Gln Lys Ile Trp Ile Thr His Ala Asp Asp Arg Thr Val Ile
35 40 45

Ile Lys Lys Glu Glu Pro Ile Leu Thr Leu Thr Thr Cys Tyr Pro Phe
50 55 60

Asp Tyr Leu Gly Asp Ala Pro Asp Arg Tyr Leu Ile Asx
65 70 75

<210> SEQ ID NO 120
<211> LENGTH: 81
<212> TYPE: PRT
<213> ORGANISM: Bacillus halodurans

<400> SEQUENCE: 120

Ile Ala Ala His Arg Ser Arg Thr Tyr Gly Arg Gln Pro Asn Arg Leu
1 5 10 15

Asp Glu Val Glu Gly Asp Val Ile Thr Val Thr Thr Asn Asn His Met
20 25 30

Tyr Arg Tyr Thr Val Tyr Ser Ile Thr Val Val Glu Pro Thr Asn Ile
35 40 45

Asp Ile Leu Gln His Asp Gly Thr Ala Pro Val Leu Thr Leu Leu Thr
50 55 60

Cys Asp Pro Val Lys Asp Pro Thr His Arg Leu Ile Val Gln Ala Glu
65 70 75 80

Met

<210> SEQ ID NO 121
<211> LENGTH: 81
<212> TYPE: PRT
<213> ORGANISM: Clostridium acetobutylicum

<400> SEQUENCE: 121

```
Leu Ala Gly His Arg Ser Tyr Thr Phe Gly Glu Tyr Phe Asn Arg Leu
1               5                   10                  15

Gly Glu Ile Gly Ser Gly Asp Glu Ile Asp Val Glu Thr Val Asn Gly
            20                  25                  30

Thr Phe Lys Tyr Lys Val Tyr Ser Thr Lys Val Val Leu Pro Ser Glu
                35                  40                  45

Val His Val Leu Asp Gln Thr Lys Asp Pro Thr Met Thr Leu Val Thr
        50                  55                  60

Cys Thr Pro Ile Arg Ile Ala Thr His Arg Leu Ile Ile Lys Ala Lys
65                  70                  75                  80

Arg
```

```
<210> SEQ ID NO 122
<211> LENGTH: 89
<212> TYPE: PRT
<213> ORGANISM: Streptomyces coelicolor

<400> SEQUENCE: 122

Leu Ala Gly His Arg Asn Thr His Gly Glu Pro Phe Arg Tyr Ile Asn
1               5                   10                  15

Lys Leu Glu Pro Gly Asp Pro Ile Val Val Thr Gln Asp Lys Tyr
            20                  25                  30

Phe Val Tyr Lys Met Ala Ser Ile Leu Pro Val Thr Ser Pro Ser Asn
                35                  40                  45

Val Ser Val Leu Asp Pro Val Pro Lys Gln Ser Gly Phe Lys Gly Pro
        50                  55                  60

Gly Arg Tyr Ile Thr Leu Thr Thr Cys Thr Pro Glu Phe Thr Ser Lys
65                  70                  75                  80

Tyr Arg Met Ile Val Asn Gly Lys Met
                85
```

```
<210> SEQ ID NO 123
<211> LENGTH: 89
<212> TYPE: PRT
<213> ORGANISM: Streptomyces coelicolor

<400> SEQUENCE: 123

Leu Ala Ala His Arg Asp Gly His Gly Ala Arg Phe His Asn Ile Asp
1               5                   10                  15

Lys Ile Glu Lys Gly Asp Pro Ile Val Phe Glu Thr Lys Asp Thr Trp
            20                  25                  30

Tyr Val Tyr Lys Thr Tyr Ala Val Leu Pro Glu Thr Ser Lys Tyr Asn
                35                  40                  45

Val Glu Val Leu Gly Gly Ile Pro Lys Glu Ser Gly Lys Lys Ala
        50                  55                  60

Gly His Tyr Ile Thr Leu Thr Thr Cys Thr Pro Val Tyr Thr Ser Arg
65                  70                  75                  80

Tyr Arg Tyr Val Val Trp Gly Glu Leu
                85
```

```
<210> SEQ ID NO 124
<211> LENGTH: 81
<212> TYPE: PRT
<213> ORGANISM: Actinomyces naeslundii

<400> SEQUENCE: 124

Ile Thr Gly His Arg Gly Leu Ala Glu Ala Thr Met Phe Thr Asn Leu
1               5                   10                  15
```

```
Asp Lys Val Thr Gly Asp Ser Leu Ile Val Glu Val Phe Gly Glu Val
            20                  25                  30

Leu Thr Tyr Arg Val Thr Ser Thr Lys Val Val Glu Pro Glu Glu Thr
        35                  40                  45

Glu Ala Leu Arg Val Glu Glu Gly Lys Asp Leu Leu Thr Leu Val Thr
 50                  55                  60

Cys Ile Pro Leu Gly Ile Asn Thr His Arg Ile Leu Leu Thr Gly Glu
 65                  70                  75                  80

Arg
```

<210> SEQ ID NO 125
<211> LENGTH: 81
<212> TYPE: PRT
<213> ORGANISM: Corynebacterium diphtheriae

<400> SEQUENCE: 125

```
Ile Thr Ala His Arg Gly Leu Ala Glu Ala Thr Met Phe Thr Asn Leu
  1               5                  10                  15

Asn Lys Val Gly Val Gly Asp Arg Phe Thr Ile Glu Trp Gly Glu Val
            20                  25                  30

Leu Thr Ile Glu Val Arg Glu Thr Arg Val Val Ser Pro Glu Asp Thr
        35                  40                  45

Arg Phe Leu Gln Thr Gln Asp Asp Arg Asp Leu Val Ile Leu Val Thr
 50                  55                  60

Cys Leu Pro Leu Gly Ile Asn Thr His Arg Ile Leu Val Thr Ala Glu
 65                  70                  75                  80

Arg
```

<210> SEQ ID NO 126
<211> LENGTH: 82
<212> TYPE: PRT
<213> ORGANISM: Streptococcus pneumoniae

<400> SEQUENCE: 126

```
Ile Thr Ala Pro Thr Gly Leu Pro Thr Ala Lys Met Phe Thr Asp Leu
  1               5                  10                  15

Thr Lys Leu Lys Val Gly Asp Lys Phe Tyr Val His Asn Ile Lys Glu
            20                  25                  30

Val Met Ala Tyr Gln Val Asp Gln Val Lys Val Ile Glu Pro Thr Asn
        35                  40                  45

Phe Asp Asp Leu Leu Ile Val Pro Gly His Asp Tyr Val Thr Leu Leu
 50                  55                  60

Thr Cys Thr Pro Tyr Met Ile Asn Thr His Arg Leu Leu Val Arg Gly
 65                  70                  75                  80

His Arg
```

<210> SEQ ID NO 127
<211> LENGTH: 82
<212> TYPE: PRT
<213> ORGANISM: Streptococcus pneumoniae

<400> SEQUENCE: 127

```
Ile Thr His Ala Arg Gly Leu Pro Thr Ala Glu Leu Phe Ser Gln Leu
  1               5                  10                  15

Asp Lys Met Lys Lys Gly Asp Ile Phe Tyr Leu His Val Leu Asp Gln
            20                  25                  30
```

```
Val Leu Ala Tyr Gln Val Asp Gln Ile Val Thr Val Glu Pro Asn Asp
            35                  40                  45

Phe Glu Val Leu Ile Gln His Gly Glu Asp Ala Tyr Ala Thr Leu Leu
 50                      55                  60

Thr Cys Thr Pro Tyr Met Ile Asn Ser His Arg Leu Leu Val Arg Gly
 65                  70                  75                  80

Lys Arg

<210> SEQ ID NO 128
<211> LENGTH: 83
<212> TYPE: PRT
<213> ORGANISM: Enterococcus faecalis

<400> SEQUENCE: 128

Ile Ser Ser Gly His Arg Gly Leu Pro Gln Ala Lys Leu Phe Thr Asp
  1               5                  10                  15

Leu Pro Glu Leu Lys Lys Gly Asp Glu Phe Tyr Ile Glu Val Asn Gly
             20                  25                  30

Lys Thr Leu Ala Tyr Gln Val Asp Gln Ile Lys Thr Val Glu Pro Thr
            35                  40                  45

Asp Thr Lys Asp Leu His Ile Glu Ser Gly Gln Asp Leu Val Thr Leu
 50                      55                  60

Leu Glu Cys Thr Pro Tyr Met Ile Asn Ser His Arg Leu Leu Val Arg
 65                  70                  75                  80

Gly His Arg

<210> SEQ ID NO 129
<211> LENGTH: 80
<212> TYPE: PRT
<213> ORGANISM: Streptococcus equinus

<400> SEQUENCE: 129

Ile Ser Gly His Arg Gly Leu Pro Ser Ala Lys Leu Phe Thr Asn Ile
  1               5                  10                  15

Asp Lys Leu Arg Ile Asn Asp Thr Phe Thr Thr Ser Leu Asn Arg Thr
             20                  25                  30

Met Thr Tyr Gln Ile Asp Lys Ala Thr Val Leu Pro Asp Asp Val Ser
            35                  40                  45

Leu Leu Arg Ile Glu Gly Lys Asp Leu Val Thr Leu Val Thr Cys
 50                      55                  60

Thr Pro Tyr Gly Val Asn Thr His Arg Leu Leu Val Arg Gly His Arg
 65                  70                  75                  80

<210> SEQ ID NO 130
<211> LENGTH: 80
<212> TYPE: PRT
<213> ORGANISM: Streptococcus pyogenes

<400> SEQUENCE: 130

Ile Ser Ala Asn Arg Gly Leu Pro Ala Glu Met Phe Thr Asn Leu Asn
  1               5                  10                  15

Leu Val Lys Lys Gly Asp Thr Phe Tyr Phe Arg Val Leu Asn Lys Val
             20                  25                  30

Leu Ala Tyr Lys Val Asp Gln Ile Leu Thr Thr Val Glu Pro Asp Gln
            35                  40                  45

Asn Ser Leu Ser Gln Val Met Gly Lys Asp Ala Thr Leu Val Thr Cys
 50                      55                  60
```

```
Thr Pro Tyr Gly Val Asn Thr Lys Arg Leu Leu Val Arg Gly His Arg
65                  70                  75                  80

<210> SEQ ID NO 131
<211> LENGTH: 81
<212> TYPE: PRT
<213> ORGANISM: Corynebacterium diphtheriae

<400> SEQUENCE: 131

Ile Thr Gly His Ser Gly Leu Ala Asn Ala Thr Leu Phe Asp Leu Glu
1               5                   10                  15

Asp Val Lys Ser His Asp Pro Ile Tyr Ile Thr Val Gln Gly Glu Thr
            20                  25                  30

Leu Lys Tyr Glu Val Asp Ala Ile Asn Val Val Leu Pro Glu Asp Thr
        35                  40                  45

Lys Leu Leu Ala Pro Asp Pro Asn Lys Asp Gln Ile Thr Leu Ile Thr
    50                  55                  60

Cys Thr Phe Tyr Ala Val Asn Ser His Arg Leu Leu Val Arg Ala His
65                  70                  75                  80

Arg

<210> SEQ ID NO 132
<211> LENGTH: 82
<212> TYPE: PRT
<213> ORGANISM: Corynebacterium diphtheriae

<400> SEQUENCE: 132

Ile Thr Gly His Thr Gly Leu Ala Asn Ser Ile Met Phe Asp His Leu
1               5                   10                  15

Asn Tyr Ala Glu Lys Gly Asp Ile Phe Tyr Val Gln Val Ser Gly Glu
            20                  25                  30

Lys Leu Lys Tyr Val Val Asp Gln Ile Lys Val Val Leu Pro Thr Glu
        35                  40                  45

Thr Glu Asp Leu Arg Pro Glu Gln Gly Lys Asp Tyr Ile Leu Leu Ile
    50                  55                  60

Thr Cys Thr Pro Tyr Gly Ile Asn Thr His Arg Leu Met Val Arg Gly
65                  70                  75                  80

His Gln

<210> SEQ ID NO 133
<211> LENGTH: 80
<212> TYPE: PRT
<213> ORGANISM: Corynebacterium diphtheriae

<400> SEQUENCE: 133

Leu Ser Ala His Thr Gly Leu Gln Asn Ala Thr Leu Trp Asp Asn Leu
1               5                   10                  15

Ile Gln Ile Lys Lys Gly Asp Pro Val Tyr Val Ala Ala Gly Glu Lys
            20                  25                  30

Leu Lys Tyr Glu Val Arg Asn Ile Glu Val Val Thr Pro Asp Lys Thr
        35                  40                  45

Ser Leu Leu Arg Arg Thr Ser Asn Lys Asp Gln Val Thr Leu Ile Thr
    50                  55                  60

Cys Thr Pro Tyr Gly Ile Asn Thr His Arg Leu Ile Ile Ala Glu Arg
65                  70                  75                  80

<210> SEQ ID NO 134
<211> LENGTH: 81
```

```
<212> TYPE: PRT
<213> ORGANISM: Corynebacterium diphtheriae

<400> SEQUENCE: 134

Leu Thr Ala His Ser Gly Glu Gln Lys Ser Thr Phe Phe Asp Asn Leu
1               5                   10                  15

Glu Lys Val Lys Gly Asp Ala Ile Tyr Val Arg Asn Ile Gly Glu
            20                  25                  30

Thr Leu Lys Tyr Gln Val Arg Asp Ile Glu Ile Arg Pro Ala Glu
        35                  40                  45

Glu Ile Asp Arg Ile Gln Phe Pro Asp Arg Asp Leu Ile Thr Leu Val
    50                  55                  60

Glu Cys Pro Tyr Gly Ile Asn Thr His Arg Leu Leu Val Thr Ala Glu
65                  70                  75                  80

Arg

<210> SEQ ID NO 135
<211> LENGTH: 74
<212> TYPE: PRT
<213> ORGANISM: Bacillus halodurans

<400> SEQUENCE: 135

Ile Ala Gly His Arg Gly Tyr Arg Gly Asn Arg His Phe Ser Arg Leu
1               5                   10                  15

Pro Asp Val Thr Ile Gly Asp Glu Val Phe Leu His Thr Lys Glu Thr
            20                  25                  30

Phe Asp Ile Ser Ile Ile Glu Pro Thr Asp Val Asp Val Leu Asp Asp
        35                  40                  45

Arg Asp Gly Lys His Glu Ile Thr Met Ile Thr Cys Thr Arg Ser Gly
    50                  55                  60

Lys Gln Arg Val Ala Val Arg Gly Glu Leu
65                  70

<210> SEQ ID NO 136
<211> LENGTH: 80
<212> TYPE: PRT
<213> ORGANISM: Bacillus halodurans

<400> SEQUENCE: 136

Ile Ala Gly His Arg Gly Tyr Arg Gly Asn Arg His Phe Ser Arg Leu
1               5                   10                  15

Pro Asp Val Thr Ile Gly Asp Glu Val Phe Leu His Thr Lys Glu Glu
            20                  25                  30

Thr Phe Val Tyr Lys Val Thr Asp Ile Ser Ile Ile Glu Pro Thr Asp
        35                  40                  45

Val Asp Ile Leu Asp Asp Arg Asp Gly Lys His Glu Ile Thr Met Ile
    50                  55                  60

Thr Cys Thr Arg Ser Gly Lys Gln Arg Val Ala Val Arg Gly Val Leu
65                  70                  75                  80

<210> SEQ ID NO 137
<211> LENGTH: 85
<212> TYPE: PRT
<213> ORGANISM: Streptococcus mutans

<400> SEQUENCE: 137

Leu Ala Ser His His Val Pro Gly Met Thr Gly Ser Ser Gln Met Leu
1               5                   10                  15
```

```
Phe Ser Pro Leu Glu Arg Ala Lys Glu Gly Met Glu Ile Tyr Leu Thr
            20                  25                  30

Asp Lys Asn Lys Val Tyr Thr Tyr Val Ile Ser Glu Lys Thr Val Thr
            35                  40                  45

Pro Glu His Val Glu Val Ile Asp Asn Arg Pro Gly Gln Asn Glu Val
            50                  55                  60

Thr Leu Val Thr Cys Thr Asp Ala Gly Ala Thr Ala Arg Thr Ile Val
65                  70                  75                  80

His Gly Thr Tyr Lys
                85
```

<210> SEQ ID NO 138
<211> LENGTH: 88
<212> TYPE: PRT
<213> ORGANISM: Streptococcus pyogenes

<400> SEQUENCE: 138

```
Leu Ala Ser His His Ile Phe Pro Gly Ile Thr Gly Ser Ser Gln Thr
1               5                   10                  15

Phe Leu Phe Ser Pro Leu Glu Arg Ala Gln Asn Gly Met Ser Ile Tyr
            20                  25                  30

Leu Thr Asp Lys Asx Lys Ile Tyr Glu Tyr Ile Ile Lys Asp Val Pro
            35                  40                  45

Ile Val Ala Pro Glu Arg Val Asp Val Ile Asp Thr Ala Gly Leu
            50                  55                  60

Lys Glu Val Leu Val Arg Cys Thr Asp Ile Glu Ala Thr Glu Arg
65                  70                  75                  80

Ile Ile Val Lys Gly Glu Leu Lys
                85
```

<210> SEQ ID NO 139
<211> LENGTH: 85
<212> TYPE: PRT
<213> ORGANISM: Streptococcus pneumoniae

<400> SEQUENCE: 139

```
Leu Ala Ser His His Ile Phe Gly Val Asp Asn Ala Asn Lys Met Leu
1               5                   10                  15

Phe Ser Pro Leu Asp Asn Ala Lys Asn Gly Met Lys Ile Tyr Leu Thr
            20                  25                  30

Asp Lys Asn Lys Val Tyr Thr Tyr Glu Ile Arg Glu Lys Arg Val
            35                  40                  45

Thr Pro Asp Arg Val Asp Glu Val Asp Asp Arg Asp Gly Val Asn Glu
            50                  55                  60

Ile Thr Leu Val Thr Cys Glu Leu Ala Ala Thr Glu Arg Ile Ile Val
65                  70                  75                  80

Lys Gly Asp Leu Lys
                85
```

<210> SEQ ID NO 140
<211> LENGTH: 82
<212> TYPE: PRT
<213> ORGANISM: Enterococcus faecalis

<400> SEQUENCE: 140

```
Leu Ala Ser His Arg Thr Glu Asp Gly Val Ser Leu Phe Ser Pro Leu
1               5                   10                  15

Glu Arg Thr Lys Lys Asp Glu Leu Ile Tyr Ile Thr Asp Leu Ser Thr
```

```
                    20                  25                  30

Val Tyr Thr Tyr Lys Ile Thr Ser Val Glu Lys Ile Glu Pro Thr Arg
                35                  40                  45

Val Glu Leu Ile Asp Asp Val Pro Gly Gln Asn Met Ile Thr Leu Ile
 50                  55                  60

Thr Cys Gly Asp Leu Gln Ala Thr Thr Arg Ile Ala Val Gln Gly Thr
 65                  70                  75                  80

Leu Ala

<210> SEQ ID NO 141
<211> LENGTH: 90
<212> TYPE: PRT
<213> ORGANISM: Bacillus halodurans

<400> SEQUENCE: 141

Asp His His Glu Gly Phe Tyr Tyr Asp Thr Leu Tyr Asn Arg Tyr Asp
 1               5                  10                  15

Val Glu Val Phe Ser Ala Tyr Val Thr Thr Thr Asp Phe Tyr Tyr Ile
                20                  25                  30

Glu Thr Glu Phe Pro Ser Lys Asp Asp Tyr Lys Ala Phe Leu Asn Glu
                35                  40                  45

Leu Lys Lys Arg Ser Val Val Gln Thr Asn Val Glu Val Gly Glu Glu
 50                  55                  60

Asp Gln Ile Ile Thr Leu Ser Thr Cys Asp Tyr Arg Leu Asp Arg Asp
 65                  70                  75                  80

Arg Gly Arg Leu Val Val His Gly Lys Leu
                85                  90

<210> SEQ ID NO 142
<211> LENGTH: 91
<212> TYPE: PRT
<213> ORGANISM: Bacillus anthracis

<400> SEQUENCE: 142

Phe Met Ser His Arg Lys Leu Tyr Tyr Asp Thr Leu Phe Glu Gly Tyr
 1               5                  10                  15

Asp Leu Glu Val Phe Ser Val Tyr Thr Thr Thr Asp Phe Tyr Tyr
                20                  25                  30

Ile Glu Thr Asp Phe Ser Ser Asp Thr Glu Tyr Thr Ser Phe Leu Glu
                35                  40                  45

Lys Ile Gln Glu Lys Ser Leu Tyr Lys Thr Thr Thr Val Thr Ala
 50                  55                  60

Gly Asp Gln Ile Val Thr Leu Ser Thr Cys Asp Tyr Ala Leu Asp Pro
 65                  70                  75                  80

Glu Ala Gly Arg Leu Val Val His Ala Lys Leu
                85                  90

<210> SEQ ID NO 143
<211> LENGTH: 91
<212> TYPE: PRT
<213> ORGANISM: Staphylococcus aureus

<400> SEQUENCE: 143

Tyr Glu Lys His Lys Ile Ile Glu Pro Asp Asn Lys Tyr Gly Lys Tyr
 1               5                  10                  15

Gln Leu Gln Val Tyr Phe Ser Ala Tyr Lys Thr Thr Thr Lys Asp Asn
                20                  25                  30
```

Tyr Ile Arg Thr Asp Phe Glu Asn Asp Gln Asp Tyr Gln Gln Phe Leu
            35                  40                  45

Asp Glu Thr Lys Arg Lys Ser Val Ile Asn Ser Asp Val Asn Val Thr
 50                  55                  60

Val Lys Asp Lys Ile Met Thr Leu Ser Thr Cys Glu Asp Ala Tyr Ser
 65                  70                  75                  80

Thr Thr Lys Arg Ile Val Val Ala Lys Ile
             85                  90

<210> SEQ ID NO 144
<211> LENGTH: 92
<212> TYPE: PRT
<213> ORGANISM: Streptococcus pyogenes

<400> SEQUENCE: 144

Phe Asn Lys His Lys Glu Pro Ser Ile Glu Thr Lys Thr Lys Gln Lys
 1               5                  10                  15

Leu Lys Ile Asn Ile Phe Ala Cys Ile Gln Thr Asp Ala Phe Asp Ser
             20                  25                  30

Leu Leu Phe Asn Pro Ile Asp Val Asp Ile Ser Ser Lys Asn Glu Phe
         35                  40                  45

Leu Thr Asn His Ile Lys Gln Lys Ser Val Gln Tyr Arg Glu Ile Leu
 50                  55                  60

Thr Thr Asn Glu Ser Arg Phe Val Ala Leu Ser Thr Cys Glu Asp Met
 65                  70                  75                  80

Thr Thr Asp Gly Arg Ile Ile Val Ile Gly Gln Ile
             85                  90

<210> SEQ ID NO 145
<211> LENGTH: 91
<212> TYPE: PRT
<213> ORGANISM: Streptococcus pyogenes

<400> SEQUENCE: 145

Phe Asn Lys His Asn Lys Ala Ile Ile Glu Thr Lys Glu Arg Lys Lys
 1               5                  10                  15

Leu Thr Val Thr Ile Phe Ala Cys Leu Lys Thr Asp Ala Phe Asp Gln
             20                  25                  30

Leu Val Phe Asn Pro Asn Ala Ile Thr Asn Gln Asp Gln Gln Lys Gln
         35                  40                  45

Leu Val Asp Tyr Ile Ser Lys Arg Ser Lys Gln Phe Lys Pro Val Lys
 50                  55                  60

Leu Lys His His Thr Lys Phe Val Ala Phe Ser Thr Cys Glu Asn Ser
 65                  70                  75                  80

Thr Asp Asn Arg Val Ile Val Val Gly Thr Ile
             85                  90

<210> SEQ ID NO 146
<211> LENGTH: 81
<212> TYPE: PRT
<213> ORGANISM: Streptococcus pneumoniae

<400> SEQUENCE: 146

Ile Ala Gly His Arg Ala Glu Pro Ser His Val Phe Phe Arg His Leu
 1               5                  10                  15

Asp Gln Leu Lys Val Gly Asp Ala Leu Tyr Tyr Asp Asn Gly Gln Glu
             20                  25                  30

Ile Val Glu Tyr Gln Met Met Asp Thr Glu Ile Ile Leu Pro Ser Glu

```
        35                  40                  45

Trp Glu Lys Leu Glu Ser Val Ser Ser Lys Asn Ile Met Thr Leu Thr
    50                  55                  60

Cys Asp Pro Ile Pro Thr Phe Asn Lys Arg Leu Leu Val Asn Phe Glu
65                  70                  75                  80

Arg

<210> SEQ ID NO 147
<211> LENGTH: 77
<212> TYPE: PRT
<213> ORGANISM: Bacillus anthracis

<400> SEQUENCE: 147

Leu Ala Gly His Asn Met Ser Lys Lys Gly Val Leu Phe Ser Asp Ile
1               5                   10                  15

Ala Ser Leu Lys Lys Gly Asp Lys Ile Tyr Asp Asn Glu Asn Glu Tyr
            20                  25                  30

Glu Tyr Ala Val Thr Gly Val Ser Glu Val Thr Phe Asp Lys Trp Glu
        35                  40                  45

Val Val Glu Asp His Gly Lys Asp Glu Leu Ile Thr Cys Val Ser Val
    50                  55                  60

Lys Asp Asn Ser Lys Arg Tyr Val Val Ala Gly Asp Leu
65                  70                  75

<210> SEQ ID NO 148
<211> LENGTH: 81
<212> TYPE: PRT
<213> ORGANISM: Bacillus subtilis

<400> SEQUENCE: 148

Leu Ala Gly His His Leu Lys Gln Lys Asn Leu Leu Phe Gly Pro Leu
1               5                   10                  15

Glu Asn Ile Lys Thr Gly Ala Gln Ile Val Ile Thr Asp Phe Lys Lys
            20                  25                  30

Asp Tyr Ile Tyr Ser Val Thr Ser Lys Asp Ile Ile Ser Glu Met Asp
        35                  40                  45

Ala Asp Val Val Glu Glu Thr Asn Lys Lys Glu Ile Thr Leu Ile Thr
    50                  55                  60

Cys Asp Lys Ala Val Lys Thr Glu Gly Arg Leu Val Val Lys Gly Glu
65                  70                  75                  80

Leu

<210> SEQ ID NO 149
<211> LENGTH: 81
<212> TYPE: PRT
<213> ORGANISM: Enterococcus faecalis

<400> SEQUENCE: 149

Leu Ala Ser His Asn Ala Gly Tyr Glu Gly Leu Leu Phe Thr Ser Leu
1               5                   10                  15

Asn Lys Val Ser Val Gly Asp Leu Val Lys Leu Asn Asp Arg Gly His
            20                  25                  30

Ser Phe Ile Tyr Lys Val Lys Glu Gln Lys His Val Asp Met Thr Asp
        35                  40                  45

Thr Thr Met Leu Asn Leu Thr Arg Lys Pro Thr Leu Thr Leu Ile Thr
    50                  55                  60

Cys Asp Gln Ala Thr Lys Thr Thr Gly Arg Ile Ile Val Ile Ala Glu
```

Leu

<210> SEQ ID NO 150
<211> LENGTH: 84
<212> TYPE: PRT
<213> ORGANISM: Staphylococcus aureus

<400> SEQUENCE: 150

Ile Ala Gly His Thr Phe Ile Asp Arg Pro Asn Tyr Gln Phe Thr Asn
1               5                   10                  15

Leu Lys Ala Ala Lys Lys Gly Ser Met Val Tyr Phe Lys Val Gly Asn
            20                  25                  30

Glu Thr Arg Lys Tyr Lys Met Thr Ser Ile Arg Asp Val Lys Pro Thr
        35                  40                  45

Asp Val Gly Val Leu Asp Glu Gln Lys Gly Lys Asp Lys Gln Leu Thr
    50                  55                  60

Leu Ile Thr Cys Asp Asp Tyr Asn Glu Lys Thr Gly Val Trp Glu Lys
65                  70                  75                  80

Arg Lys Ile Phe

<210> SEQ ID NO 151
<211> LENGTH: 79
<212> TYPE: PRT
<213> ORGANISM: Shewanella putrefaciens

<400> SEQUENCE: 151

Ile Ala Gly His Arg Asp Thr His Phe Ala Ile Leu Lys Gly Met Thr
1               5                   10                  15

Val Gly Arg Arg Leu Ala Leu Gln Thr Ala Ala Gly Lys Glu Ile Val
            20                  25                  30

Tyr Gln Val Val Ala Thr Lys Glu Ser Gln Thr Glu Leu Met Ala Pro
        35                  40                  45

Ser Asp Asp Asn Arg Leu Thr Leu Ile Thr Cys Tyr Pro Pro Asp Ala
    50                  55                  60

Leu Gln Gly Val Ala Glu Leu Arg Phe Val Val Gln Ala Val Pro
65                  70                  75

<210> SEQ ID NO 152
<211> LENGTH: 91
<212> TYPE: PRT
<213> ORGANISM: Streptomyces coelicolor

<400> SEQUENCE: 152

Val Leu Leu Gly His Val Thr Val Gly Arg Tyr Gly Asp Gly Val Phe
1               5                   10                  15

Arg His Leu Ala Gly Leu Arg Arg Gly Glu Arg Ile Glu Ala Arg Leu
            20                  25                  30

Glu Asn Gly Thr Thr Ala Glu Phe Thr Val Thr Ala Val Arg Thr Val
        35                  40                  45

Ala Lys Ala Asp Phe Pro Thr Asp Val Tyr Gly Asp Val Ala Gly
    50                  55                  60

Pro Glu Leu Arg Leu Ile Thr Cys Gly Gly Pro Arg Asp Gly Gln Glu
65                  70                  75                  80

Tyr Arg Asp Asn Val Ile Val Phe Ala Glu Leu
                85                  90

```
<210> SEQ ID NO 153
<211> LENGTH: 90
<212> TYPE: PRT
<213> ORGANISM: Clostridium difficile

<400> SEQUENCE: 153

Ile Tyr Gly His Asn Met Lys Asn Lys Thr Met Phe Asn Asn Leu Asn
1               5                   10                  15

Lys Phe Lys Asp Ala Asp Phe Phe Lys Lys Asn Asn Lys Ile Lys Ile
            20                  25                  30

Thr Leu Asn Gly Arg Glu Phe Leu Tyr Asp Val Phe Ser Ala Tyr Ile
        35                  40                  45

Val Glu Ser Asp Tyr Asp Tyr Leu Lys Thr Asn Phe Asn Asn Glu Ser
    50                  55                  60

Asp Tyr Gln Asn Tyr Asn Asp Ile Thr Ser Lys Ser Leu Tyr Lys Ser
65                  70                  75                  80

Pro Ile Lys Val Asn Ser Asn Asp Lys Ile
                85                  90

<210> SEQ ID NO 154
<211> LENGTH: 86
<212> TYPE: PRT
<213> ORGANISM: Methanothermobacter thermautotrophicus

<400> SEQUENCE: 154

Ile Leu Gly His Arg Thr Thr Tyr Ser Gly Pro Phe Arg Lys Ile Gly
1               5                   10                  15

Ala Leu Arg Lys Gly Asp Arg Val Ile Ile Glu Asp Ala Ser Ser Ser
            20                  25                  30

Ile Arg Tyr Ile Tyr Thr Val Thr Ser Asn Gly Asp Asp Ile Arg Trp
        35                  40                  45

Asp Tyr Arg Thr Asn Pro Val Arg Phe Ser Gln Ser Gly Asp Ala Arg
    50                  55                  60

Leu Met Leu Ile Thr Cys Tyr Pro Pro Gly Gln Lys Lys Ala Ala Trp
65                  70                  75                  80

Ile Thr His Cys Lys Leu
                85
```

PRODUCTION OF THIOESTERS USING SORTASE

Herein is reported an enzymatic ligation method wherein a first polypeptide comprising a sortase motif and a second polypeptide that has a cysteine residue at its N-terminus are incubated with a sortase A which results in the formation of a thioester between the first and second polypeptide.

BACKGROUND OF THE INVENTION

Sortase A (SrtA) is a membrane bound enzyme which attaches proteins covalently to the bacterial cell wall. The specific recognition motif on the SrtA substrate is LPXTG, whereby the enzyme cleaves between the residues threonine and glycine. The recognition motif on the peptidoglycan is a pentaglycine motif. It has been shown that a triglycine and even a diglycine motif on the N-terminus is sufficient to support the SrtA reaction (Clancy, K. W., et al., Peptide science 94 (2010) 385-396). The reaction proceeds through a thioester acyl-enzyme intermediate, which is resolved by the attack of an amine nucleophile from the oligoglycine, covalently linking peptidoglycan to a protein substrate and regenerating SrtA. SrtA can be used to covalently conjugate chemically synthetized peptides to recombinantly expressed proteins.

In WO 2010/087994 methods for ligation and uses thereof are reported. Recombinant approaches to IgG-like bispecific antibodies are reported by Marvin, J. S., et al. (Acta Pharmacol. Sinica 26 (2005) 649-658). In WO 2013/003555 the use of sortases to install click chemistry handles for protein ligation is reported.

Strijbis, K. et al (Traffic 13 (2012) 780-789) report protein ligation in living cells using sortase. It has been stated by them that the $Ca^{2+}$-dependent *S. aureus* sortase A is not functional intracellularly, but that the $Ca^{2+}$-independent *S. pyogenes* sortase A is functional in the cytosol and endoplasmic reticulum (ER) lumen of both *Saccharomyces cerevisiae* and mammalian HEK293T cells.

Levary, D. A., et al., report protein-protein fusion catalyzed by Sortase A (PLOS ONE 6 (2011)). Engineering of an anti-epidermal growth factor receptor antibody to single chain format and labeling by sortase A-mediated protein ligation is reported by Madej, M. P., et al. (Biotechnol. Bioeng. 109 (2012) 1461-1470). Ta, H. T., et al., report enzymatic single-chain antibody tagging as a universal approach to targeted molecular imaging and cell homing in cardiovascular diseases (Cir. Res. 109 (2011) 365-373). Popp, M., et al., report making and breaking peptide bonds—protein engineering using sortase (Angew. Chem. Int. Ed. Eng. 50 (2011) 5024-5032). Engineered proteins with high affinity for DOTA chelates are reported in WO 2010/099536.

Different efforts to block the revers reactions of Sortase have been reported. Yamamura, Y., et al. (Chem. Commun. 47 (2011) 4742-4744) reported enhancement of sortase A-mediated protein ligation by inducing a beta-hairpin structure around the ligation site by introducing a β-hairpin around the recognition site of the substrate.

Sorting of LPXTG peptides by archetypal sortase A, role of invariant substrate residues in modulating the enzyme dynamics and conformational signature of a productive substrate was reported by Biswas, T., et al. (Biochem. 53 (2014) 2515-2524).

Li, Y. M., et al. report irreversible site-specific hydrazinolysis of proteins by use of Sortase (Angew. Chem. Int. Ed. Engl. 53 (2014) 2198-2202).

A remarkable development in protein conjugation was Native Chemical Ligation (NCL) (Dawson, P. E., et al., Science 266 (1994) 776-779), which allowed the ligation of two unprotected peptides. Prerequisite for NCL is a thioester on the N-terminal peptide. The synthesis of thioester is an elaborate work and additionally thioesters are not stable for long time especially under aquatic conditions. The side specific in situ production of thioesters at C-termini of peptides or even proteins would enhance the power of NCL (Dawson, P. E. and Kent, S. B. Annual review of biochemistry 69 (2000) 923-960; Aimoto, S., Tanpakushitsu kakusan koso. Protein, nucleic acid, enzyme 52 (2007) 1804-1805).

WO 2013/016653 reports methods for detecting the concurrent presence of at least two targets within a biological sample. The method includes contacting said biological sample with a first binding agent, said first binding agent operably linked to a first sortase molecule, wherein said first binding agent specifically binds to a first target; contacting said biological sample with a second binding agent, said second binding agent operably linked to a first sortase recognition sequence peptide, wherein said second binding agent specifically binds to a second target; adding a sortase substrate under conditions where a first sortase-mediated ligation of the sortase substrate to the first sortase recognition sequence will produce a ligation product, and detecting the ligation product, wherein detection of said ligation product indicates the concurrent presence of the first target and the second target in the biological sample.

Sortase-mediated ligations for the site-specific modification of proteins is reported by Schmohl, L. and Schwarzer, D. (Curr. Opin. Chem. Biol. 22 (2014) 122-128). Race, P. R., et al. (J. Biol. Chem. 284 (2009) 6924-6933) reported the crystal structure of *Streptococcus pyogenes* sortase and implications for sortase mechanism.

Ling and co-workers showed the introduction of a thioester comprising group via a sortase (Ling, J. J. J., et al., J. Am. Chem. Soc. 134 (2012) 10749-10752).

SUMMARY OF THE INVENTION

It has been found that sortase A accepts as nucleophile a polypeptide comprising at its N-terminus a cysteine amino acid residue. The resulting enzymatic conjugation product that is released from the enzyme is a thioester, which can undergo a rearrangement thereafter. It has further been found that site specific, in situ generated C-terminal thioester between the sortase motif and the Sortase itself can be used for native chemical ligation (NCL).

One aspect as reported herein is a method for the enzymatic formation/production of a thioester (formation of a new thioester bond between the alpha carboxyl group of an amino acid and the thiol group of a cysteine) comprising the following step incubating
  i) a first polypeptide comprising (optionally within the 100 C-terminal amino acid residues) the amino acid sequence LPXTG (SEQ ID NO: 01, wherein X can be any amino acid residue),
  ii) a second polypeptide that has at its N-terminus a cysteine amino acid residue or is a cysteinyl compound (i.e. a compound that comprises a cysteine amino acid residue with free alpha amino group, e.g. as $NH_2$ or $NH_3^+$, and a carboxy group at position 1, which is part of a peptide bond), and
  iii) a third polypeptide that is a sortase A or a catalytically active fragment thereof (i.e. that has sortase A activity),
and thereby producing a thioester.

In one embodiment the third polypeptide is derived from *Staphylococcus aureus* sortase A or *Listeria monocytogenes* Sortase A.

In one embodiment the method is for the enzymatic conjugation of two polypeptides.

In one embodiment the second polypeptide has at its N-terminus a cysteine amino acid residue followed by one to three glycine or alanine amino acid residues. In one preferred embodiment the second polypeptide has the amino acid sequence CGG, CGGG (SEQ ID NO: 02), CAA or CAAA (SEQ ID NO: 03) at its N-terminus.

In one embodiment the incubating is further in the presence of a thiol additive. In one embodiment the thiol additive is selected from the group consisting of thiophenol, 4-mercaptophenylacetic acid (MPAA), 2-mercaptoethanesulfonate (MESNA) and combinations thereof. In one preferred embodiment the incubating is in the presence of 2-mercaptoethanesulfonate.

In one embodiment the first polypeptide comprises at its C-terminus the amino acid sequence LPXTG (SEQ ID NO: 01, wherein X can be any amino acid residue). In one embodiment the first polypeptide comprises at its C-terminus the amino acid sequence LPETG (SEQ ID NO: 04).

In one embodiment the first polypeptide and the second polypeptide are independently of each other selected from an antibody variable domain, an antibody heavy chain Fab-fragment, an antibody Fc-region, a tag, and a peptide comprising the amino acid sequence LPXTG (SEQ ID NO: 01, wherein X can be any amino acid residue), a linker and a non-sortase motif moiety.

In one embodiment the third polypeptide has the amino acid sequence of SEQ ID NO: 05 or SEQ ID NO: 06.

DETAILED DESCRIPTION OF THE INVENTION

The current invention is based at least in part on the finding that a sortase A accepts as nucleophile a polypeptide that has a cysteine residue at its N-terminus.

I. Definitions

In the present specification and claims the numbering of the residues in an immunoglobulin heavy chain Fc-region is that of the EU index of Kabat (Kabat, E. A., et al., Sequences of Proteins of Immunological Interest, 5th ed., Public Health Service, National Institutes of Health, Bethesda, Md. (1991), NIH Publication 91-3242, expressly incorporated herein by reference).

The term "a cysteinyl compound" denotes a compound that comprises a cysteine amino acid residue with free alpha amino group, e.g. as $NH_2$ or $NH_3^+$, and a carboxy group at position 1 that is in/part of a peptide bond with another moiety, whereby the moiety can be any amino group containing moiety, such as an isolated amino acid residue, a peptide, a polypeptide, a protein, a small molecule, a dye or a (chemical or peptidic) linker.

The term "alteration" denotes the mutation, addition, or deletion of one or more amino acid residues in a parent amino acid sequence, e.g. of an antibody or fusion polypeptide comprising at least an FcRn binding portion of an Fc-region, to obtain a variant antibody or fusion polypeptide.

The term "amino acid mutation" denotes a modification in the amino acid sequence of a parent amino acid sequence. Exemplary modifications include amino acid substitutions, insertions, and/or deletions. In one embodiment the amino acid mutation is a substitution. The term "amino acid mutations at the position" denotes the substitution or deletion of the specified residue, or the insertion of at least one amino acid residue adjacent the specified residue. The term "insertion adjacent to a specified residue" denotes the insertion within one to two residues thereof. The insertion may be N-terminal or C-terminal to the specified residue.

The term "amino acid substitution" denotes the replacement of at least one amino acid residue in a predetermined parent amino acid sequence with a different "replacement" amino acid residue. The replacement residue or residues may be a "naturally occurring amino acid residue" (i.e. encoded by the genetic code) and selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val). In one embodiment the replacement residue is not cysteine. Substitution with one or more non-naturally occurring amino acid residues is also encompassed by the definition of an amino acid substitution herein. A "non-naturally occurring amino acid residue" denotes a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine, alpha-amino isobutyric acid and other amino acid residue analogues such as those described in Ellman, et al., Meth. Enzym. 202 (1991) 301-336. To generate such non-naturally occurring amino acid residues, the procedures of Noren, et al. (Science 244 (1989) 182) and/or Ellman, et al. (supra) can be used. Briefly, these procedures involve chemically activating a suppressor tRNA with a non-naturally occurring amino acid residue followed by in vitro transcription and translation of the RNA. Non-naturally occurring amino acids can also be incorporated into peptides via chemical peptide synthesis and subsequent fusion of these peptides with recombinantly produced polypeptides, such as antibodies or antibody fragments.

The term "amino acid insertion" denotes the incorporation of at least one additional amino acid residue into a predetermined parent amino acid sequence. While the insertion will usually consist of the insertion of one or two amino acid residues, the present application contemplates larger "peptide insertions", e.g. insertion of about three to about five or even up to about ten amino acid residues. The inserted residue(s) may be naturally occurring or non-naturally occurring as defined above.

The term "amino acid deletion" denotes the removal of at least one amino acid residue at a predetermined position in an amino acid sequence.

Within this application whenever an amino acid alteration is mentioned it is a deliberated amino acid alteration and not a random amino acid modification.

The term "tag" denotes a sequence of amino acid residues connected to each other via peptide bonds that has specific binding properties. In one embodiment the tag is an affinity or purification tag. In one embodiment the tag is selected from Arg-tag, His-tag, Flag-tag, 3×Flag-tag, Strep-tag, HA-tag, Nano-tag, SBP-tag, c-myc-tag, S-tag, SNUT-Tag, NusA, T7, thioredoxin, calmodulin-binding-peptide, cellulose-binding-domain, chitin-binding-domain, GST-tag, or MBP-tag (see, e.g., Amau, J., et al., Prot. Expr. Purif. 48 (2006) 1-13).

In one embodiment the tag is selected from SEQ ID NO: 07 (RRRRR), or SEQ ID NO: 08 (RRRRRR), or SEQ ID NO: 09 (HHHHHH), or SEQ ID NO: 10 (KDHLIHNVH-KEFHAHAHNK), or SEQ ID NO: 11 (DYKDDDDK), or SEQ ID NO: 12 (DYKDHDGDYKDHDIDYKDDDDK), or SEQ ID NO: 13 (AWRHPQFGG), or SEQ ID NO: 14 (WSHPQFEK), or SEQ ID NO: 15 (MDVEAWLGAR), or SEQ ID NO: 16 (MDVEAWLGARVPLVET), or SEQ ID NO: 17 (MDEKTTGWRGGHVVEGLAGELEQLRAR-LEHHPQGQREP), or SEQ ID NO: 18 (EQKLISEEDL), or SEQ ID NO: 19 (KETAAAKFERQHMDS), or SEQ ID NO: 20 (KRRWKKNFIAVSAANRFKKISSSGAL), or SEQ ID NO: 21 (cellulose binding domain), or SEQ ID NO: 22 (cellulose binding domain), or SEQ ID NO: 23 (TNPGV-SAWQVNTAYTAGQLVTYNGKTYKCLQPHT-SLAGWEP SNVPALWQLQ), or SEQ ID NO: 24 (GST-tag), or SEQ ID NO: 25 (MBP-tag).

An "effective amount" of an agent, e.g., a pharmaceutical formulation, refers to an amount effective, at dosages and for periods of time necessary, to achieve the desired therapeutic or prophylactic result.

The term "individual" or "subject" denotes a mammal. Mammals include, but are not limited to, domesticated animals (e.g. cows, sheep, cats, dogs, and horses), primates (e.g., humans and non-human primates such as monkeys), rabbits, and rodents (e.g., mice, rats, and hamsters). In certain embodiments, the individual or subject is a human.

The term "pharmaceutical formulation" refers to a preparation which is in such a form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "position" denotes the location of an amino acid residue in the amino acid sequence of a polypeptide. Positions may be numbered sequentially, or according to an established format, for example the EU index of Kabat for antibody numbering.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "sortase A enzymatic activity" as used herein denotes a polypeptide that shows transpeptidation activity in a Reporter immobilization assay (i.e. an assay according to Example 4; and as reported in (WO 2016/096740 incorporated herein by reference).

II. Native Chemical Ligation

The term native chemical ligation (NCL) denotes a synthetic protocol in which a large polypeptide is constructed by the assembly of two or more not-protected small polypeptide fragments, i.e. the reactive groups of the small polypeptides not intended to react in this reaction are not masked by a protection group (see e.g. Kemp, D. S., Biopolymers 20 (1981) 1793-1804; Schnolzer, M. and Kent, S. B., Science 256 (1992) 221-225; Dawson, P. E., et al., Science. 266 (1994) 776-779). NCL is especially useful for the synthesis of polypeptides of 300 amino acid residues or less.

In the hitherto known chemical form of native chemical ligation a first polypeptide comprising an N-terminal free cysteine residue and a second polypeptide comprising a C-terminal thioester are reacted with each other. In the first step of the reaction the thiol group of an N-terminal cysteine residue as a nucleophile attacks the activated carbonyl group carbon atom of the C-terminal thioester whereby an intermolecular thioester is formed. This reaction is generally performed in a buffer aqueous solution at about neutral pH of 7 in the temperature range of from 20° C. to 37° C. This first step is reversible but chemo-as well as regioselective. Due to the steric orientation of the intermolecular thioester an intramolecular S,N-acyl shift is possible. The S,N-acyl shift results in the rearrangement of the thioester bond to a natural amide bond (peptide bond) at the conjugation site of the first and second polypeptide.

The first step of the NCL reaction is reversible, especially in the presence of a free thiol as catalyst. But after the S,N-acyl shift the reaction is no longer reversible.

The NCL reaction can be performed with high yields even if the first and/or second polypeptide comprise further cysteine residues in their respective amino acid sequence (internal cysteine residues). This is due to the S,N-acyl shift based rearrangement of the labile thioester into a stable amide bond (labile and stable refer to neutral pH conditions in the absence of bond breaking reagents). Other functional groups might be present in the first and second polypeptide, such as e.g. acid groups, basic amino groups, or phenolic hydroxyl groups.

The NCL reaction can be catalyzed by thiol additives such as a combination of thiophenol, 4-mercaptophenylacetic acid (MPAA), or 2-mercaptoethanesulfonate (MESNA).

Due to the S,N-acyl shift the primary reaction product is removed from the reaction equilibrium and the reaction generally gives very high yields, frequently even a quantitative conversion of the isolated polypeptides in a conjugate.

The resulting polypeptide comprises a cysteine residue at the site of the ligation. This cysteine residue can be modified to give other amino acid residues, such as e.g. alanine (by desulfurization). Beside cysteine also homo-cysteine, seleno-cysteine and beta-thiol amino acids have been used in NCL reactions.

Compared to other amide bond formation reaction the NCL reaction has the advantages that it does not require that other reactive groups present in the two polypeptides to be ligated have to be masked/protected, that almost exclusively the intended reaction product is formed despite the low molar concentrations which normally result in by-product formation, and that no racemization prone activation of an acyl group has to be performed.

The main drawback of the NCL reaction is the need to provide a not-protected polypeptide with a C-terminal thioester. Such thioesters can be synthesized using a BOC-based approach as the FMOC-based approach requires the use of a nucleophilic base which is not possible if a thioester is to be synthesized. Additionally protective groups that result in the formation of aldehydes or ketones upon their release are also not suitable as the released aldehyde or ketone might react with the N-terminal cysteine residue.

Variants of the native chemical ligation approach (conjugation of modified synthetic polypeptides with recombinantly produced polypeptides) are expressed protein ligation (see e.g. Pellois, J.-P. and Muir, T. W., Curr. Opin. Chem. Biol. 10 (2006) 487; Muir, T. W., et al., Proc. Nat. Acad. Sci. USA 95 (1998) 6705-6710) and intein mediated protein ligation (see e.g. Saleh, L. and Perler, F. B., Chem. Rec. 6 (2006) 183-193; Noren, C. J., et al., Angew. Chem. Int. Ed. 39 (2000) 451-466).

Ling and co-workers showed the introduction of a thioester via a sortase (Ling, J. J. J., et al., J. Am. Chem. Soc. 134 (2012) 10749-10752). They used the normal Sortase reaction with a pentaglycine containing a C-terminal thioester. The resulting product has to be purified before using it for NCL.

III. Enzymatic Conjugation Using Sortase A

A covalent conjugate comprising two in vivo not covalently associated entities can be obtained in vitro by using the enzyme sortase, especially sortase A.

Transamidases in general catalyze the formation of a peptide bond (amide bond) between an acyl donor and a nucleophilic acyl acceptor. In order to form a peptide bond the acyl acceptor has to contain a NH2-CH2-moiety. Gram-positive bacteria include the following genera: *Actinomyces, Bacillus, Bifidobacterium, Cellulomonas, Clostridium, Corynebacterium, Micrococcus, Mycobacterium, Nocardia, Staphylococcus, Streptococcus* and *Streptomyces*.

Sortases have been classified into 4 classes, designated A, B, C, and D, based on sequence alignment and phylogenetic analysis of 61 sortases from gram-positive bacterial genomes (Dramsi, S., et al., Res. Microbiol. 156 (2005) 289-297). These classes correspond to the following subfamilies, into which sortases have also been classified by Comfort and Clubb (Comfort, D. and Clubb, R. T., Infect. Immun. 72 (2004) 2710-2722): Class A (Subfamily 1), Class B (Subfamily 2), Class C (Subfamily 3), Class D (Subfamilies 4 and 5). The aforementioned references disclose numerous sortases and recognition motifs (see also Pallen, M. J., et al., Trends Microbiol. 9 (2001) 97-101). With this information a person skilled in the art can assign a sortase to the correct class based on its sequence and/or other characteristics such as those described in Dramsi (supra).

Sortase A (SrtA) is a membrane bound enzyme has transamidase activity. It has been identified and isolated from gram-positive bacteria. In vivo Sortase A attaches proteins covalently to the bacterial cell wall. The specific recognition motif on the SrtA substrate is LPXTG, whereby the enzyme cleaves between the residues threonine and glycine. The recognition motif on the peptidoglycan is a pentaglycine motif. It has been shown that a triglycine and even a diglycine motif on the N-terminus is sufficient to support the SrtA reaction (Clancy, K. W., et al., Peptide Science 94 (2010) 385-396). The reaction proceeds through a thioester acyl-enzyme intermediate, which is resolved by the attack of an amine nucleophile from the oligoglycine, covalently linking peptidoglycan to a protein substrate and regenerating SrtA. SrtA can be used to covalently conjugate chemically synthetized peptides to recombinantly expressed proteins.

Many gram-positive bacteria use sortase to covalently anchor a variety of surface proteins including virulence factors to their cell wall (peptidoglycan). Sortases are membrane associated enzymes. The wild-type *Staphylococcus aureus* sortase A (SrtA) is a polypeptide of 206 amino acids with an N-terminal membrane-spanning region. In a first step, sortase A recognizes substrate proteins that contain a LPXTG (SEQ ID NO: 01) amino acid sequence motif and cleaves the amide bond between the Thr and Gly by means of an active-site Cys. This peptide cleaving reaction results in a sortase A-substrate thioester intermediate. In a second step the thioester acyl-enzyme intermediate is resolved by nucleophilic attack of an amino group of an oligoglycine containing second substrate polypeptide (corresponding to the pentaglycine unit of peptidoglycan in *S. aureus*) leading to a covalently linked cell wall protein and the regeneration of sortase A. In the absence of oligoglycine nucleophiles, the acyl-enzyme intermediate can be hydrolyzed by a water molecule.

Sortase-mediated ligation/conjugation has begun to be applied for a variety of protein engineering and bioconjugation purposes. This technique enables the introduction of natural and synthetic functionalities into LPXTG-tagged recombinant or chemically synthesized polypeptides. Examples include the covalent attachment of oligoglycine derivatized polymers (e.g. PEG), fluorophores, vitamins (e.g. biotin and folate), lipids, carbohydrates, nucleic acids, synthetic peptides and proteins (e.g. GFP) (see e.g. Tsukiji, S. and Nagamune, T., ChemBioChem 10 (2009) 787-798; Popp, M. W. L. and Ploegh, H. L., Angew. Chem. Int. Ed. Engl. 50 (2011) 5024-5032).

For the enzymatic conjugation a soluble truncated sortase A lacking the membrane-spanning region (SrtA; amino acid residues 60-206 of *Staphylococcus aureus* SrtA) can be used (SEQ ID NO: 05; see also Ton-That, H., et al., Proc. Natl. Acad. Sci. USA 96 (1999) 12424-12429; Ilangovan, H., et al., Proc. Natl. Acad. Sci. USA 98 (2001) 6056-6061).

The sortase A-mediated reaction results in the ligation of species containing a sortase motif (sequence) with those bearing one or more N-terminal glycine residues. The sortase motif can be the amino acid sequence LPXTG, but can also different therefrom (see below). However, a drawback of using such sequences as acyl donors is that the transfer of the LPXT unit to a nucleophilic acyl acceptor liberates a stoichiometric amount of a corresponding fragment containing at least one N-terminal glycine residue. The liberated glycine-containing fragment competes with the intended acyl acceptor for the enzymatic intermediate and works against the progress of the enzymatic ligation reaction. Additionally the hydrolytic cleavage of the enzymatic intermediate as well as the LPXTG containing substrate, although a relatively slow process, compete with the reaction. In the beginning of the use of the sortase-mediated reaction useful levels of ligation could only be obtained using concentrations of at least 5 mM of the acyl donor comprising the sortase-motif.

The general sortase-motif has the amino acid sequence LPXT, wherein X can be any amino acid residue, i.e. a naturally occurring amino acid residue or a non-naturally occurring amino acid residue. In some embodiments, X is selected from the group of amino acid residues comprising or consisting of (in one letter code) D, E, A, N, Q, K, and R. In some embodiments, the sortase-motif is selected from the group comprising or consisting of the amino acid sequences LPXT, LPXA, SPXT, LAXT, LSXT, NPXT, VPXT, IPXT, LGXT, and YPXR. In some embodiments, the sortase motif is selected from the group of amino acid sequences consisting of LPST, LPKT, LPIT, LPDT, SPKT, LAET, LAAT, LAET, LAST, LAET, LPLT, LSRT, LPET, VPDT, IPQT, YPRR, LPMT, LPLT, LAFT, and LPQT. In certain embodiments in which sortase A is used, the sortase-motif comprises the amino acid sequence X1PX2X3, wherein i) X1 is selected from the group consisting of the amino acid residues leucine, isoleucine, valine and methionine, ii) X2 is any amino acid, and iii) X3 is selected from the group consisting of threonine, serine and alanine. In specific embodiments, as noted above X1, is leucine and X3 is threonine. In certain embodiments X2 is selected from the group consisting of aspartate, glutamate, alanine, glutamine, lysine and methionine.

In some embodiments the sortase-motif is selected from the group of amino acid sequences comprising or consisting of LPKTG, LPITG, LPDTA, SPKTG, LAETG, LAATG, LAHTG, LASTG, LAETG, LPLTG, LSRTG, LPETG, VPDTG, IPQTG, YPRRG, LPMTG, LPLTG, LAFTG, and LPQTS. In some embodiments of the invention the sortase is a sortase A (SrtA). SrtA recognizes a sortase-motif with the amino acid sequence LPXTG. Common sortase-motif amino acid sequences are, e.g., LPKTG, LPATG, LPETG and LPNTG. In some embodiments LPETG is used. However, sortase-motifs not in line with this consensus sortase-motif amino acid sequence may also be recognized. For example, in some embodiments the sortase-motif comprises the amino acid residue A rather than the amino acid residue T at position 4, e.g. LPXAG or LPNAG. In some embodiments the sortase-motif comprises the amino acid residue A rather than the amino acid residue G at position 5, e.g. LPXTA or LPNTA. In some embodiments the sortase-motif comprises the amino acid residue G rather than the amino acid residue P at position 2, e.g. LGXTG or LGATG. In some embodiments the sortase-motif comprises the amino acid residue I rather than the amino acid residue L at position 1, e.g., IPXTG or IPNTG or IPETG.

In some embodiments, where the sortase-motif is LPXTG or LPXT, X is selected from the group consisting of D, E, A, N, Q, K, and R. In some embodiments X is selected from the group of amino acid residues consisting of K, E, N, Q, and A in an LPXTG or LPXT motif where the sortase is a sortase A. In one embodiment the sortase-motif is LPET or LPETG or LPETA.

In certain embodiments where sortase A from *Staphylococcus aureus* (Staph. SrtA) is used the sortase-motif has the amino acid sequence LPX1TX2, wherein i) X1 is selected from the group of amino acid residues consisting of D, E, A, N, Q, K, and R, and ii) X2 is selected from the group of amino acid residues consisting of alanine and glycine. In certain embodiments the sortase-motif of Staph. SrtA is LPX1TA. In other embodiments the sortase-motif of Staph. SrtA is LPX1TG. X1 has the meaning as outlined before.

*Streptococcus pyogenes* sortase A (Strep. SrtA) will accept di-alanine based nucleophiles. This sortase will efficiently cleave the sortase-motif amino acid sequence LPXTA between the threonine and the alanine residue and install modified alanine-based nucleophiles. Strep. SrtA will also recognize and cleave LPXTG motifs, albeit with reduced efficiency.

*Staphylococcus aureus* sortase A (Staph. SrtA) will not significantly cleave LPXTA motifs or accept alanine based nucleophiles.

In one embodiment, a polypeptide is contacted with Strep. SrtA and an alanine-containing nucleophile. The polypeptide comprises a sortase-motif amino acid sequence that can be recognized by Strep. SrtA at or near its C-terminus and the nucleophile comprises one or more amino acids capable of serving as nucleophile for a Staph. SrtA-mediated reaction at or near its N-terminus (e.g., (G)n, where n is between 1 and 10, e.g., between 1 and 5). This leads to the formation of an LPXTA sequence at the reactive site, a motif refractory to cleavage by Staph. SrtA. This allows for example Staph. SrtA to act on the N-terminus without affecting the C-terminal modification installed with Strep. SrtA.

Sortase fragments having sortase transamidation activity can be used in the methods as reported herein. Sortase fragments can be identified by producing fragments of sortase, for example, by recombinant techniques or proteolytic digestion of full length sortase, and determining the rate of peptide bond formation, i.e. ligation. The fragment can comprise about 80% of amino acid sequence of full-length sortase, about 70%, about 60%, about 50%, about 40% or about 30% of the amino acid sequence of full-length sortase such as that of *S. aureus* Sortase A (GenBank Accession number AAD48437). In some embodiments the fragment lacks an N-terminal portion of the full-length sortase amino acid sequence that is not essential to the catalytic activity of sortase, for example the fragment lacks the N-terminal portion extending to the end of the membrane anchor sequence. In some embodiments the fragment comprises the C-terminus of a full-length sortase amino acid sequence. In some embodiments, the fragment comprises the catalytic core region of a sortase. In one embodiment the core region is from about position 60 to about position 206 of SrtA, e.g., *S. aureus* SrtA, or about from position 82 to about position 249 of Strep. SrtA.

Sortases from other organisms also can be utilized in the processes as reported herein. Such sortases often are encoded by nucleotide sequences substantially identical or similar to the nucleotide sequences that encode SrtA. A similar or substantially identical nucleotide sequence may include modifications to the native sequence, such as substitutions, deletions, or insertions of one or more nucleotides. Included are nucleotide sequences that are at least 55%, 60%, 65%, 70%, 75%, 80%, or 85% or more identical to a native nucleotide sequence, and often are 90% or 95% or more identical to the native nucleotide sequence (each identity percentage can include a 1%, 2%, 3% or 4% variance). One test for determining whether two nucleic acids are substantially identical is to determine the percentage of identical nucleotide positions shared between two nucleic acids.

SrtA nucleotide sequences may be used as "query sequences" to perform a search against public databases to identify related sequences. Such searches can be performed using the NBLAST and XBLAST programs (version 2.0) of Altschul, et al. (J. Mol. Biol. 215 (1990) 403-410). BLAST nucleotide searches can be performed with the NBLAST program, score=100, word-length=12 to obtain homologous nucleotide sequences. To obtain gapped alignments for comparison purposes, gapped BLAST can be utilized as described in Altschul, et al. (Nuc. Acids Res. 25 (1997) 3389-3402). When utilizing BLAST and Gapped BLAST programs, default parameters of the respective programs (e.g., XBLAST and NBLAST) can be used (see e.g. ncbi.nlm.nih.gov).

A variant amino acid sequence departs from a native amino acid sequence. Amino acid substitutions may be made on the basis of similarity in polarity, charge, solubility, hydrophobicity, hydrophilicity, helix-forming properties and/or amphipathic properties and the resulting variants are screened for enzymatic activity with a suitable assay, such as that reported in European patent application EP14198535. For example, negatively charged amino acids include aspartic acid and glutamic acid; positively charged amino acids include lysine and arginine; and amino acids with uncharged polar or non-polar head groups having similar hydrophilicity values include leucine, isoleucine, valine, glycine, alanine, asparagine, glutamine, serine, threonine, phenylalanine, and tyrosine. In certain embodiments, conservative substitutions may be made, according to the following Table. Amino acids in the same block in the second column and in the same line in the third column may be substituted for one another other in a conservative substitution. Certain conservative substitutions are substituting an amino acid in one row of the third column corresponding to a block in the second column with an amino acid from another row of the third column within the same block in the second column.

| aliphatic amino acid residues | non-polar | G, A, P |
| --- | --- | --- |
| | | I, L, V |
| | polar, non-charged | C, S, T, M |
| | | N, Q |
| | polar, charged | D, E |
| | | K, R |
| aromatic | | H, F, W, Y |

In certain embodiments homologous substitution may occur, which is a substitution or replacement of like amino acids, such as basic for basic, acidic for acidic, polar for polar amino acids, and hydrophobic for hydrophobic, for example. Non-homologous substitutions can be introduced to a native sequence, such as from one class of residue to another (e. g. a non-hydrophobic to a hydrophobic amino acid), or substituting a naturally occurring amino acid with an unnatural amino acids or non-classical amino acid replacements.

In the methods as reported herein the sortase, the sortase-motif comprising polypeptide (i.e. the acyl donor), and the nucleophile (i.e. the acyl acceptor) are incubated together under conditions suitable to effect the formation of a peptide bond between the N-terminal part of the sortase-motif comprising polypeptide and the nucleophile. As used herein, the term "incubating" or grammatical equivalents thereof denotes that the components of the process are brought in close proximity to one another to allow contact between the molecules. Incubating can be done by adding them to one reaction vessel, for example. The components in the system may be mixed in a variety of manners, such as by oscillating a vessel, subjecting a vessel to a vortex generating apparatus, or repeated mixing with a pipette or pipettes, for example. The components may be added in any order to the system.

The sortase reaction may be performed in any convenient vessel (e.g., tubes such as microfuge tubes, flask, dish), microtiter plates (e.g., 96-well or 384-well plates), glass slides, silicon chips, filters, or any solid or semisolid support having surface (optionally coated) having molecules immobilized thereon and optionally oriented in an array (see, e.g., U.S. Pat. No. 6,261,776 and Fodor, Nature 364 (1993) 555-556), and microfluidic devices (see, e.g., U.S. Pat. Nos. 6,440,722; 6,429,025; 6,379,974; and 6,316,781).

The reaction mixture is generally cell free and further does not include bacterial cell wall components or intact bacterial cell walls. In some embodiments, the sortase-motif comprising polypeptide and/or the nucleophile are expressed by one or more recombinant nucleotide sequences in a cell, which nucleotide sequences are integrated into the cell genome or non-integrated (e.g., in a plasmid).

The reaction mixture is maintained at any convenient temperature at which the sortase reaction can be performed. In some embodiments, the sortase reaction is performed at a temperature between and including about 15° C. and about 50° C. In some embodiments, the sortase reaction is performed at a temperature between and including about 23° C. and about 37° C. In certain embodiments, the temperature is room temperature (i.e. about 20° C. to 25° C.). The temperature can be optimized by repetitively performing the same sortase reaction at different temperatures and determining ligation rates.

Any convenient volume and component ratio can be used.

In certain embodiments, a (molar) ratio of 1:1000 or greater of sortase enzyme to sortase-motif comprising polypeptide is utilized, or a (molar) ratio of 1:1000 or greater of sortase enzyme to nucleophile is utilized. In specific embodiments, ratios of sortase enzyme to sortase-motif comprising polypeptide or enzyme to nucleophile is about 1:1, including 1:2 or greater, 1:3 or greater, 1:4 or greater, 1:5 or greater, 1:6 or greater, 1:7 or greater, 1:8 or greater, and 1:9 or greater.

In some embodiments, the sortase-motif comprising polypeptide is present at a concentration ranging from about 10 μM to about 10 mM. In some embodiments, the sortase-motif comprising polypeptide is present at a concentration ranging from about 100 μM to about 1 mM. In some embodiments, the sortase-motif comprising polypeptide is present at a concentration ranging from about 100 μM to about 50 mM. In some embodiments, the sortase-motif comprising polypeptide is present at a concentration ranging from about 200 μM to about 10 mM. In some embodiments, the sortase-motif comprising polypeptide is present at a concentration ranging from about 200 μM to about 800 μM. In some embodiments, the sortase-motif comprising polypeptide is present at a concentration ranging from about 400 μM to about 600 μM.

In certain embodiments the nucleophile is present in excess with respect to the sortase-motif comprising polypeptide. In certain embodiments, the nucleophile is present in 10-fold excess with respect to the sortase-motif polypeptide. In certain embodiments, the nucleophile is present in 25-fold excess with respect to the sortase-motif polypeptide. In certain embodiments, the nucleophile is present in 50-fold excess with respect to the sortase-motif polypeptide. In certain embodiments, the nucleophile is present in 100-fold excess with respect to the sortase-motif polypeptide. In certain embodiments, the nucleophile is present in 250-fold excess with respect to the sortase-motif polypeptide.

In certain embodiments, the nucleophile is present at a concentration ranging from about 1 μM to about 50 mM. In certain embodiments, the nucleophile is present at a concentration ranging from about 15 μM to about 1500 μM. In certain embodiments, the nucleophile is present at a concentration ranging from about 25 μM to about 1000 μM. In certain embodiments, the nucleophile is present at a concentration ranging from about 40 μM to about 250 μM.

In certain embodiments, the sortase is present at a concentration ranging from about 1 μM to about 500 μM. In certain embodiments, the sortase is present at a concentration ranging from about 15 μM to about 150 μM. In certain embodiments, the sortase is present at a concentration ranging from about 25 μM to about 100 μM. In certain embodiments, the sortase is present at a concentration ranging from about 40 μM to about 60 μM.

In certain embodiments, the method is performed in a reaction mixture comprising an aqueous environment. Water with an appropriate buffer and/or salt content often may be utilized. An alcohol or organic solvent may be included in certain embodiments. The amount of an organic solvent often does not appreciably esterify a protein or peptide in the ligation process (e.g., esterified protein or peptide often increase only by 5% or less upon addition of an alcohol or organic solvent). Alcohol and/or organic solvent contents sometimes are 20% or less, 15% or less, 10% or less or 5% or less, and in embodiments where a greater amount of an alcohol or organic solvent is utilized, 30% or less, 40% or less, 50% or less, 60% or less, 70% or less, or 80% or less alcohol or organic solvent is present. In certain embodiments, the reaction mixture includes only an alcohol or an organic solvent, with only limited amounts of water if it is present.

In some embodiments, the reaction mixture comprises a buffer. A person skilled in the art will be familiar with a variety of buffers that could be used in accordance with the methods as reported herein. In some embodiments, the buffer solution comprises calcium ions. In certain embodiments, the buffer solution does not contain substances that precipitate calcium ions. In some embodiments, the buffer solution does not include phosphate ions. In some embodiments, the buffer solution does not contain chelating agents.

In some embodiments, the method is performed at a pH value in the range of from 6 to 8.5. In some embodiments, the method is performed at a pH value in the range of from 6 to 8. In some embodiments, the method is performed at a pH value in the range of from 6 to 7.5. In some embodiments, the method is performed at a pH value in the range of from 6.5 to 8.5. In some embodiments, the method is performed at a pH value in the range of from 7 to 8.5. In some embodiments, the method is performed at a pH value in the range of from 7.5 to 8.5. In some embodiments, the method is performed at a pH value in the range of from 7.0 to 8.5. In some embodiments, the method is performed at a pH value in the range of from 7.3 to 7.8.

One or more components of the reaction mixture or the product may be immobilized to a solid support. The attachment between the reaction mixture component and the solid support may be covalent or non-covalent (see, e.g., U.S. Pat. No. 6,022,688 for non-covalent attachments). The solid support may be one or more surfaces of the system, such as one or more surfaces in each well of a microtiter plate, a surface of a glass slide or silicon wafer, BIAcore chip, a surface of a particle, e.g., a bead (see e.g., Lam, Nature 354 (1991) 82-84) that is optionally linked to another solid support, or a channel in a microfluidic device, for example. Types of solid supports, linker molecules for covalent and non-covalent attachments to solid supports, and methods for immobilizing molecules to solid supports are known (see, e.g., U.S. Pat. Nos. 6,261,776; 5,900,481; 6,133,436; 6,022, 688; WO 2001/18234). Any material may be used, e.g., plastic (e.g., polystyrene), metal, glass, cellulose, gels (e.g., formed at least in part from organic polymers such as PDMS), etc. In some embodiments the solid support is semi-solid and/or gel-like, deformable, flexible, or the like.

Any polypeptide, eventually after introduction of a sortase-motif or an oligoglycine or -alanine, may be used as sortase-motif comprising polypeptide or nucleophile in the methods as reported herein.

Summarizing the above, the first substrate, also denoted as donor, comprises the sortase recognition motif. It is cleaved by the sortase after the threonine residue in the recognition motif. Thereby a C-terminal activated carboxyl group (acyl intermediate) is generated. The second substrate, also denoted as acceptor or nucleophile, provides a free N-terminal amino group. Between the free amino group and the activated carboxyl group a peptide bond is formed in the sortase catalyzed transpeptidation reaction.

Thus, for the enzymatic sortase mediated transpeptidation reaction it is only required that a donor comprising a sortase recognition motif and an acceptor comprising an N-terminal free glycine, alanine, cysteine or an equivalent functional group is incubated with a polypeptide having sortase A catalytic activity. The remainder of the donor as well as of the acceptor does not interfere with the reaction.

Thus, a sortase mediated transpeptidation reaction can be performed with virtually any protein or small molecule independently of each other as donor or acceptor as long as these comprise a pair of sortase recognition sequence and nucleophile.

This is confirmed by the art.

For example, Marraffini et al. (Microbiol. Mol. Biol. Rev. 70 (2006) 192-221) reported that sortase A can be used to incorporate chemicals containing glycine residues with a free amino group to the LPXTG motif of recombinant proteins, i.e. without limitation of the protein. Presented examples are the conjugation of triglycyl-lysine-folate with (GFP or Cre or p27)-LPETG-His6 with high efficiency, the incorporation of the branched peptide AT-P-022 into polypeptides, and the self-cleavage of chimeras of His6-sortase-LPETG-target protein (the fusion cleaves itself once the enzyme has been activated by the addition of calcium and triglycine).

Further, Antos et al. (J. Am. Chem. Soc. 131 (2009) 10800-10801) reported that the transpeptidation reaction catalyzed by sortase A allows site-specific derivatization of proteins with virtually any type of functional material. Target proteins are engineered to contain the recognition site (LPXTG) near their C terminus, thus allowing a transacylation reaction in which the residues C-terminal to threonine are exchanged for a synthetic oligoglycine peptide. It is reported that the terminal G residue of the sortase recognition motif can be replaced by a methyl ester without imparting the reaction. In this document nucleophiles comprising either a fluorescent label or a protein were used for the conjugation to cholera toxin B subunit.

Further, Popp et al. (Proc. Natl. Acad. Sci. USA 108 (2011) 3169-3174) reported the use of Sortase for polypeptide cyclization and PEGylation. The method is general and applicable to a wide variety of proteins. The sortase transpeptidase reaction allows facile site-specific PEGylation of multiple distinct proteins, as exemplified using interferon a2, GCSF, and erythropoietin. In all cases tested, the site-specific C-terminal PEGylation proceeded efficiently.

In EP 2 990 423 a self-cleaving sortase construct is reported. In this construct the sortase recognition sequence LPETG and the catalytic sortase domain have been combined in the same molecule. As protein comprising the sortase recognition sequence any protein, such as e.g. a protein selected from the group comprising polymer proteins, glycoproteins, cytokines, growth factor, blood preparations, vaccines, hormones, enzymes, antibodies and parts or fragments thereof (isolated light or heavy chains).

IV. The Method as Reported Herein

It has been found that sortase A accepts as nucleophile a polypeptide comprising at its N-terminus a cysteine amino acid residue. The resulting enzymatic conjugation product that is released from the enzyme is a thioester. It has further been found that site specific, in situ generated C-terminal thioester between the sortase motif and the Sortase itself can be used for native chemical ligation (NCL).

One aspect as reported herein is a method for the enzymatic production (=formation) of a thioester by forming a thioester bond/a method for the enzymatic formation of a thioester comprising the following step incubating i) a first polypeptide comprising (optionally within the 100 C-terminal amino acid residues) the amino acid sequence LPXTG (SEQ ID NO: 01, wherein X can be any amino acid residue), ii) a second polypeptide that has at its N-terminus a cysteine amino acid residue or is a cysteinyl compound, and iii) a third polypeptide with sortase A activity, and thereby producing a thioester.

In one embodiment the cysteinyl compound is a compound that comprises a cysteine amino acid residue with free alpha amino group (in one embodiment a $NH_2$ or $NH_3^+$), and a carboxy group in position 1, which is part of a peptide bond.

In one embodiment the polypeptide with sortase A activity is derived from *Staphylococcus aureus* sortase A or *Listeria monocytogenes* Sortase A.

In one embodiment the third polypeptide is a sortase A or a sortase A fragment that has sortase A catalytical activity. In one embodiment sortase A catalytical activity is determined using a bond forming assay. In one embodiment the bond forming assay is the assay according to example 4.

In one embodiment the method is for the enzymatic conjugation of two polypeptides.

In one embodiment the second polypeptide has at its N-terminus a cysteine amino acid residue followed by one to three glycine or alanine amino acid residues. In one preferred embodiment the second polypeptide has the amino acid sequence CGG, CGGG (SEQ ID NO: 02), CAA or CAAA (SEQ ID NO: 03) at its N-terminus.

In one embodiment the incubating is further in the presence of a thiol additive. In one embodiment the thiol additive is selected from the group consisting of thiophenol, 4-mercaptophenylacetic acid (MPAA), 2-mercaptoethanesulfonate (MESNA) and combinations thereof. In one preferred embodiment the incubating is in the presence of 2-mercaptoethanesulfonate.

In one embodiment the first polypeptide comprises within the 250 C-terminal amino acid residues the amino acid sequence LPXTG (SEQ ID NO: 01, wherein X can be any amino acid residue). In one embodiment the first polypeptide comprises within the 100 C-terminal amino acid residues the amino acid sequence LPXTG (SEQ ID NO: 01, wherein X can be any amino acid residue). In one embodiment the first polypeptide comprises within the 25 C-terminal amino acid residues the amino acid sequence LPXTG (SEQ ID NO: 01, wherein X can be any amino acid residue). In one embodiment the first polypeptide comprises within the 10 C-terminal amino acid residues the amino acid sequence LPXTG (SEQ ID NO: 01, wherein X can be any amino acid residue).

In one embodiment the first polypeptide comprises at its C-terminus the amino acid sequence LPXTG (SEQ ID NO: 01, wherein X can be any amino acid residue). In one embodiment the first polypeptide comprises at its C-terminus the amino acid sequence LPETG (SEQ ID NO: 04).

In one embodiment the first polypeptide and the second polypeptide are independently of each other selected from an antibody variable domain, an antibody heavy chain Fab-fragment, an antibody Fc-region, a tag, and a peptide comprising the amino acid sequence LPXTG (SEQ ID NO: 01, wherein X can be any amino acid residue), a linker and a non-sortase motif moiety.

In one embodiment the third polypeptide has the amino acid sequence of SEQ ID NO: 05 or SEQ ID NO: 06.

The First or Second Polypeptide

The sortase-motif (amino acid sequence) may be conjugated to or incorporated in, if it is not directly comprised in one of these molecules, a therapeutic agent (drug), a cytotoxic agent (e.g. a toxin such as doxorubicin or pertussis toxin), a fluorophore such as a fluorescent dye like fluorescein or rhodamine, a chelating agent for an imaging or radiotherapeutic metal, a peptidyl or non-peptidyl label, a tag, or a clearance-modifying agent such as various isomers of polyethylene glycol, a peptide that binds to a third component, another carbohydrate or lipophilic agent, or a small molecule, such as e.g. a synthetic small molecule (e.g. acetyl salicylic acid). If the motif is incorporated via conjugation the conjugation can be either directly or via an intervening linker. Furthermore the first and/or second polypeptide can either be recombinantly produced or can be synthetic or semi-synthetic, i.e. recombinantly produced and thereafter chemically modified.

a) Therapeutic Agents

The therapeutic agent can be any compound, moiety or group which has a therapeutic effect, such as e.g. an antibody, a cytotoxic or cytostatic compound. The antibody can be a full length or complete antibody or an antigen-binding fragment thereof.

A number of therapeutic antibodies directed against cell surface molecules and their ligands are known, such as Rituxan/MabThera/Rituximab, 2H7/Ocrelizumab, Zevalin/Ibrizumomab, Arzerra/Ofatumumab (CD20), HLL2/Epratuzumab, Inotuzomab (CD22), Zenapax/Daclizumab, Simulect/Basiliximab (CD25), Herceptin/Trastuzumab, Pertuzumab (Her2/ERBB2), Mylotarg/Gemtuzumab (CD33), Raptiva/Efalizumab (Cd11a), Erbitux/Cetuximab (EGFR, epidermal growth factor receptor), IMC-1121B (VEGF receptor 2), Tysabri/Natalizumab (α4-subunit of α4β1 and α4β7 integrins), ReoPro/Abciximab (gpIIb-gpIIa and αvβ3-integrin), Orthoclone OKT3/Muromonab-CD3 (CD3), Benlysta/Belimumab (BAFF), Tolerx/Oteliximab (CD3), Soliris/Eculizumab (C5 complement protein), Actemra/Tocilizumab (IL-6R), Panorex/Edrecolomab (EpCAM, epithelial cell adhesion molecule), CEA-CAMS/Labetuzumab (CD66/CEA, carcinoembryonic antigen), CT-11 (PD-1, programmed death-1 T-cell inhibitory receptor, CD-d279), H224G11 (c-Met receptor), SAR3419 (CD19), IMC-A12/Cixutumumab (IGF-1R, insulin-like growth factor 1 receptor), MEDI-575 (PDGF-R, platelet-derived growth factor receptor), CP-675, 206/Tremelimumab (cytotoxic T lymphocyte antigen 4), R05323441 (placenta growth factor or PGF), HGS1012/Mapatumumab (TRAIL-R1), SGN-70 (CD70), Vedotin(SGN-35)/Brentuximab (CD30), and ARH460-16-2 (CD44).

The conjugates obtained with the method as reported herein can be used in the preparation of medicaments for the treatment of e.g. an oncologic disease, a cardiovascular disease, an infectious disease, an inflammatory disease, an autoimmune disease, a metabolic (e.g., endocrine) disease, or a neurological (e.g. neurodegenerative) disease. Exemplary non-limiting examples of these diseases are Alzheimer's disease, non-Hodgkin's lymphomas, B-cell acute and chronic lymphoid leukemias, Burkitt lymphoma, Hodgkin's lymphoma, hairy cell leukemia, acute and chronic myeloid leukemias, T-cell lymphomas and leukemias, multiple myeloma, glioma, Waldenstrom's macroglobulinemia, carcinomas (such as carcinomas of the oral cavity, gastrointestinal tract, colon, stomach, pulmonary tract, lung, breast, ovary, prostate, uterus, endometrium, cervix, urinary bladder, pancreas, bone, liver, gall bladder, kidney, skin, and testes), melanomas, sarcomas, gliomas, and skin cancers, acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis, or fibrosing alveolitis.

A number of cell surface markers and their ligands are known. For example cancer cells have been reported to express at least one of the following cell surface markers and or ligands, including but not limited to, carbonic anhydrase IX, alpha fetoprotein, alpha-actinin-4, A3 (antigen specific for A33 antibody), ART-4, B7, Ba-733, BAGE, BrE3-antigen, CA125, CAMEL, CAP-1, CASP-8/m, CCCL19, CCCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD45, CD46, CD54, CD55, CD59, CD64, CD66a-e, CD67, CD70, CD74, CD79a, CD80, CD83, CD95, CD126, CD133, CD138, CD147, CD154, CDC27, CDK-4/m, CDKN2A, CXCR4, CXCR7, CXCL12, HIF-1-alpha, colon-specific antigen-p (CSAp), CEA (CEACAMS), CEACAM6, c-met, DAM, EGFR, EGFRvIII, EGP-1, EGP-2, ELF2-M, Ep-CAM, Flt-1, Flt-3, folate receptor, G250 antigen, GAGE, GROB, HLA-DR, HM1.24, human chorionic gonadotropin (HCG) and its subunits, HER2/neu, HMGB-1, hypoxia inducible factor (HIF-1), HSP70-2M, HST-2 or 1a, IGF-1R, IFN-gamma, IFN-alpha, IFN-beta, IL-2, IL-4R, IL-6R, IL-13R, IL-15R, IL-17R, IL-18R, IL-6, IL-8, IL-12, IL-15, IL-17, IL-18, IL-25, insulin-like growth factor-1 (IGF-1), KC4-antigen, KS-1-antigen, KS1-4, Le-Y, LDR/FUT, macrophage migration inhibitory factor (MIF), MAGE, MAGE-3, MART-1, MART-2, NY-ESO-1, TRAG-3, mCRP, MCP-1, MIP-1A, MIP-1B, MIF, MUC1, MUC2, MUC3, MUC4, MUC5, MUM-1/2, MUM-3, NCA66, NCA95, NCA90, pancreatic cancer mucin, placental growth factor, p53, PLAGL2, prostatic acid phosphatase, PSA, PRAME, PSMA, P1GF, ILGF, ILGF-1R, IL-6, IL-25, RSS, RANTES, T101, SAGE, 5100, survivin, survivin-2B, TAC, TAG-72, tenascin, TRAIL receptors, TNF-alpha, Tn-antigen, Thomson-Friedenreich antigens, tumor necrosis antigens, VEGFR, ED-B fibronectin, WT-1, 17-1A-antigen, complement factors C3, C3a, C3b, C5a, C5, an angiogenesis marker, bcl-2, bcl-6, Kras, cMET, an oncogene marker and an oncogene product (see, e.g., Sensi, et al., Clin. Cancer Res. 12 (2006) 5023-5032; Parmiani, et al, J. Immunol. 178 (2007) 1975-1979; Novellino, et al., Cancer Immunol. Immunother. 54 (2005) 187-207).

Thus, antibodies recognizing specific cell surface receptors including their ligands can be used for specific and selective targeting and binding to a number/multitude of cell surface markers that are associated with a disease. A cell surface marker is a polypeptide located on the surface of a cell (e.g. a disease-related cell) that is e.g. associated with signaling event or ligand binding.

In one embodiment, for the treatment of cancer/tumors multispecific binding molecules/bispecific antibodies are produced that target tumor-associated antigens, such as those reported in Herberman, "Immunodiagnosis of Cancer", in Fleisher (ed.), "The Clinical Biochemistry of Cancer", page 347 (American Association of Clinical Chemists (1979)) and in U.S. Pat. Nos. 4,150,149; 4,361,544; and 4,444,744.

Reports on tumor associated antigens (TAAs) include Mizukami, et al., (Nature Med. 11 (2005) 992-997); Hatfield, et al., (Curr. Cancer Drug Targets 5 (2005) 229-248); Vallbohmer, et al., (J Clin. Oncol. 23 (2005) 3536-3544); and Ren, et al., (Ann. Surg. 242 (2005) 55-63), each incorporated herein by reference with respect to the TAAs identified.

Where the disease involves a lymphoma, leukemia or autoimmune disorder, targeted antigens may be selected from the group consisting of CD4, CD5, CD8, CD14, CD15, CD19, CD20, CD21, CD22, CD23, CD25, CD33, CD37, CD38, CD40, CD40L, CD46, CD54, CD67, CD74, CD79a, CD80, CD126, CD138, CD154, CXCR4, B7, MUC1 or 1a, HM1.24, HLA-DR, tenascin, VEGF, P1GF, ED-B fibronectin, an oncogene, an oncogene product (e.g., c-met or PLAGL2), CD66a-d, necrosis antigens, IL-2, T101, TAG, IL-6, MIF, TRAIL-R1 (DR4) and TRAIL-R2 (DR5).

A number of bispecific antibodies are known directed against two different targets, such as BCMA/CD3, different antigens of the HER family in combination (EGFR, HER2, HER3), CD19/CD3, IL17RA/IL7R, IL-6/IL-23, IL-1-beta/IL-8, IL-6 or IL 6R/IL-21 or IL-21R, first specificity directed to a glycoepitope of an antigen selected from the group consisting of Lewis x-, Lewis b- and Lewis y-structures, Globo H-structures, KH1, Tn-antigen, TF-antigen and carbohydrate structures of Mucins, CD44, glycolipids and glycosphingolipids, such as Gg3, Gb3, GD3, GD2, Gb5, Gm1, Gm2, sialyltetraosylceramide and a second specificity directed to an ErbB receptor tyrosine kinase selected from the group consisting of EGFR, HER2, HER3 and HER4, GD2 in combination with a second antigen binding site is associated with an immunological cell chosen from the group consisting of T lymphocytes NK cell, B-lymphocytes, dendritic cells, monocytes, macrophages, neutrophils, mesenchymal stem cells, neural stem cells, ANG2/VEGF, VEGF/PDGFR-beta, Vascular Endothelial Growth Factor (VEGF) acceptor 2/CD3, PSMA/CD3, EPCAM/CD3, combinations of an antigen is selected from a group consisting of VEGFR-1, VEGFR-2, VEGFR-3, FLT3, c FMS/CSF1R, RET, c-Met, EGFR, Her2/neu, HER3, HER4, IGFR, PDGFR, c-KIT, BCR, integrin and MMPs with a water-soluble ligand is selected from the group consisting of VEGF, EGF, PIGF, PDGF, HGF, and angiopoietin, ERBB-3/C-MET, ERBB-2/C-MET, EGF receptor 1/CD3, EGFR/HER3, PSCA/CD3, C-MET/CD3, ENDOSIALIN/CD3, EPCAM/CD3, IGF-1R/CD3, FAPALPHA/CD3, EGFR/IGF-1R, IL 17A/F, EGF receptor 1/CD3, and CD19/CD16.

Toxic drug moieties include: (i) chemotherapeutic agents, which may function as microtubule inhibitors, mitosis inhibitors, topoisomerase inhibitors, or DNA intercalators; (ii) protein toxins, which may function enzymatically; and (iii) radioisotopes.

Exemplary toxic drug moieties include, but are not limited to, a maytansinoid, an auristatin, a dolastatin, a trichothecene, CC1065, a calicheamicin and other enediyne antibiotics, a taxane, an anthracycline, and stereoisomers, isosters, analogs or derivatives thereof.

Protein toxins include diphtheria-A chain, non-binding active fragments of diphtheria toxin, exotoxin A chain (from *Pseudomonas aeruginosa*), ricin A chain (Vitetta et al (1987) Science, 238:1098), abrin A chain, modeccin A chain, alpha-sarcin, *Aleurites fordii* proteins, dianthin proteins, *Phytolaca americana* proteins (PAPI, PAPII, and PAP-5), *Momordica*

*charantia* inhibitor, curcin, crotin, *Sapaonaria officinalis* inhibitor, gelonin, mitogellin, restrictocin, phenomycin, enomycin, and the tricothecenes (WO 93/21232).

Therapeutic radioisotopes include 32P, 33P, 90Y, 125I, 131I, 131In, 153Sm, 186Re, 188Re, 211At, 212B, 212Pb, and radioactive isotopes of Lu.

The radioisotope or other labels may be incorporated in known ways (Fraker et al (1978) Biochem. Biophys. Res. Commun. 80: 49-57; "Monoclonal Antibodies in Immunoscintigraphy" Chatal, CRC Press 1989). Carbon-14-labeled 1-isothiocyanatobenzyl-3-methyldiethylene triamine pentaacetic acid (MX-DTPA) is an exemplary chelating agent for conjugation of a radionuclide to the complex (WO 94/11026).

b) Labels

The non-sortase motif moiety can be a label. Any label moiety which can be covalently attached to the sortase amino acid sequence can be used (see e.g. Singh et al (2002) Anal. Biochem. 304:147-15; Harlow E. and Lane, D. (1999) Using Antibodies: A Laboratory Manual, Cold Springs Harbor Laboratory Press, Cold Spring Harbor, N.Y.; Lundblad R. L. (1991) Chemical Reagents for Protein Modification, 2nd ed. CRC Press, Boca Raton, Fla.). The label may function to: (i) provide a detectable signal; (ii) interact with a second label to modify the detectable signal provided by the first or second label, e.g. to give FRET (fluorescence resonance energy transfer); (iii) affect mobility, e.g. electrophoretic mobility or cell-permeability, by charge, hydrophobicity, shape, or other physical parameters, or (iv) provide a capture moiety, e.g. to modulate ionic complexation.

Conjugates comprising a haptenylated label as reported herein may be useful in diagnostic assays, e.g., for detecting expression of an antigen of interest in specific cells, tissues, or serum. For diagnostic applications, a bispecific antibody will be used wherein the first binding specificity binds to a target and the second binding specificity binds to a haptenylated label. The hapten will typically be labeled with a detectable moiety. Numerous labels are available which can be generally grouped into the following categories:

(a) Radioisotopes (radionuclides), such as 3H, 11C, 14C, 18F, 32P, 35S, 64Cu, 68Gn, 86Y, 89Zr, 99TC, 111In, 123I, 124I, 125I, 131I, 133Xe, 177Lu, 211At, or 131Bi. Radioisotope labeled conjugates are useful in receptor targeted imaging experiments. The antigen (hapten) can be labeled with ligand reagents that bind, chelate or otherwise complex a radioisotope metal using the techniques described in Current Protocols in Immunology, (1991) Volumes 1 and 2, Coligen et al, Ed. Wiley-Interscience, New York, N.Y., Pubs. Chelating ligands which may complex a metal ion include DOTA, DOTP, DOTMA, DTPA and TETA (Macrocyclics, Dallas, Tex.). Radionuclides can be targeted via complexation with the complex as reported herein (Wu et al, Nature Biotechnology 23(9) (2005) 1137-1146). Receptor target imaging with radionuclide labeled complexes can provide a marker of pathway activation by detection and quantification of progressive accumulation of complexes or corresponding therapeutic antibodies in tumor tissue (Albert et al (1998) Bioorg. Med. Chem. Lett. 8:1207-1210).

Metal-chelate complexes suitable as labels for imaging experiments (US 2010/0111856; U.S. Pat. Nos. 5,342,606; 5,428,155; 5,316,757; 5,480,990; 5,462,725; 5,428,139; 5,385,893; 5,739,294; 5,750,660; 5,834,456; Hnatowich et al, J. Immunol. Methods 65 (1983) 147-157; Meares et al, Anal. Biochem. 142 (1984) 68-78; Mirzadeh et al, Bioconjugate Chem. 1 (1990) 59-65; Meares et al, J. Cancer (1990), Suppl. 10:21-26; Izard et al, Bioconjugate Chem. 3 (1992) 346-350; Nikula et al., Nucl. Med. Biol. 22 (1995) 387-90; Camera et al., Nucl. Med. Biol. 20 (1993) 955-62; Kukis et al., J. Nucl. Med. 39 (1998) 2105-2110; Verel et al., J. Nucl. Med. 44 (2003) 1663-1670; Camera et al., J. Nucl. Med. 21 (1994) 640-646; Ruegg et al, Cancer Res. 50 (1990) 4221-4226; Verel et al., J. Nucl. Med. 44 (2003) 1663-1670; Lee et al, Cancer Res. 61 (2001) 4474-4482; Mitchell, et al., J. Nucl. Med. 44 (2003) 1105-1112; Kobayashi et al Bioconjugate Chem. 10 (1999) 103-111; Miederer et al., J. Nucl. Med. 45 (2004) 129-137; DeNardo et al, Clinical Cancer Research 4 (1998) 2483-90; Blend et al, Cancer Biotherapy & Radiopharmaceuticals 18 (2003) 355-363; Nikula et al J. Nucl. Med. 40 (1999) 166-76; Kobayashi et al., J. Nucl. Med. 39 (1998) 829-36; Mardirossian et al., Nucl. Med. Biol. 20 (1993) 65-74; Roselli et al., Cancer Biotherapy & Radiopharmaceuticals, 14 (1999) 209-20).

(b) Fluorescent labels such as rare earth chelates (europium chelates), fluorescein types including FITC, 5-carboxyfluorescein, 6-carboxy fluorescein; rhodamine types including TAMRA; dansyl; Lissamine; cyanines; phycoerythrins; Texas Red; and analogs thereof. The fluorescent labels can be conjugated to the antigen (hapten) using the techniques disclosed in Current Protocols in Immunology, supra, for example. Fluorescent dyes and fluorescent label reagents include those which are commercially available from Invitrogen/Molecular Probes (Eugene, Oreg., USA) and Pierce Biotechnology, Inc. (Rockford, Ill.).

Detection labels such as fluorescent dyes and chemiluminescent dyes (Briggs et al "Synthesis of Functionalised Fluorescent Dyes and Their Coupling to Amines and Amino Acids," J. Chem. Soc., Perkin-Trans. 1 (1997) 1051-1058) provide a detectable signal and are generally applicable for labeling, especially with the following properties: (i) the labeled conjugate should produce a very high signal with low background so that small quantities of conjugate can be sensitively detected in both cell-free and cell-based assays; and (ii) the labeled conjugate should be photostable so that the fluorescent signal may be observed, monitored and recorded without significant photo bleaching. For applications involving cell surface binding of labeled conjugates to membranes or cell surfaces, especially live cells, the labels should (iii) have good water-solubility to achieve effective conjugate concentration and detection sensitivity and (iv) are non-toxic to living cells so as not to disrupt the normal metabolic processes of the cells or cause premature cell death.

(c) Various enzyme-substrate labels are available or disclosed (see e.g. U.S. Pat. No. 4,275,149). The enzyme generally catalyzes a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase (AP), (3-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to polypeptides are described in O'Sullivan et al "Methods for the Preparation of Enzyme-Antibody Conjugates for use in Enzyme Immunoassay", in Methods in Enzym. (ed. by J. Langone & IT Van Vunakis), Academic Press, New York, 73 (1981) 147-166.

Examples of enzyme-substrate combinations (U.S. Pat. Nos. 4,275,149; 4,318,980) include, for example:

(i) Horseradish peroxidase (HRP) with hydrogen peroxidase as a substrate, wherein the hydrogen peroxidase oxidizes a dye precursor (e.g., orthophenylene diamine (OPD) or 3,3',5,5'-tetramethylbenzidine hydrochloride (TMB));

(ii) alkaline phosphatase (AP) with para-nitrophenyl phosphate as chromogenic substrate; and (iii) (3-D-galactosidase ((3-D-Gal) with a chromogenic substrate (e.g., p-nitro phenyl-(3-D-galactosidase) or fluorogenic substrate 4-methylumbelliferyl-(3-D-galactosidase.

The labeled conjugate as reported herein may be employed in any known assay method, such as ELISA, competitive binding assays, direct and indirect sandwich assays, and immunoprecipitation assays (Zola, Monoclonal Antibodies: A Manual of Techniques (1987) pp. 147-158, CRC Press, Inc.).

Labeled conjugates as reported herein are useful as imaging biomarkers and probes by the various methods and techniques of biomedical and molecular imaging such as: (i) MRI (magnetic resonance imaging); (ii) MicroCT (computerized tomography); (iii) SPECT (single photon emission computed tomography); (iv) PET (positron emission tomography) Tinianow, J. et al, Nuclear Medicine and Biology, 37(3) (2010) 289-297; Chen et al, Bioconjugate Chem. 15 (2004) 41-49; US 2010/0111856 (v) bioluminescence; (vi) fluorescence; and (vii) ultrasound. Immunoscintigraphy is an imaging procedure in which conjugates labeled with radioactive substances are administered to an animal or human patient and a picture is taken of sites in the body where the conjugate localizes (U.S. Pat. No. 6,528,624). Imaging biomarkers may be objectively measured and evaluated as an indicator of normal biological processes, pathogenic processes, or pharmacological responses to a therapeutic intervention. Biomarkers may be of several types: Type 0 markers are natural history markers of a disease and correlate longitudinally with known clinical indices, e.g. MRI assessment of synovial inflammation in rheumatoid arthritis; Type I markers capture the effect of an intervention in accordance with a mechanism-of-action, even though the mechanism may not be associated with clinical outcome; Type II markers function as surrogate endpoints where the change in, or signal from, the biomarker predicts a clinical benefit to "validate" the targeted response, such as measured bone erosion in rheumatoid arthritis by CT. Imaging biomarkers thus can provide pharmacodynamic (PD) therapeutic information about: (i) expression of a target protein, (ii) binding of a therapeutic to the target protein, i.e. selectivity, and (iii) clearance and half-life pharmacokinetic data. Advantages of in vivo imaging biomarkers relative to lab-based biomarkers include: non-invasive treatment, quantifiable, whole body assessment, repetitive dosing and assessment, i.e. multiple time points, and potentially transferable effects from preclinical (small animal) to clinical (human) results. For some applications, bioimaging supplants or minimizes the number of animal experiments in preclinical studies.

Peptide labeling methods are well known. See Haugland (2003) Molecular Probes Handbook of Fluorescent Probes and Research Chemicals, Molecular Probes, Inc.; Brinkley (1992) Bioconjugate Chem. 3:2; Garman, (1997) Non-Radioactive Labeling: A Practical Approach, Academic Press, London; Means (1990) Bioconjugate Chem. 1:2; Glazer et al Chemical Modification of Proteins. Laboratory Techniques in Biochemistry and Molecular Biology (T. S. Work and E. Work, Eds.) American Elsevier Publishing Co., New York; Lundblad, R. L. and Noyes, C. M. (1984) Chemical Reagents for Protein Modification, Vols. I and II, CRC Press, New York; Pfleiderer, G. (1985) "Chemical Modification of Proteins", Modem Methods in Protein Chemistry, H. Tschesche, Ed., Walter DeGruyter, Berlin and New York; and Wong (1991) Chemistry of Protein Conjugation and Cross-linking, CRC Press, Boca Raton, Fla.); DeLeon-Rodriguez et al, Chem. Eur. J. 10 (2004) 1149-1155; Lewis et al, Bioconjugate Chem. 12 (2001) 320-324; Li et al, Bioconjugate Chem. 13 (2002) 110-115; Mier et al Bioconjugate Chem. 16 (2005) 240-237.

c) Linker

The term "linker" denotes a bifunctional or multifunctional moiety which can be used to conjugate (link) a first moiety with a second moiety. Linked conjugates can be conveniently prepared using a linker having two reactive functionalities.

In one embodiment, a linker has a reactive site which has an electrophilic group that is reactive to a nucleophilic group present in the sortase amino acid sequence. Useful electrophilic groups include, but are not limited to, another thiol, maleimide and haloacetamide groups (see e.g. conjugation method at page 766 of Klussman et al, Bioconjugate Chemistry 15(4) (2004) 765-773).

Examples of thiol-reaction functional groups include, but are not limited to, thiol, maleimide, and alpha-haloacetyl.

The linker may comprise amino acid residues which link the sortase amino acid sequence to the non-sortase motif moiety. The amino acid residues may form a dipeptide, tripeptide, tetrapeptide, pentapeptide, hexapeptide, heptapeptide, octapeptide, nonapeptide, decapeptide, undecapeptide or dodecapeptide unit. Amino acid residues include those occurring naturally, as well as non-naturally occurring amino acid analogs, such as e.g. citrulline or β-amino acids, such as e.g. β-alanine, or w-amino acids such as 4-aminobutyric acid.

In another embodiment, the linker has a reactive functional group which has a nucleophilic group that is reactive to an electrophilic group present in the sortase amino acid sequence. Useful electrophilic groups include, but are not limited to, aldehyde and ketone carbonyl groups. The heteroatom of a nucleophilic group of a linker can react with an electrophilic group in the sortase amino acid sequence and form a covalent bond to the sortase amino acid sequence. Useful nucleophilic groups on a linker include, but are not limited to, hydrazide, oxime, amino, hydrazine, hydrazine carboxylate, and arylhydrazide. The electrophilic group on an antigen (hapten) provides a convenient site for attachment to a linker.

Typically, peptide-type linkers can be prepared by forming a peptide bond between two or more amino acids and/or peptide fragments. Such peptide bonds can be prepared, for example, according to the liquid phase synthesis method (E. Schroder and K. Lubke "The Peptides", volume 1 (1965) 76-136, Academic Press) which is well known in the field of peptide chemistry.

In another embodiment, the linker may be substituted with groups which modulated solubility or reactivity. For example, a charged substituent such as sulfonate (SO3-) or ammonium or a polymer such as PEG, may increase water solubility of the reagent and facilitate the coupling reaction of the linker reagent with the antigen (hapten) or the drug moiety, or facilitate the coupling reaction depending on the synthetic route employed.

The conjugates comprising a non-sortase motif moiety as reported herein expressly contemplate, but are not limited to, complexes prepared with linker reagents: BMPEO, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone) benzoate), and including bis-maleimide reagents: DTME, BMB, BMDB, BMH, BMOE, BM(PEO)3, and BM(PEO)4, which are commercially available from Pierce Biotechnology, Inc. Bis-maleimide reagents allow the attachment of e.g. a thiol group to a thiol-containing drug moiety, label, or linker intermediate, in a sequential or concurrent fashion. Other functional groups besides maleimide, which are reactive with e.g. a thiol group, include iodoacetamide, bromoacetamide, vinyl pyridine, disulfide, pyridyl disulfide, isocyanate, and isothiocyanate.

Exemplary linker include a valine-citrulline (val-cit or vc) dipeptide linker reagent having a maleimide stretcher and a para-aminobenzylcarbamoyl (PAB) self-immolative spacer, and a phe-lys(Mtr) dipeptide linker reagent having a maleimide Stretcher unit and a p-amino benzyl self-immolative spacer.

Cysteine thiol groups are nucleophilic and capable of reacting to form covalent bonds with electrophilic groups on linker reagents and the non-sortase motif moiety or the sortase amino acid sequence including: (i) active esters such as NHS esters, HOBt esters, haloformates, and acid halides; (ii) alkyl and benzyl halides, such as haloacetamides; (iii) aldehydes, ketones, carboxyl, and maleimide groups; and (iv) disulfides, including pyridyl disulfides, via sulfide exchange. Nucleophilic groups on a haptenylated compound include, but are not limited to: amine, thiol, hydroxyl, hydrazide, oxime, hydrazine, hydrazine carboxylate, and arylhydrazide groups capable of reacting to form covalent bonds with electrophilic groups on linker moieties and linker reagents.

V. Recombinant Methods

Any polypeptide domain (e.g. a single chain antigen binding polypeptide such as a scFv, a scFab, or a darpin, or a multi chain antigen binding polypeptide such as a dsFv or a Fab) comprising an nucleophilic amino acid sequence at its N-terminus, such as e.g. an oligoglycine motif (GG (SEQ ID NO: 28), GGG (SEQ ID NO: 29), GGGG (SEQ ID NO: 30), GGGGG (SEQ ID NO: 31)), can be expressed and purified from the supernatant of eukaryotic cells (e.g. HEK293 cells, CHO cells). It does not matter if the polypeptide is an isolated polypeptide or comprised in a multimeric or heteromeric entity.

Suitable host cells for cloning or expression/secretion of polypeptide-encoding vectors include prokaryotic or eukaryotic cells described herein. For example, polypeptides may be produced in bacteria, in particular when glycosylation is not needed (see, e.g., U.S. Pat. Nos. 5,648,237, 5,789,199 and 5,840,523, Charlton, Methods in Molecular Biology 248 (2003) 245-254 (B. K. C. Lo, (ed.), Humana Press, Totowa, N.J.), describing expression of antibody fragments in E. coli.). After expression, the polypeptide may be isolated from the bacterial cell paste in a soluble fraction or may be isolated from the insoluble fraction so called inclusion bodies which can be solubilized and refolded to bioactive forms. Thereafter the polypeptide can be further purified.

In addition to prokaryotes, eukaryotic microbes such as filamentous fungi or yeasts are suitable cloning or expression hosts for polypeptide-encoding vectors, including fungi and yeast strains whose glycosylation pathways have been "humanized", resulting in the production of a polypeptide with a partially or fully human glycosylation pattern (see e.g. Gemgross, Nat. Biotech. 22 (2004) 1409-1414, and Li, et al., Nat. Biotech. 24 (2006) 210-215).

Suitable host cells for the expression of glycosylated polypeptides are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells.

Plant cell cultures can also be utilized as hosts (see, e.g., U.S. Pat. Nos. 5,959,177, 6,040,498, 6,420,548, 7,125,978 and 6,417,429 (describing PLANTIBODIES™ technology for producing antibodies in transgenic plants)).

Vertebrate cells may also be used as hosts. For example, mammalian cell lines that are adapted to grow in suspension may be useful. Other examples of useful mammalian host cell lines are the COS-7 cell line (monkey kidney CV1 cell transformed by SV40); the HEK293 cell line (human embryonic kidney); the BHK cell line (baby hamster kidney); the TM4 mouse sertoli cell line (TM4 cells as described, e.g., in Mather, Biol. Reprod. 23 (1980) 243-251); the CV1 cell line (monkey kidney cell); the VERO-76 cell line (African green monkey kidney cell); the HELA cell line (human cervical carcinoma cell); the MDCK cell line (canine kidney cell); the BRL-3A cell line (buffalo rat liver cell); the W138 cell line (human lung cell); the HepG2 cell line (human liver cell); the MMT 060562 cell line (mouse mammary tumor cell); the TRI cell line (e.g. described in Mather, et al., Anal. N.Y. Acad. Sci. 383 (1982) 44-68); the MRCS cell line; and the FS4 cells-line. Other useful mammalian host cell lines include the CHO cell line (Chinese hamster ovary cell), including DHFR negative CHO cell lines (see e.g. Urlaub, et al., Proc. Natl. Acad. Sci. USA 77 (1980) 4216), and myeloma cell lines such as Y0, NS0 and Sp2/0 cell line. For a review of certain mammalian host cell lines suitable for polypeptide production, see, e.g., Yazaki, and Wu, Methods in Molecular Biology, Antibody Engineering 248 (2004) 255-268 (B. K. C. Lo, (ed.), Humana Press, Totowa, N.J.).

Figure 1:
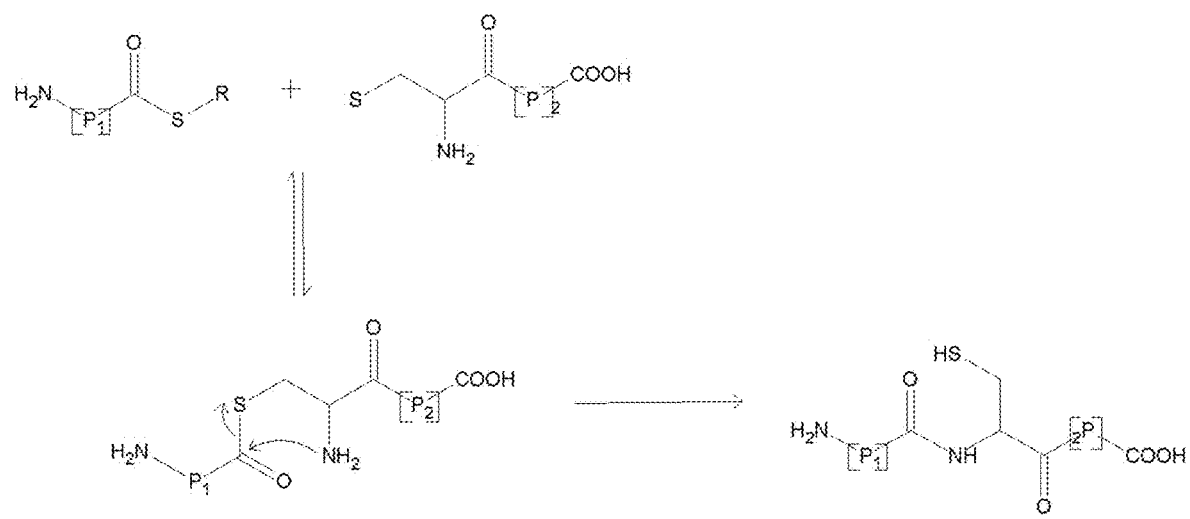
FIG. 1 Scheme showing the native chemical ligation reaction.
Figure 2:
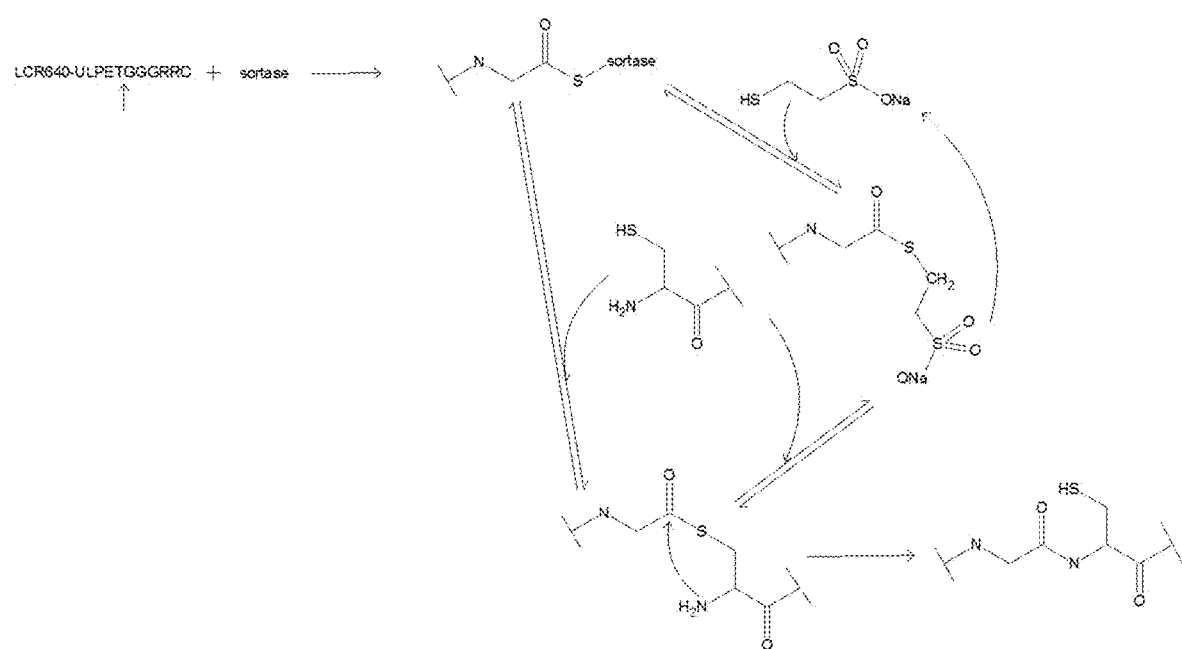
FIG. 2 Scheme showing the use of Sortase in NCL.

The following examples, figures and sequences are provided to aid the understanding of the present invention, the true scope of which is set forth in the appended claims. It is understood that modifications can be made in the procedures set forth without departing from the spirit of the invention.

EXAMPLES

Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

Gene and Oligonucleotide Synthesis

Desired gene segments were prepared by chemical synthesis at Geneart GmbH (Regensburg, Germany). The synthesized gene fragments were cloned into an *E. coli* plasmid for propagation/amplification. The DNA sequences of subcloned gene fragments were verified by DNA sequencing. Alternatively, short synthetic DNA fragments were assembled by annealing chemically synthesized oligonucleotides or via PCR. The respective oligonucleotides were prepared by metabion GmbH (Planegg-Martinsried, Germany).

Description of the Basic/Standard Mammalian Expression Plasmid

For the expression of a desired gene/protein (e.g. full length antibody heavy chain, full length antibody light chain, or an Fc-chain containing an oligoglycine at its N-terminus) a transcription unit comprising the following functional elements is used:
- the immediate early enhancer and promoter from the human cytomegalovirus (P-CMV) including intron A,
- a human heavy chain immunoglobulin 5'-untranslated region (5'UTR),
- a murine immunoglobulin heavy chain signal sequence,
- a gene/protein to be expressed (e.g. full length antibody heavy chain), and
- the bovine growth hormone polyadenylation sequence (BGH pA).

Beside the expression unit/cassette including the desired gene to be expressed the basic/standard mammalian expression plasmid contains
- an origin of replication from the vector pUC18 which allows replication of this plasmid in *E. coli*, and
- a beta-lactamase gene which confers ampicillin resistance in *E. coli*.

Protein Determination

The protein concentration of purified polypeptides was determined by determining the optical density (OD) at 280 nm, using the molar extinction coefficient calculated on the basis of the amino acid sequence of the polypeptide.

Example 1

Generation of an Expression Plasmid for Soluble *S. aureus* Sortase A

The sortase gene encodes an N-terminally truncated *Staphylococcus aureus* sortase A (60-206) molecule (amino acid sequence of SEQ ID NO: 05).

The expression plasmid for the expression of soluble sortase in *E. coli* cells comprised besides the soluble sortase expression cassette an origin of replication from the vector pUC18, which allows replication of this plasmid in *E. coli*, and the URA3 gene as selectable marker, and the Lad gene to allow induction of transcription using IPTG.

The transcription unit of the soluble sortase comprised the following functional elements:
- a T5 promoter,
- a purification tag,
- an N-terminally truncated *S. aureus* sortase A encoding nucleic acid, and
- the To and fd termination sequences.

The expression plasmid for the transient expression of soluble sortase in HEK293 cells comprised besides the soluble sortase expression cassette an origin of replication from the vector pUC18, which allows replication of this plasmid in *E. coli*, and a beta-lactamase gene which confers ampicillin resistance in *E. coli*.

The transcription unit of the soluble sortase comprised the following functional elements:
- the immediate early enhancer and promoter from the human cytomegalovirus (P-CMV) including intron A,
- a human heavy chain immunoglobulin 5'-untranslated region (5'UTR),
- a murine immunoglobulin heavy chain signal sequence,
- a purification tag encoding nucleic acid,
- an N-terminally truncated *S. aureus* sortase A encoding nucleic acid, and
- the bovine growth hormone polyadenylation sequence (BGH pA).

The amino acid sequence of the mature soluble sortase is

```
                                          (SEQ ID NO: 05)
QAKPQIPKDKSKVAGYIEIPDADIKEPVYPGPATPEQLNRGVSFAEENES

LDDQNISIAGHTFIDRPNYQFTNLKAAKKGSMVYFKVGNETRKYKMTSIR

DVKPTDVGVLDEQKGKDKQLTLITCDDYNEKTGVWEKRKIFVATEVK.
```

The purification tag has the amino acid sequence MRGSHHHHHHGS (SEQ ID NO: 32).

Example 2

Transient Expression and Analytical Characterization

Figure 3:
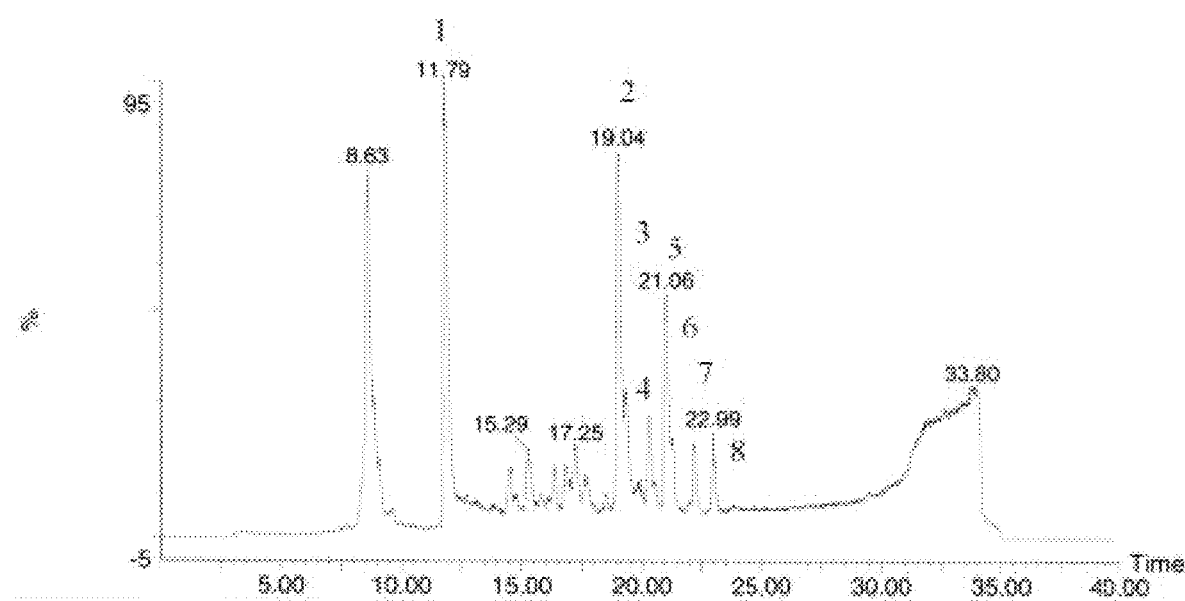
FIG. 3 Chromatogram of the reaction product of Example 3.
Figure 4A:
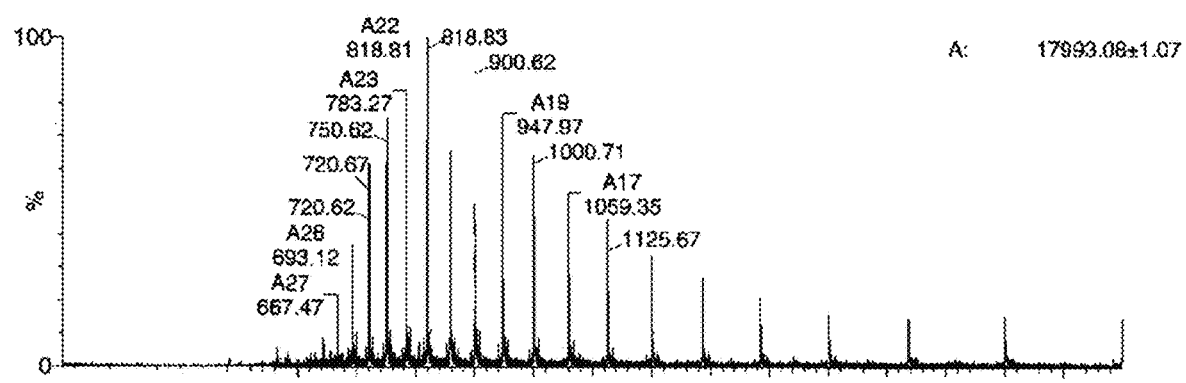
FIG. 4A Mass-spectrum of peak 1 of the chromatogram of FIG. 3.
Figure 4B:
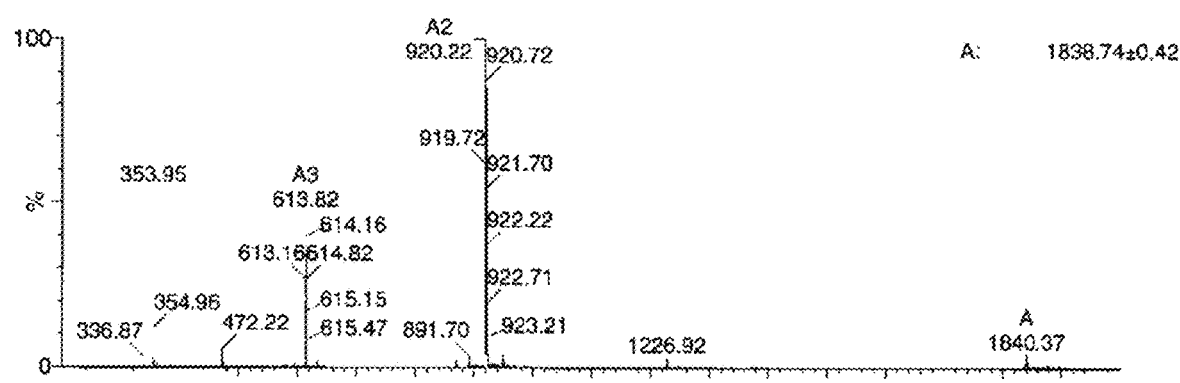
FIG. 4B Mass-spectrum of peak 2 of the chromatogram of FIG. 3.
Figure 4C:
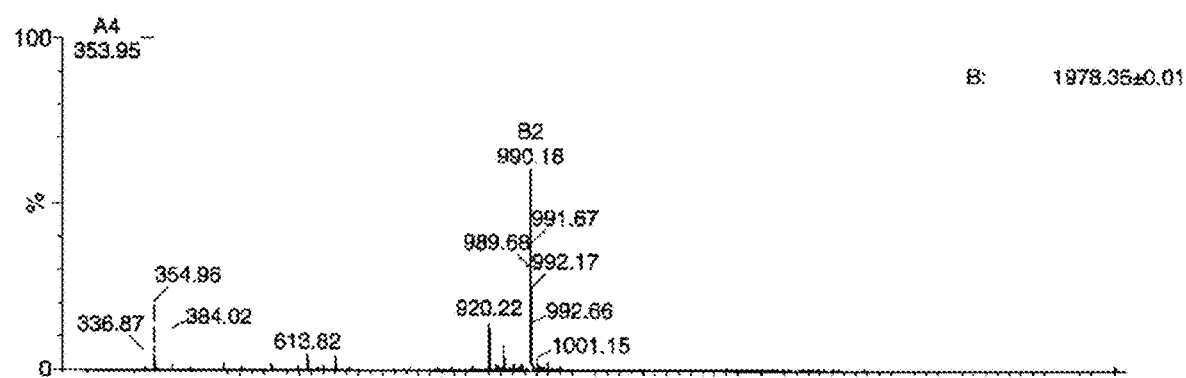
FIG. 4C Mass-spectrum of peak 3 of the chromatogram of FIG. 3.
Figure 4D:
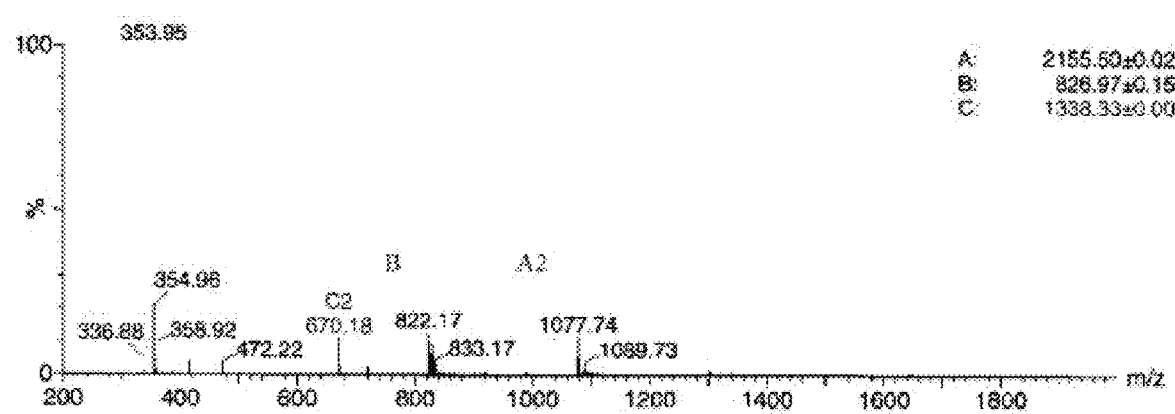
FIG. 4D Mass-spectrum of peak 4 of the chromatogram of FIG. 3.
Figure 4E:
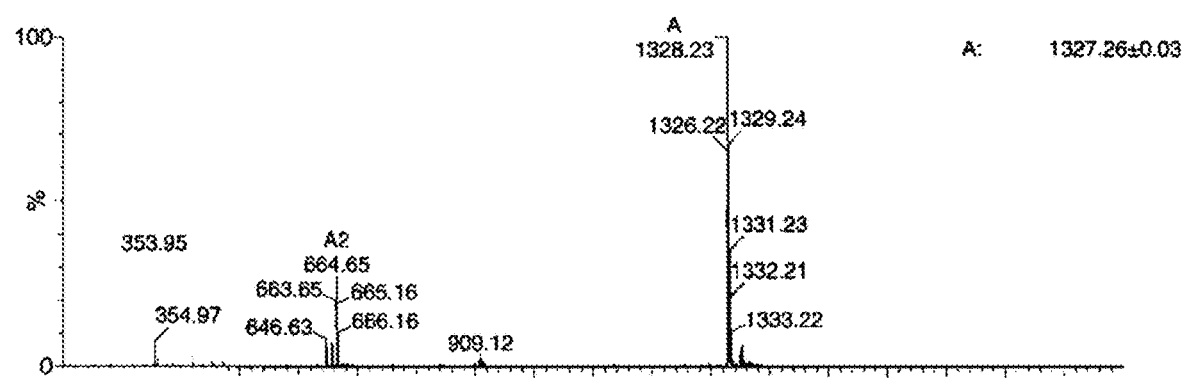
FIG. 4E Mass-spectrum of peak 5 of the chromatogram of FIG. 3.
Figure 4F:
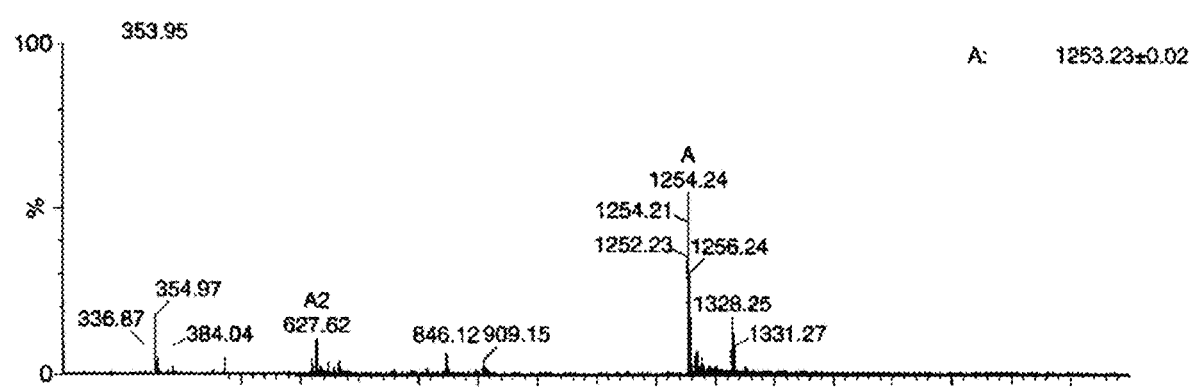
FIG. 4F Mass-spectrum of peak 6 of the chromatogram of FIG. 3.
Figure 4G:
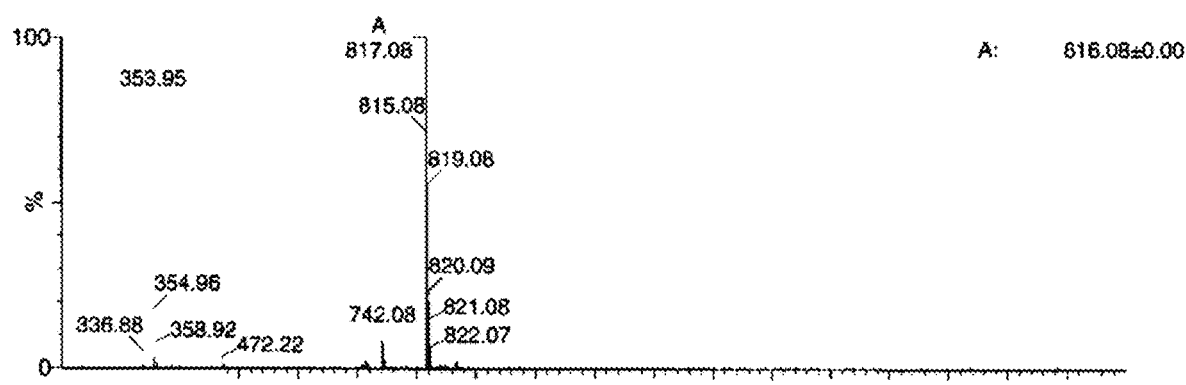
FIG. 4G Mass-spectrum of peak 7 of the chromatogram of FIG. 3.
Figure 4H:
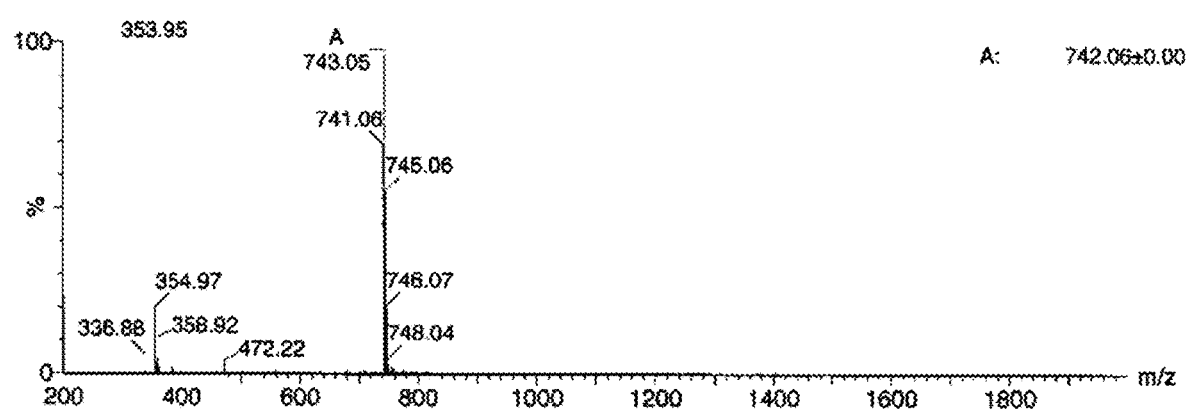
FIG. 4H Mass-spectrum of peak 8 of the chromatogram of FIG. 3.

*E. coli*:

The recombinant production of Sortase was performed by growing *E. coli* cells transformed with the respective Sortase expression plasmids to an OD578 of approx. 0.9 at 37° C. (pre-culture). At this OD578 of approx. 0.9 protein expression was induced by adding 2 mM IPTG and growing the cells for an additional 24 hours at 28° C. Thereafter, cells were harvested by centrifugation and lysed via high pressure using a homogenizer. Cell lysates were centrifuged to remove cell debris and subsequently the cell lysates were stored at reduced temperature (e.g. −80° C.) until purification. Soluble Sortase was purified using Ni-NTA chromatography followed by size exclusion chromatography. For depletion of endotoxins an anion exchange chromatography was performed in flow through mode. The protein concentration of sortase preparations was determined by measuring the optical density (OD) at 280 nm, using the molar extinction coefficient calculated on the basis of the amino acid sequence. Purity and integrity of sortase was determined by SDS-PAGE in the presence and absence of a reducing agent (5 mM 1,4-dithiotreitol) and staining with Coomassie brilliant blue.

gradient to 100% buffer B (buffer A (v/v): 95% water, 5% acetonitrile, 0.1% trifluoro acetic acid (TFA); buffer B (v/v): 5% water, 95% Acetonitrile, 0.1% TFA). The respective chromatogram is shown in FIG. 3.

The Analysis of the reaction mixture with LC-ESI-TOF-MS in positive ion mode shows in peak 4 the product of the native chemical ligation reaction with the mass of 2155 Da.

The respective fragment pattern and masses are shown in the following Table.

| LCR | U | L | P | E | T | G | G | G | R | R | C-NH |
|---|---|---|---|---|---|---|---|---|---|---|---|
| | | | | | 1840 | | | | | | |
| 726 | | | | | | 1114 | | | | | |
| | | | 1237 (1254) | | | | | | | 603 | |
| 726 | | | | | 512 | | | | | 603 | |

| | | |
|---|---|---|
| 1 | Educt: LPETG | 1840 |
| 2 | LCR-GGRR | 1329 |
| 3 | Educt: LPETG dimer | 3676 |
| 4 | Educt: G-Bio | 830 |
| 5 | Educt: C-Bio | 919 |
| 6 | LCR-LPETG-Bio | 2067 |
| 7 | LCR-LPETC-Bio | 2156 |

The protein concentration was determined by measuring the optical density (OD) at 280 nm, using the molar extinction coefficient calculated on the basis of the amino acid sequence. Purity was analyzed by SDS-PAGE in the presence and absence of a reducing agent (5 mM 1,4-dithiotreitol) and staining with Coomassie brilliant blue.

HEK:

The recombinant production was performed by transient transfection of HEK293 cells (human embryonic kidney cell line 293-derived) cultivated in F17 Medium (Invitrogen Corp.). For transfection "293-Fectin" Transfection Reagent (Invitrogen) was used. Transfection was performed as specified in the manufacturer's instructions. Cell culture supernatants were harvested three to seven (3-7) days after transfection. Supernatants were stored at reduced temperature (e.g. −80° C.).

General information regarding the recombinant expression of human immunoglobulins in e.g. HEK293 cells is given in: Meissner, P. et al., Biotechnol. Bioeng. 75 (2001) 197-203.

The protein concentration was determined by measuring the optical density (OD) at 280 nm, using the molar extinction coefficient calculated on the basis of the amino acid sequence. Purity was analyzed by SDS-PAGE in the presence and absence of a reducing agent (5 mM 1,4-dithiotreitol) and staining with Coomassie brilliant blue.

Example 3

Sortase Mediated Conjugation

A reaction mixture comprising 0.5 mM of the polypeptide LCR640-ULPETGGGRRC (U: LCR640 fluorophore conjugated beta-alanine; SEQ ID NO: 33) Fc-region fragment comprising a LPETG sortase motif (SEQ ID NO: 04), 1.5 mM of an N-terminal biotinylated N-terminal cysteine comprising peptide with the C-terminally biotinylated amino acid sequence CAAA (SEQ ID NO: 03) and 50 μM *Staphylococcus aureus* Sortase A in 50 mM Tris pH 7.5, 150 mM NaCl, 10 mM CaCl$_2$ was incubated at 37° C. for 18 hours.

In the samples were analyzed without stopping the reaction.

The samples (10 μl) were injected on a Vydac C18 column of an LC-Ms system and separated with a 30 min. linear Example 4

Reporter Immobilization Assay

More detailed analysis of Sortases generating a thioester for native chemical ligation was done using a reporter immobilization assay (REIA) as reported in European Patent application EP14198535 and as outlined below.

Reaction Mixture:
- 20 μM *Staphylococcus aureus* sortase A (Sa-SrtA)
- 100 μM nucleophile (GGGG/AAAA/CAAA)
- 20 μM glucose dehydrogenase with C-terminal sortase motif (LPXTG)
- 250 mM MESNA
- 0.5 mM TCEP or

- 100 μM *Listeria monocytogenes* sortase A (Lm-SrtA)
- 100 μM nucleophile (GGGG/AAAA/CAAA)
- 20 μM glucose dehydrogenase with C-terminal sortase motif (LPXTG)
- 250 mM MESNA.

The glucose dehydrogenase was expressed and purified as described in WO 2007/118647.

Both reaction mixtures were prepared in 50 mM Tris-HCl buffer pH 7.5, 150 mM NaCl, 10 mM CaCl$_2$.

The reaction mixture was incubated at 37° C. for up to 60 hours. The reaction was stopped by addition of a 60-fold excess of inhibition buffer (50 mM Tris, pH 7.5, 200 mM NaCl, 10 mM CaCl$_2$, 5 mM iodoacetamide). The stopped reaction mixture was centrifuged for 10 min at 5000×g. The supernatant (50 μL) was added to 100 μL of 50 mM Tris buffer (pH 7.5) comprising 200 mM NaCl, 10 mM CaCl$_2$ and streptavidin coated magnetic beads. The mixture was incubated for 30 min at 30° C. with shaking at 200 rpm. Thereafter the magnetic beads were washed five times with 300 μL washing buffer each (50 mM Tris, pH 7.5, 200 mM NaCl, 10 mM CaCl$_2$, 5 mg/mL BSA, 0.1% Triton X-100) in V-bottom micro-titer-plates using a magnet and a vacuum pump. Afterwards the beads were resuspended in 100 μL citrate buffer and 80 μL thereof was transferred to a new well. Thereto 150 μL test buffer (0.2 M sodium citrate, pH 5.8, 0.3 g/L 4-nitrosoaniline, 1 mM CaCl$_2$, 30 mM glucose) were added. The kinetic of the reporter enzyme was measured over a time period of 5 min at 620 nm.

Figure 5:
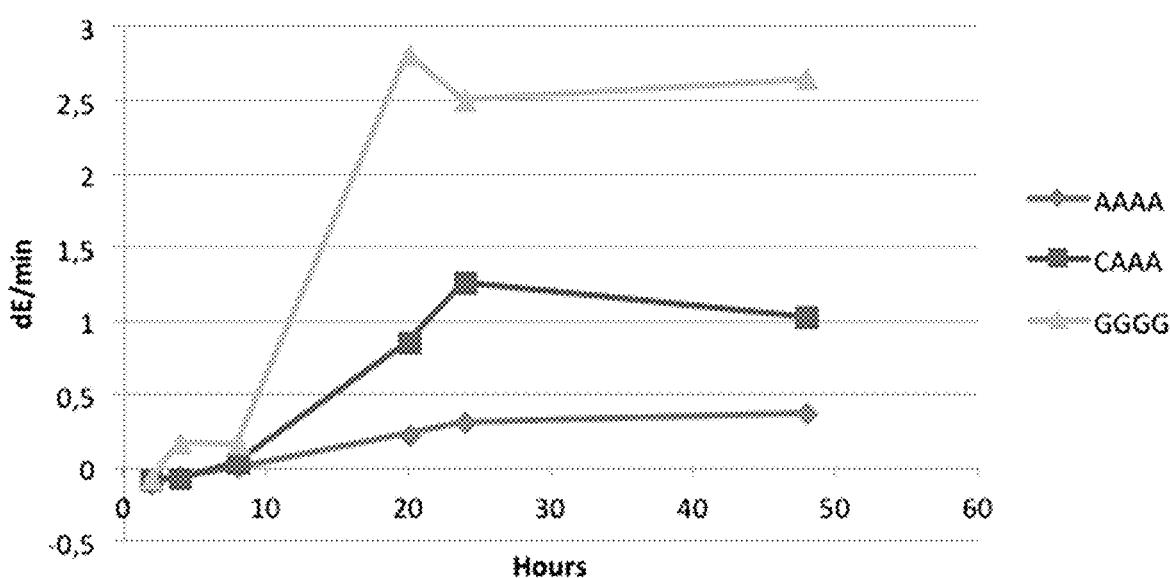
FIG. 5 Enzymatic activity of Sa-SrtA using a REIA with different Nucleophiles.
Figure 6:
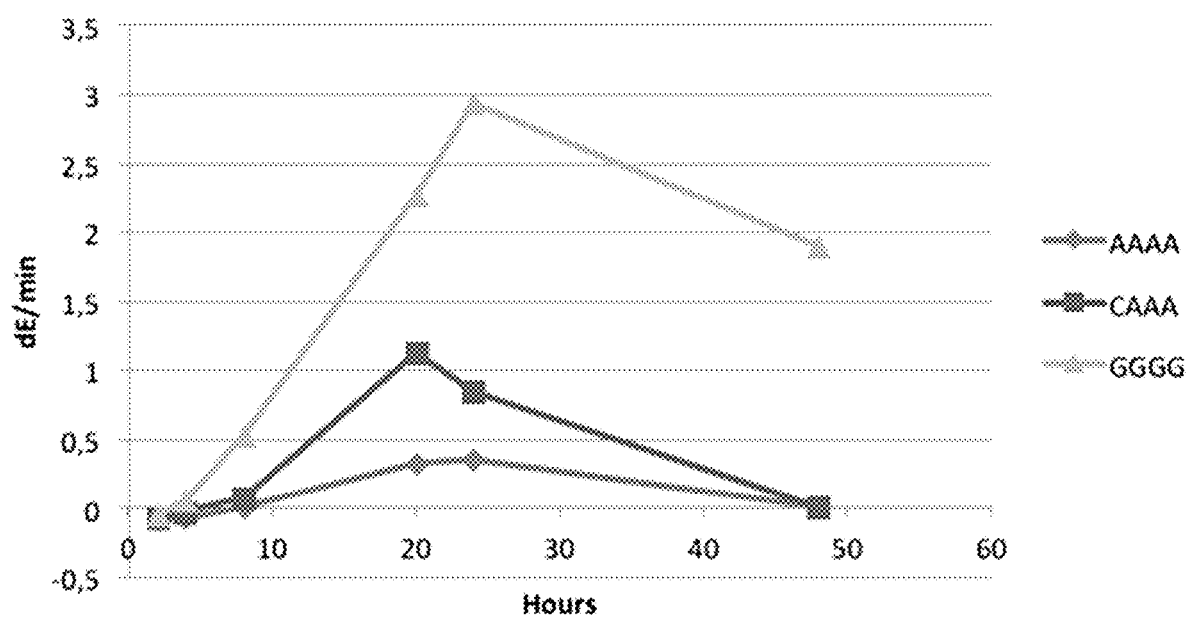
FIG. 6 Enzymatic activity of Lm-SrtA using a REIA with different Nucleophiles.

The results are shown in FIGS. 5 and 6.

Although the foregoing invention has been described in some detail by way of illustration and example for purposes of clarity of understanding, the descriptions and examples should not be construed as limiting the scope of the invention.

---

The invention claimed is:

1. A method for enzymatic conjugation of two polypeptides comprising: incubating in an aqueous environment
   a first polypeptide comprising the amino acid sequence LPXTG (SEQ ID NO: 01, wherein X can be any amino acid residue);
   a second polypeptide that has at its N-terminus a cysteine amino acid residue followed by one to three glycine amino acid residues; and
   a third polypeptide that is a sortase A or a catalytically active fragment thereof;
thereby forming a thioester bond.

2. The method according to claim 1, wherein the third polypeptide is selected from *Staphylococcus aureus* sortase A, a catalytically active fragment of *Staphylococcus aureus* sortase A, *Listeria monocytogenes* Sortase A, and a catalytically active fragment of *Listeria monocytogenes* Sortase A.

3. The method according to claim 1, wherein the incubating is further in the presence of a thiol additive.

4. The method according to claim 3, wherein the thiol additive is selected from the group consisting of thiophenol, 4-mercaptophenylacetic acid (MPAA), and 2-mercaptoethanesulfonate (MESNA), and combinations thereof.

5. The method according to claim 1, wherein the first polypeptide comprises at its C-terminus the amino acid sequence LPXTG (SEQ ID NO: 01, wherein X can be any amino acid residue).

6. The method according to claim 1, wherein the first polypeptide comprises at its C-terminus the amino acid sequence LPETG (SEQ ID NO: 04).

7. The method according to claim 1, wherein the second polypeptide has the amino acid sequence CGGG (SEQ ID NO: 02) at its N-terminus.

8. The method according to claim 1, wherein the first polypeptide and the second polypeptide are independently of each other selected from the group consisting of an antibody variable domain, an antibody heavy chain, an antibody Fab-fragment, an antibody Fc-region, a tag, and a linker.

9. The method according to claim 1, wherein the third polypeptide has the amino acid sequence of SEQ ID NO: 05 or SEQ ID NO: 06.

10. A method for enzymatic conjugation of two polypeptides comprising: incubating in an aqueous environment a first polypeptide comprising the amino acid sequence LPXTG (SEQ ID NO: 01, wherein X can be any amino acid residue);

a second polypeptide that has at its N-terminus a cysteine amino acid residue followed by one to three glycine amino acid residues or one to three alanine amino acid residues; and a third polypeptide that is *Listeria monocytogenes* Sortase A or a catalytically active fragment of *Listeria monocytogenes* Sortase A that is not a catalytically active fragment derived from *Staphylococcus aureus* sortase A, thereby forming a thioester bond.

11. The method according to claim 10, wherein the incubating is further in the presence of a thiol additive.

12. The method according to claim 11, wherein the thiol additive is selected from the group consisting of thiophenol, 4-mercaptophenylacetic acid (MPAA), and 2-mercaptoethanesulfonate (MESNA), and combinations thereof.

13. The method according to claim 10, wherein the first polypeptide comprises at its C-terminus the amino acid sequence LPXTG (SEQ ID NO: 01, wherein X can be any amino acid residue).

14. The method according to claim 10, wherein the first polypeptide comprises at its C-terminus the amino acid sequence LPETG (SEQ ID NO: 04).

15. The method according to claim 10, wherein the second polypeptide has the amino acid sequence CGGG (SEQ ID NO: 02) or CAAA (SEQ ID NO: 03) at its N-terminus.

16. The method according to claim 10, wherein the first polypeptide and the second polypeptide are independently of each other selected from the group consisting of an antibody variable domain, an antibody heavy chain, an antibody Fab-fragment, an antibody Fc-region, a tag, and a linker.

* * * * *